United States Patent
Yoon et al.

(10) Patent No.: US 10,227,560 B2
(45) Date of Patent: Mar. 12, 2019

(54) BIOMIMETIC SUPPORT FOR THREE-DIMENSIONAL CELL CULTURING, METHOD FOR MANUFACTURING SAME, AND USE THEREOF

(71) Applicant: PUSAN NATIONAL UNIVERSITY INDUSTRY-UNIVERSITY COOPERATION FOUNDATION, Busan (KR)

(72) Inventors: Sik Yoon, Busan (KR); Jong-Young Kwak, Suwon-si (KR); Song-Wan Jin, Siheung-si (KR); Young Hun Jeong, Daegu (KR); Chang Gun Kim, Suwon-si (KR); Da Jeong Choi, Daegu (KR); Hae Yeong Kang, Daejeon (KR); Subhan Fazli, Yangsan-si (KR); Muhamad Ikram, Yangsan-si (KR)

(73) Assignee: PUSAN NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 33 days.

(21) Appl. No.: 15/326,638

(22) PCT Filed: Jul. 16, 2015

(86) PCT No.: PCT/KR2015/007394
§ 371 (c)(1),
(2) Date: Jan. 16, 2017

(87) PCT Pub. No.: WO2016/010377
PCT Pub. Date: Jan. 21, 2016

(65) Prior Publication Data
US 2017/0204365 A1    Jul. 20, 2017

(30) Foreign Application Priority Data

Jul. 16, 2014  (KR) .................. 10-2014-0089858
Aug. 1, 2014   (KR) .................. 10-2014-0098995

(51) Int. Cl.
*C12N 5/00*     (2006.01)
*G01N 33/50*    (2006.01)
(Continued)

(52) U.S. Cl.
CPC ....... *C12N 5/0062* (2013.01); *G01N 33/5011* (2013.01); *G01N 33/54366* (2013.01);
(Continued)

(58) Field of Classification Search
None
See application file for complete search history.

(56) References Cited

U.S. PATENT DOCUMENTS

2004/0072338 A1   4/2004  Tsuzuki et al.
2005/0233442 A1*  10/2005  Toda .................... C12N 5/0068
                                                       435/325

(Continued)

FOREIGN PATENT DOCUMENTS

JP   2004-31135 A       2/2004
KR   10-2007-0024092 A  3/2007
KR   10-2010-0051294 A  5/2010

OTHER PUBLICATIONS

Batorsky, Anna; et al; "Encapsulation of Adult Human Mesenchymal Stem Cells Within Collagen-Agarose Microenvironments" Biotechnology and Bioengineering, 92, 492-500, 2005 (Year: 2005).*

(Continued)

*Primary Examiner* — David W Berke-Schlessel
(74) *Attorney, Agent, or Firm* — Revolution IP, PLLC

(57) ABSTRACT

Disclosed is a method for manufacturing a composite nanofiber support and a fish collagen/synthetic polymer nanofiber
(Continued)

support manufactured by the method, wherein the method comprises: a first step for dissolving a synthetic polymer in an organic solvent; a second step for dissolving a fish collagen in water to prepare an aqueous fish collagen solution; a third step for adding the aqueous fish collagen solution prepared in the second step to the synthetic polymer solution prepared in the first step, followed by mixing; and a fourth step for electrospinning the mixture solution prepared in the third step to manufacture a nanofiber support.

8 Claims, 66 Drawing Sheets

Specification includes a Sequence Listing.

(51) Int. Cl.
    *G01N 33/543*     (2006.01)
    *C12M 1/12*     (2006.01)
(52) U.S. Cl.
    CPC ............ *C12M 25/02* (2013.01); *C12M 25/14* (2013.01); *C12N 2501/90* (2013.01); *C12N 2501/998* (2013.01); *C12N 2533/54* (2013.01); *C12N 2533/74* (2013.01); *C12N 2533/76* (2013.01)

(56) References Cited

U.S. PATENT DOCUMENTS

2008/0233162 A1    9/2008   Lee et al.
2010/0120149 A1    5/2010   Kim et al.

OTHER PUBLICATIONS

Hunt, Nicola; Grover, Liam M; "Cell encapsulation using biopolymer gels for regenerative medicine" Biotechnology Letters, 32, 733-742, 2010 (Year: 2010).*

Drury, Jeanie L; Mooney, David J; "Hydrogels for tissue engineering: scaffold design variables and applications" Biomaterials, 24, 4337-4351, 2003 (Year: 2003).*

Gang Zhou, et al., "Research on the Structure of Fish Collagen Nanofibers Influenced Cell Growth", Journal of Nanomaterials, Jun. 6, 2013, pp. 1-7, vol. 2013.

* cited by examiner

[FIGURE 1]
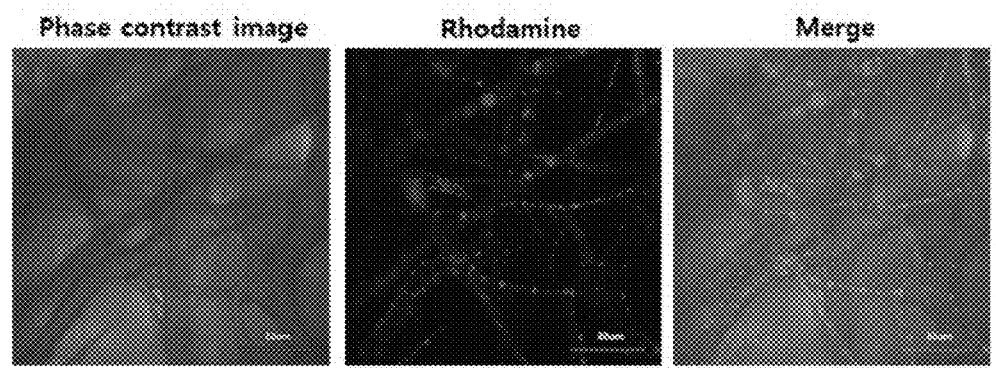
[FIGURE 2]
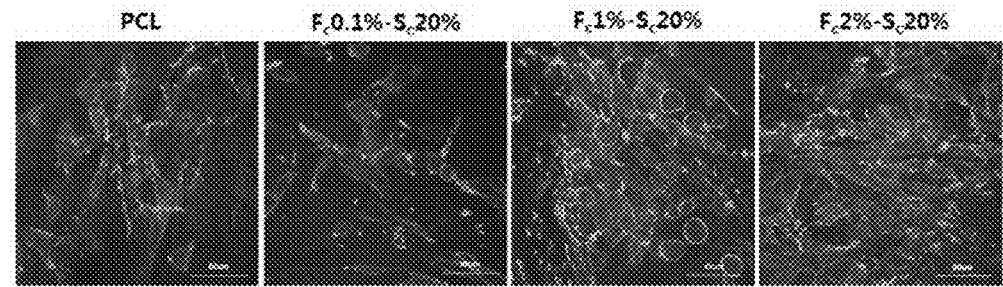

[FIGURE 3]
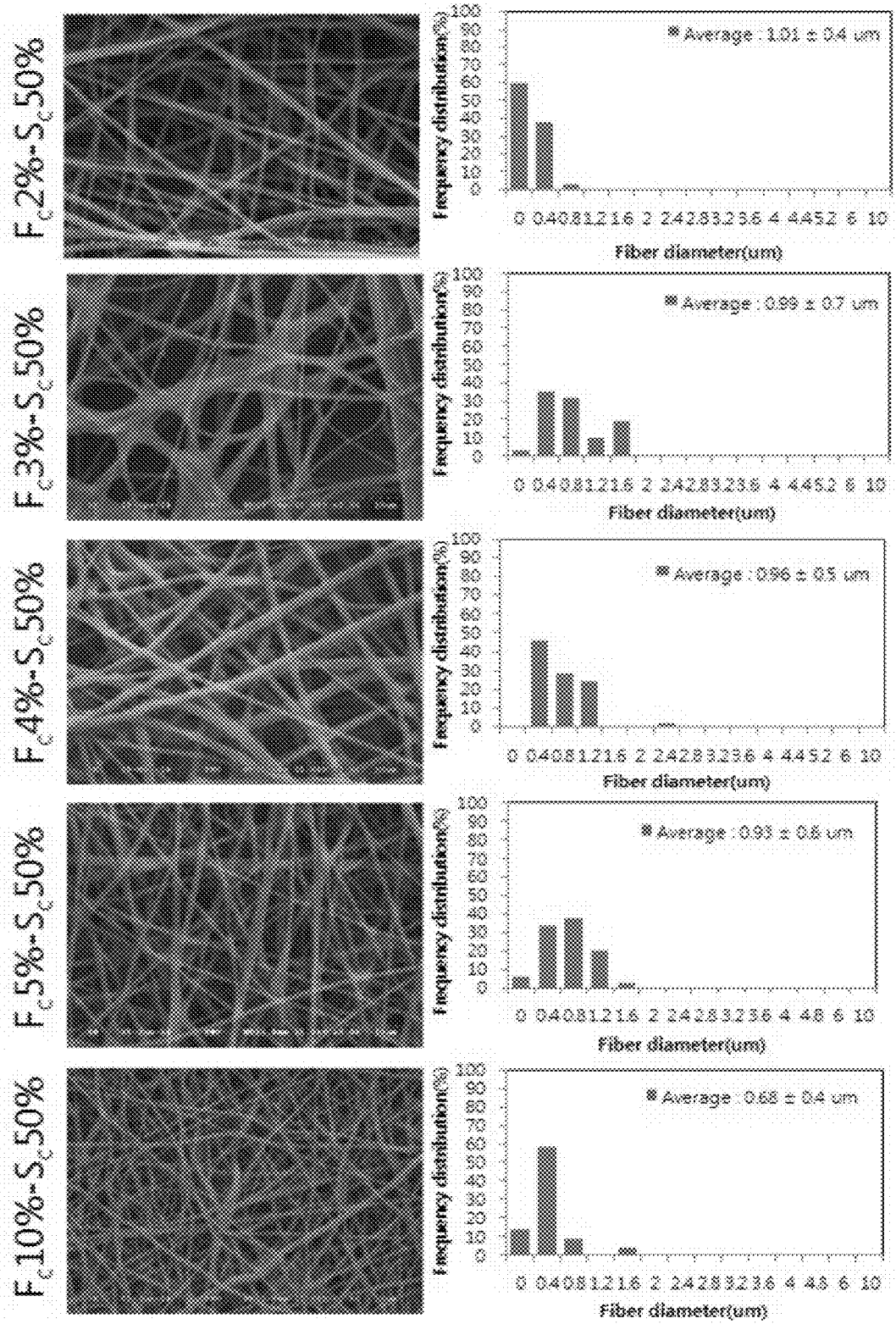

[FIGURE 4]
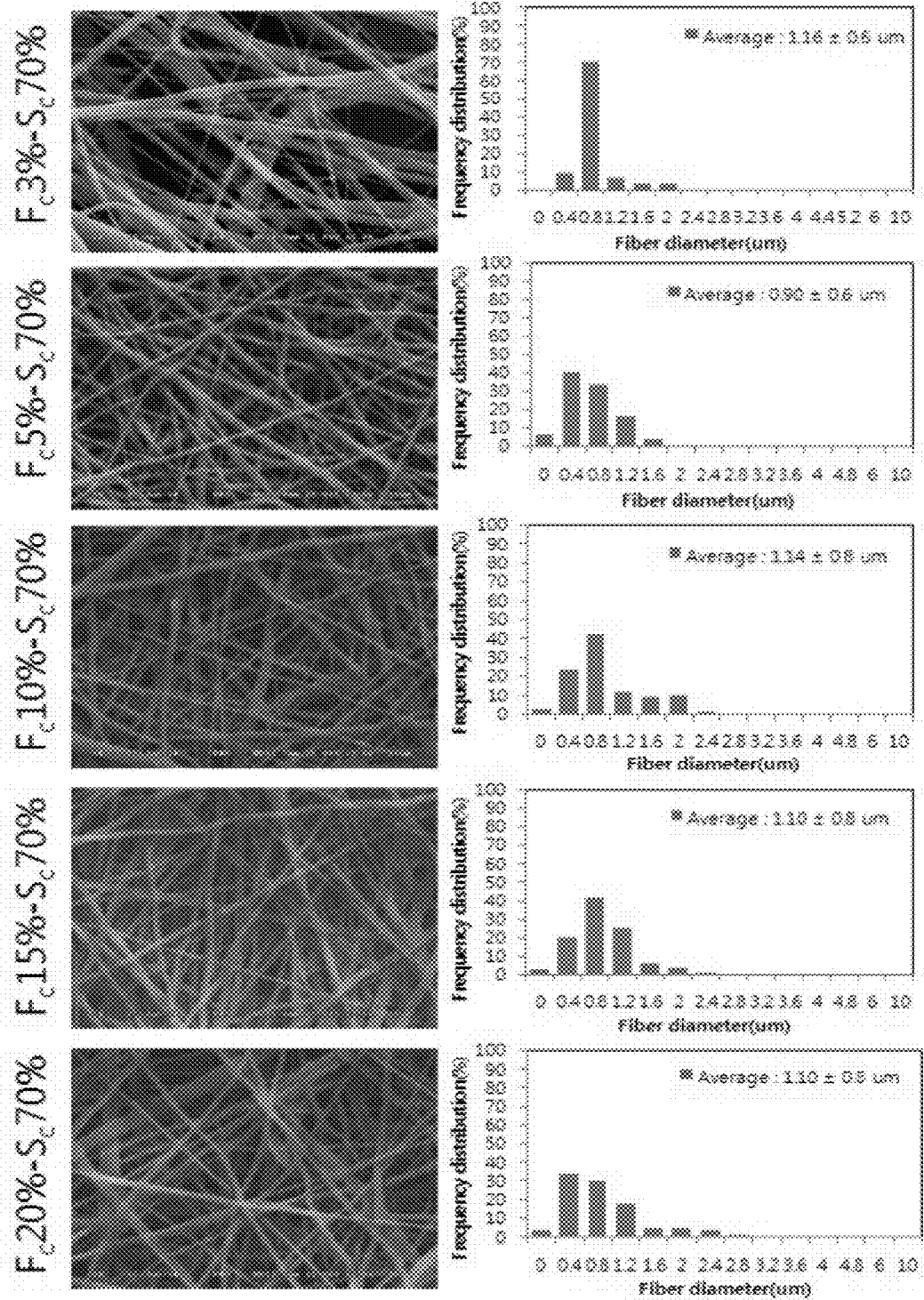

[FIGURE 5]
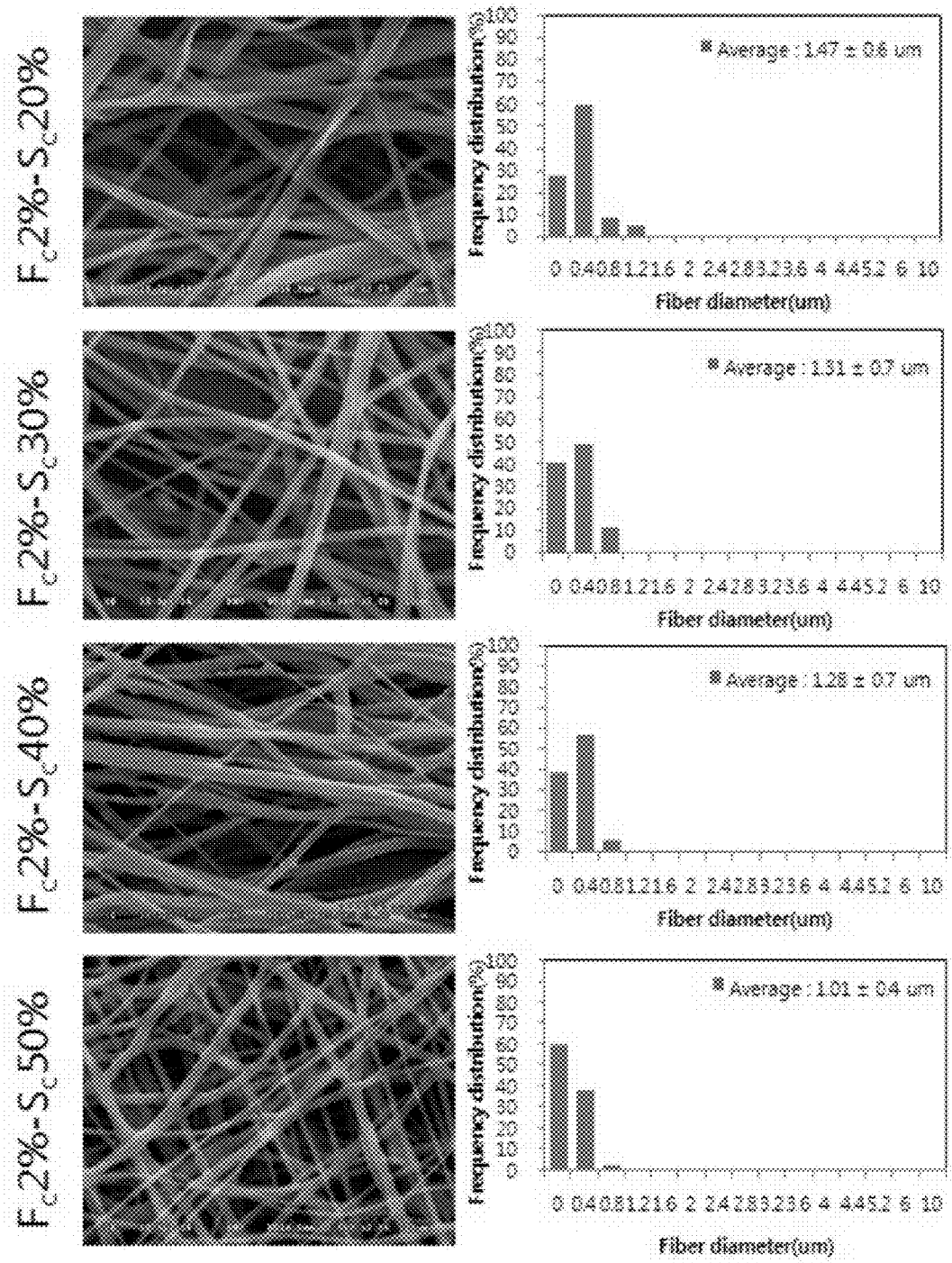

[FIGURE 6]
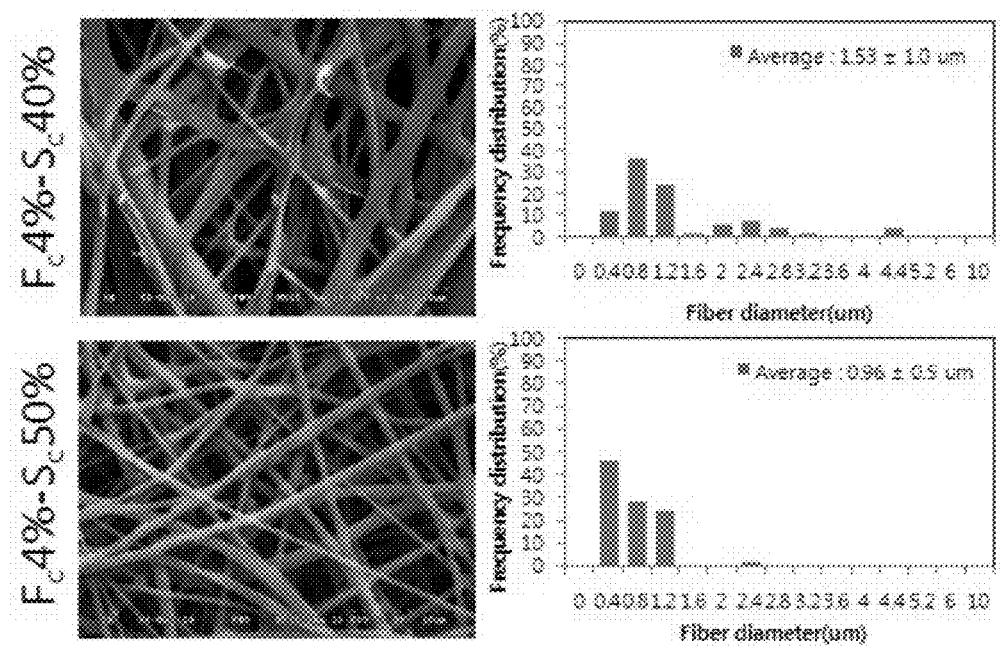

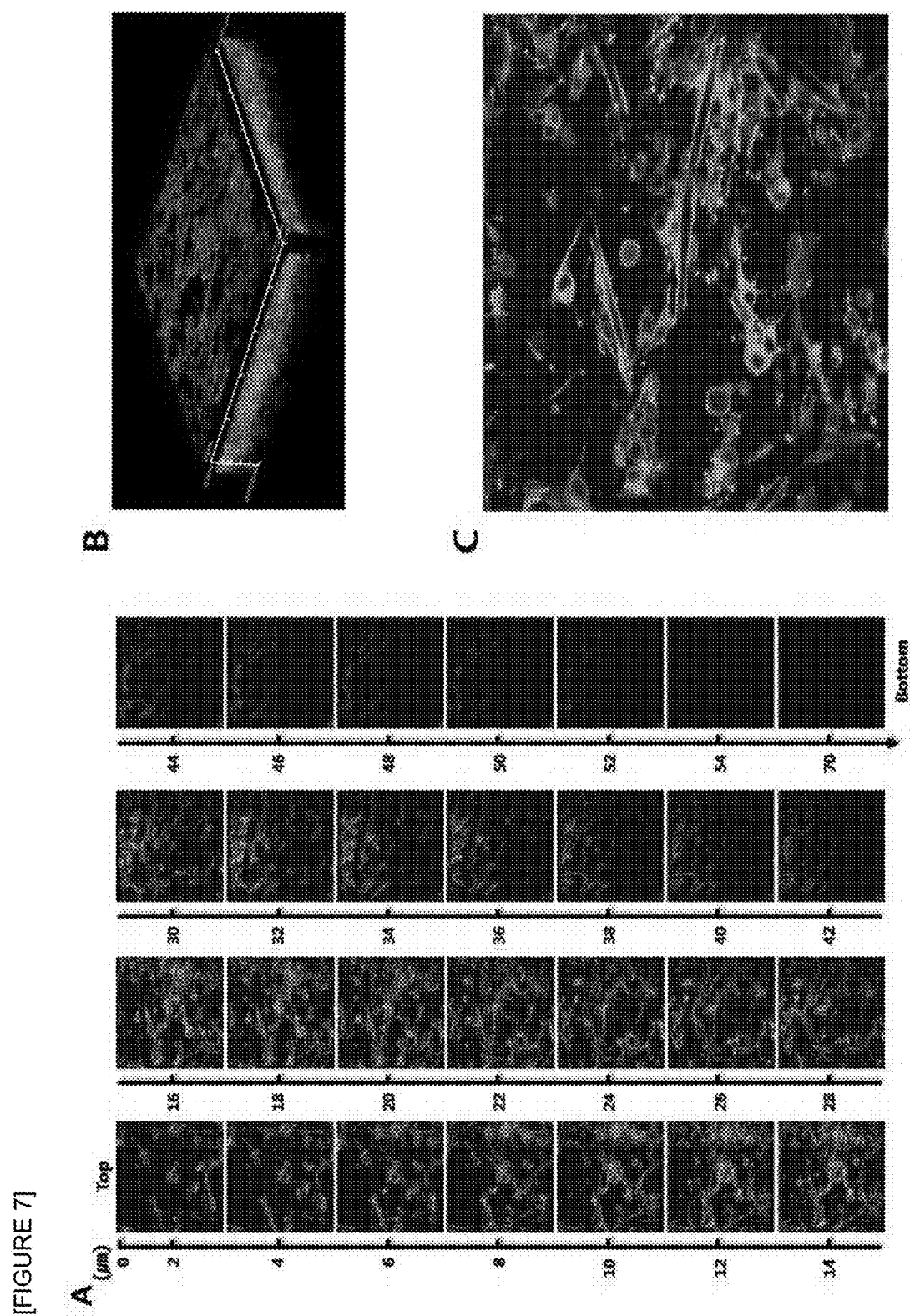
[FIGURE 7]

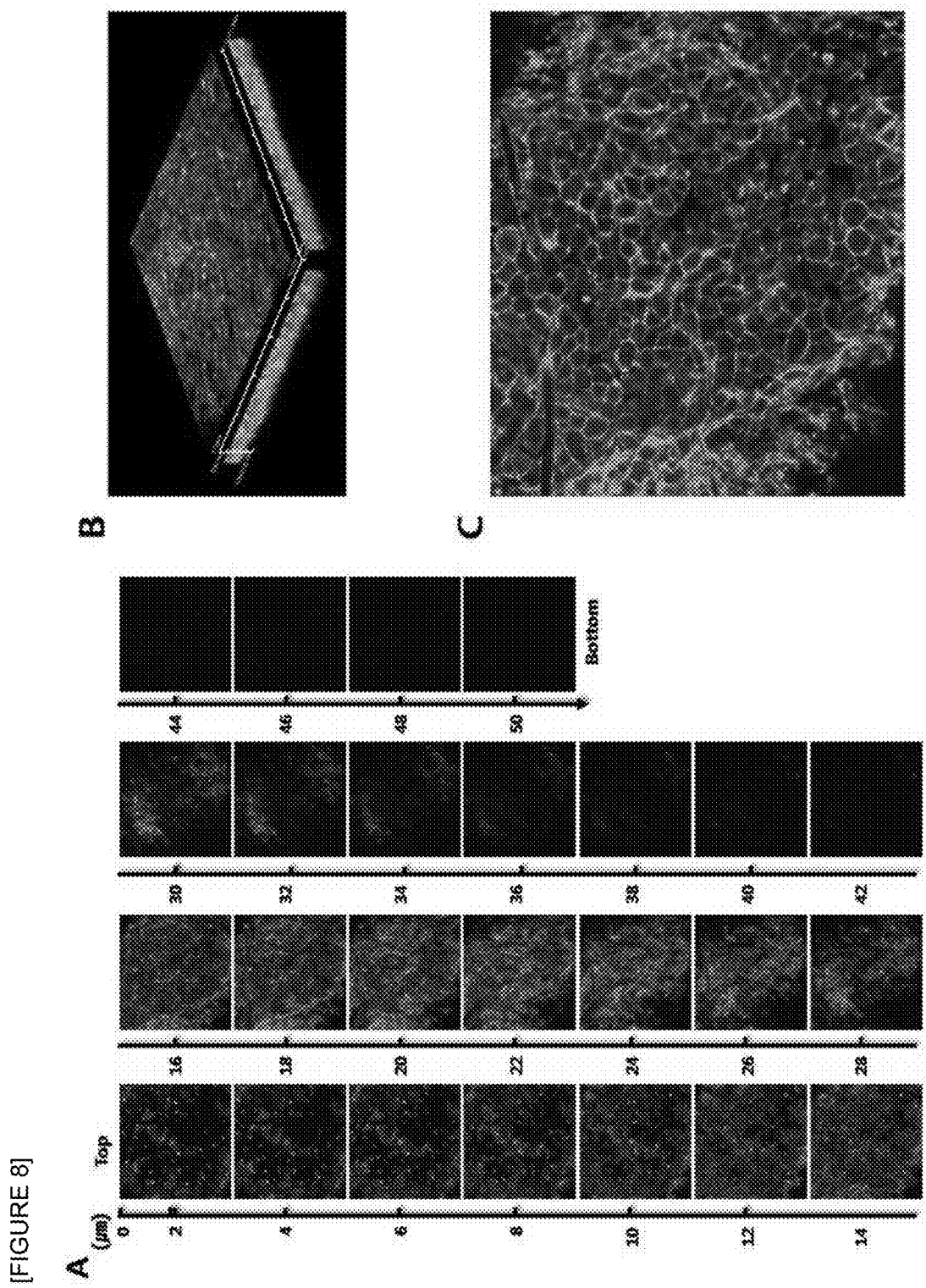
[FIGURE 8]

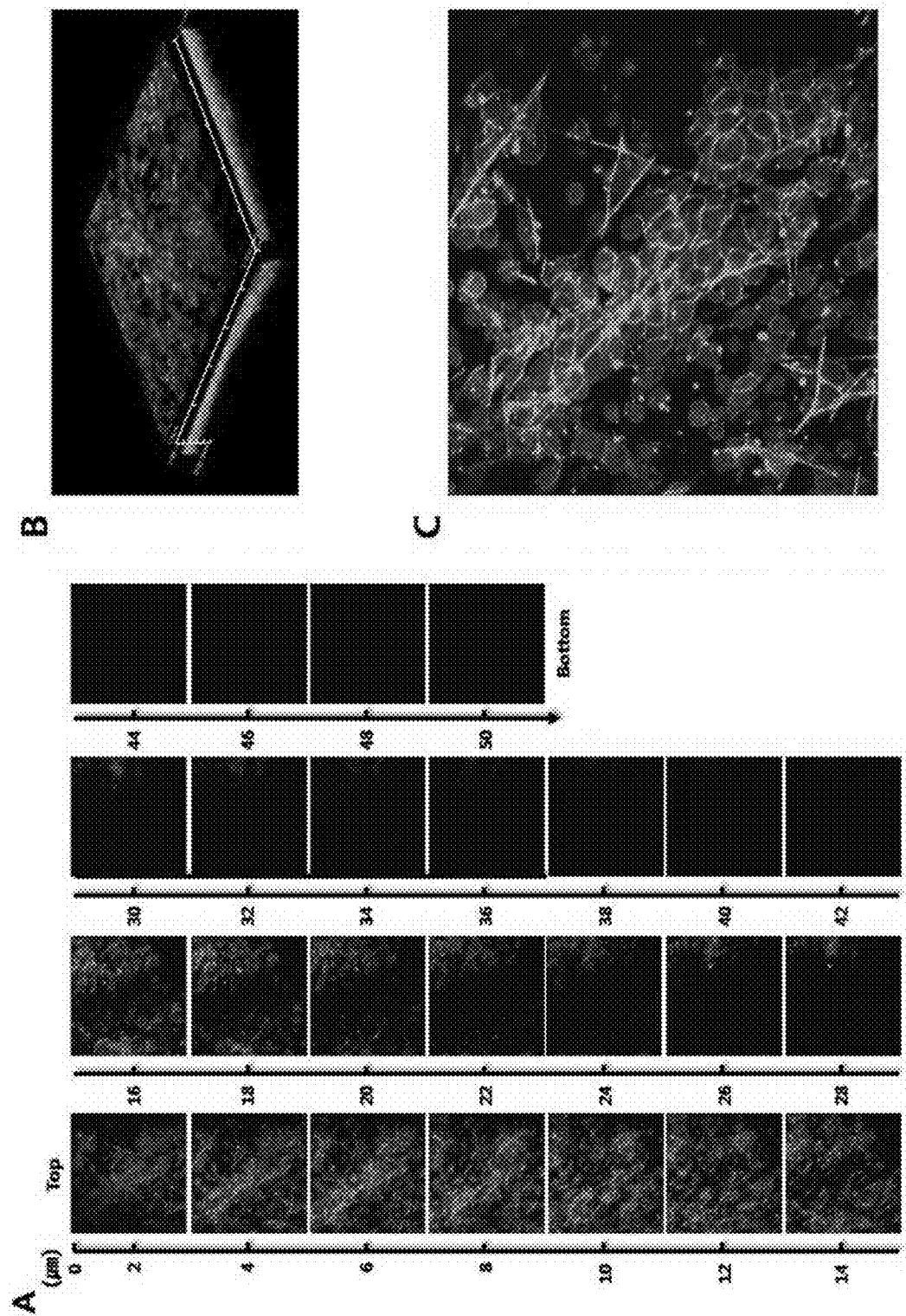
[FIGURE 9]

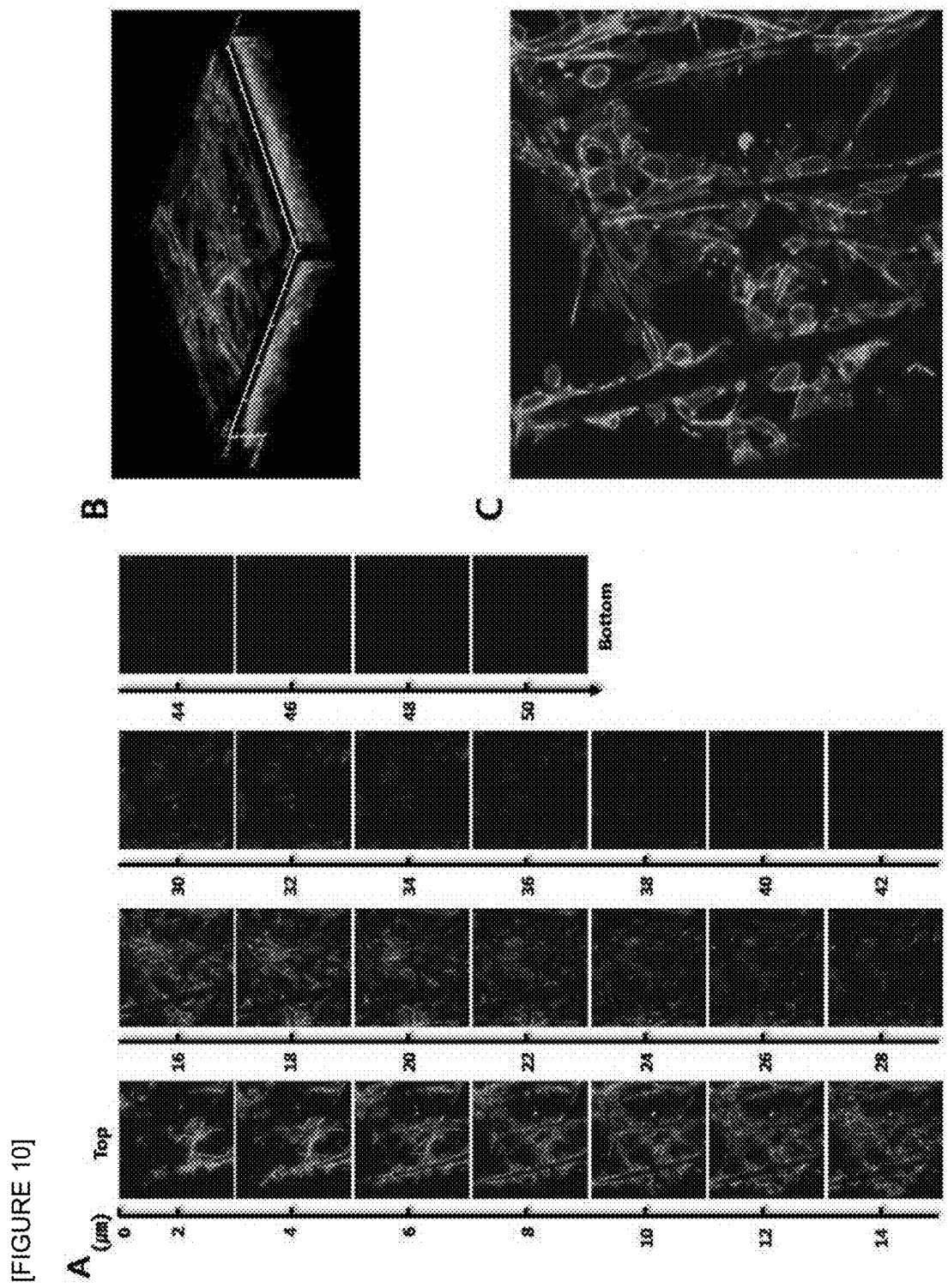
[FIGURE 10]

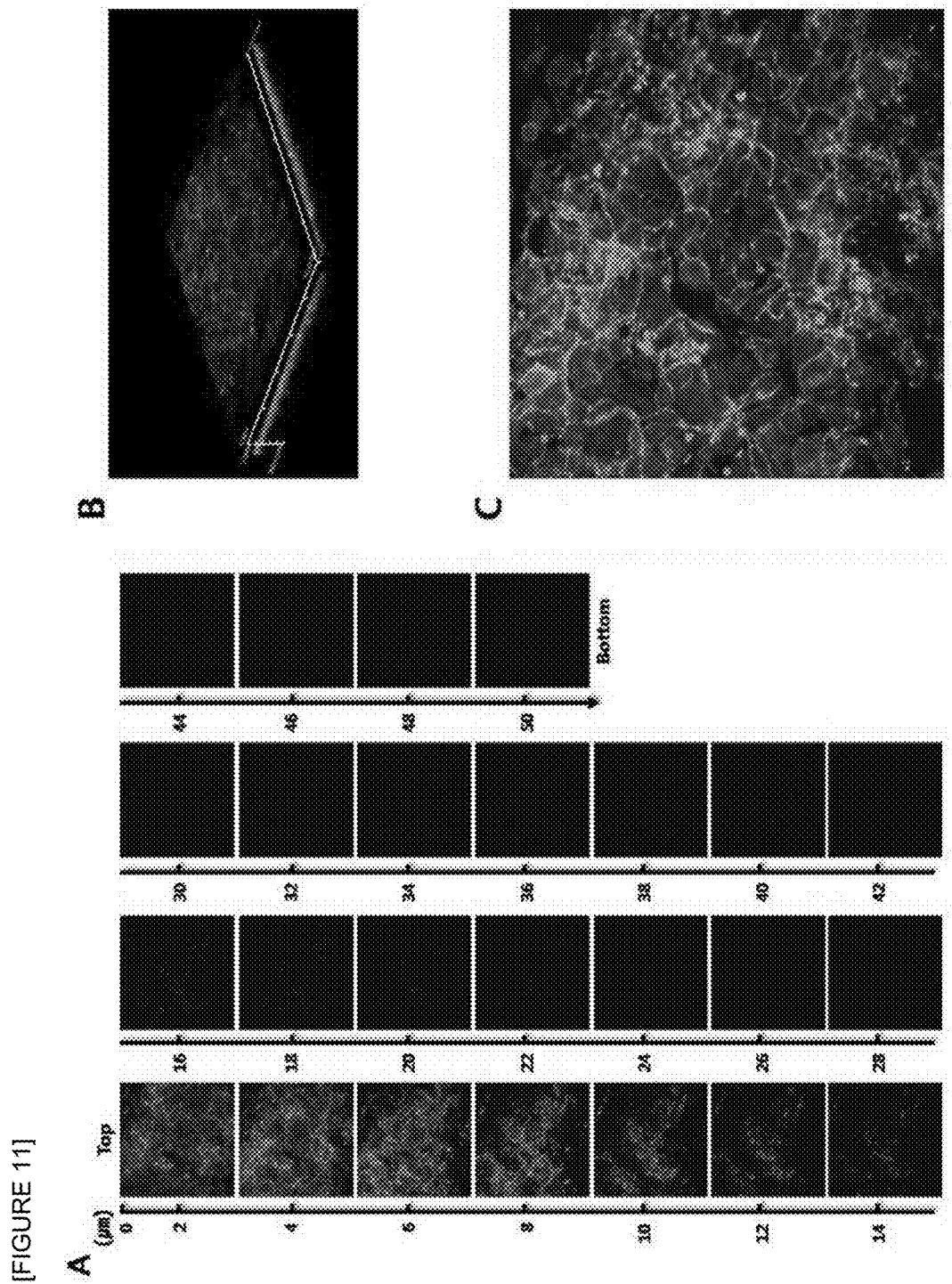
[FIGURE 11]

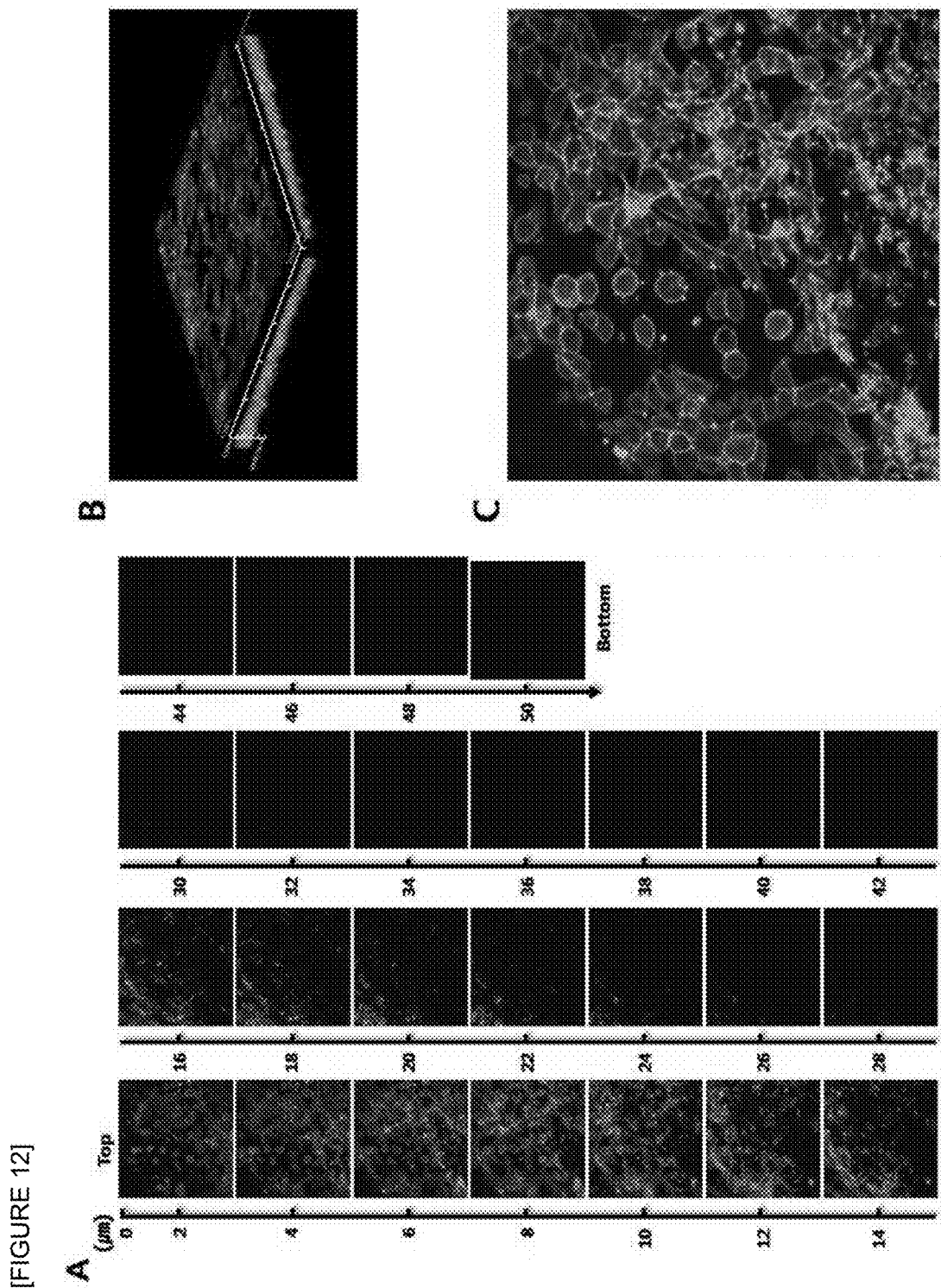
[FIGURE 12]

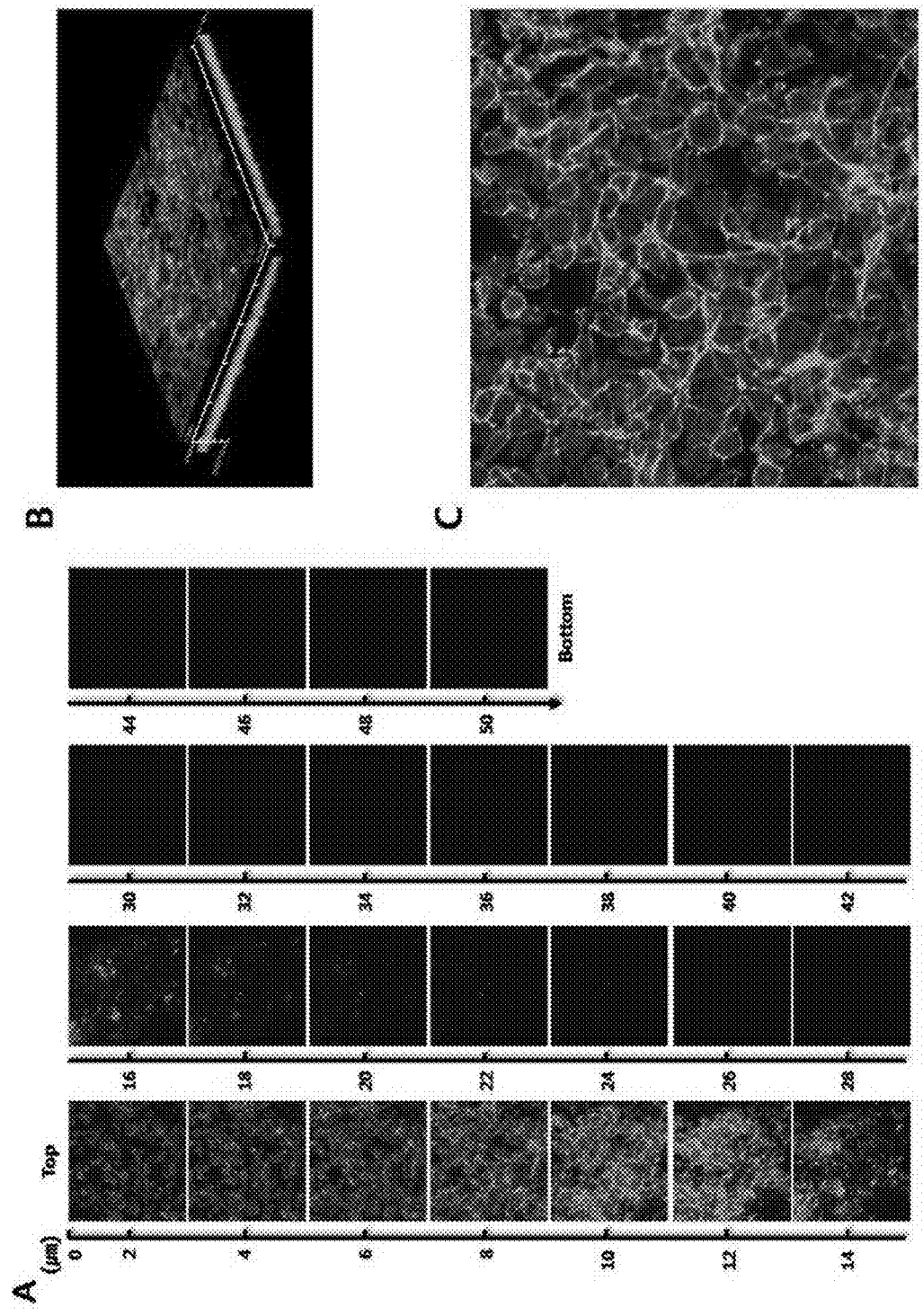
[FIGURE 13]

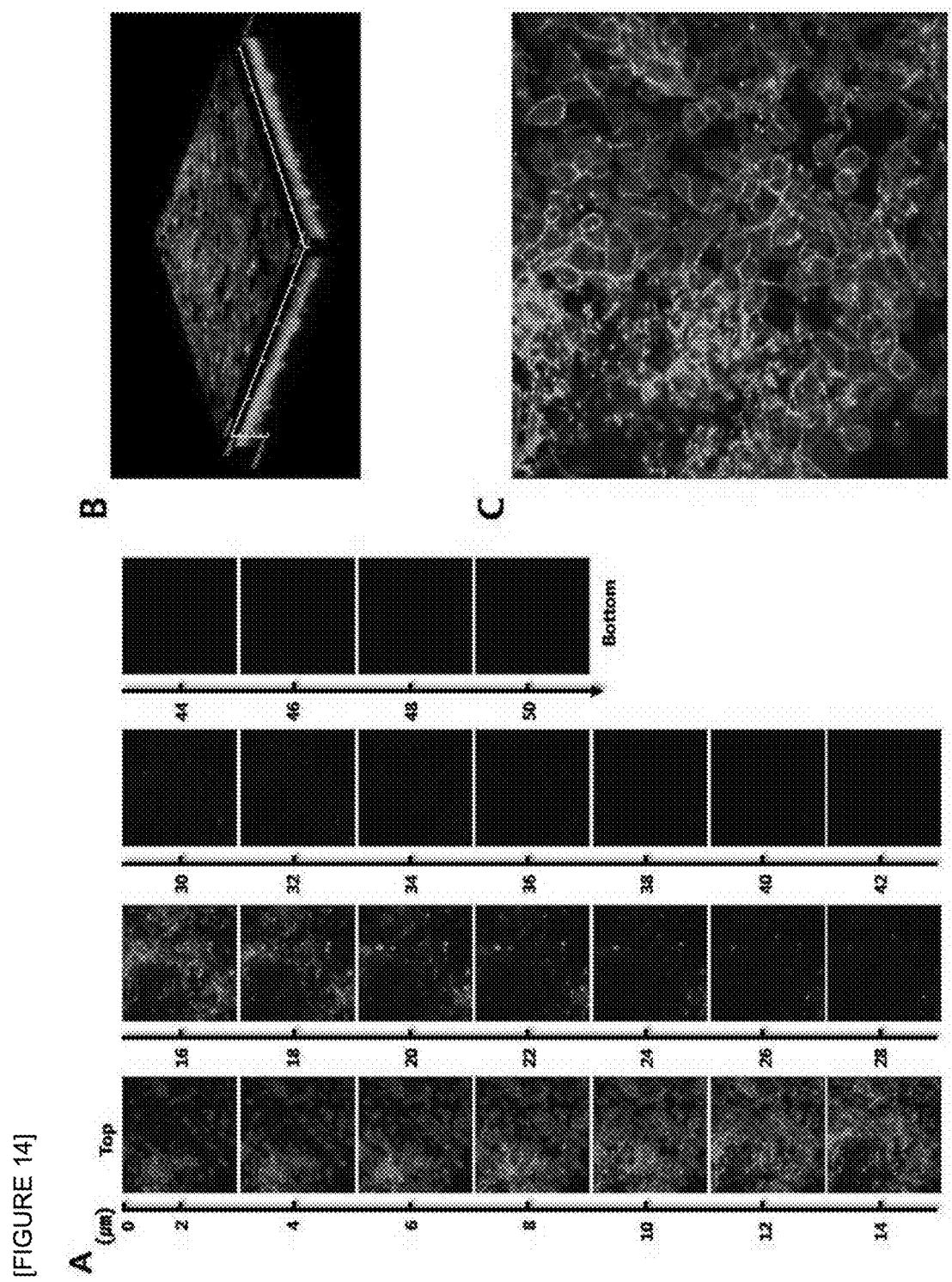
[FIGURE 14]

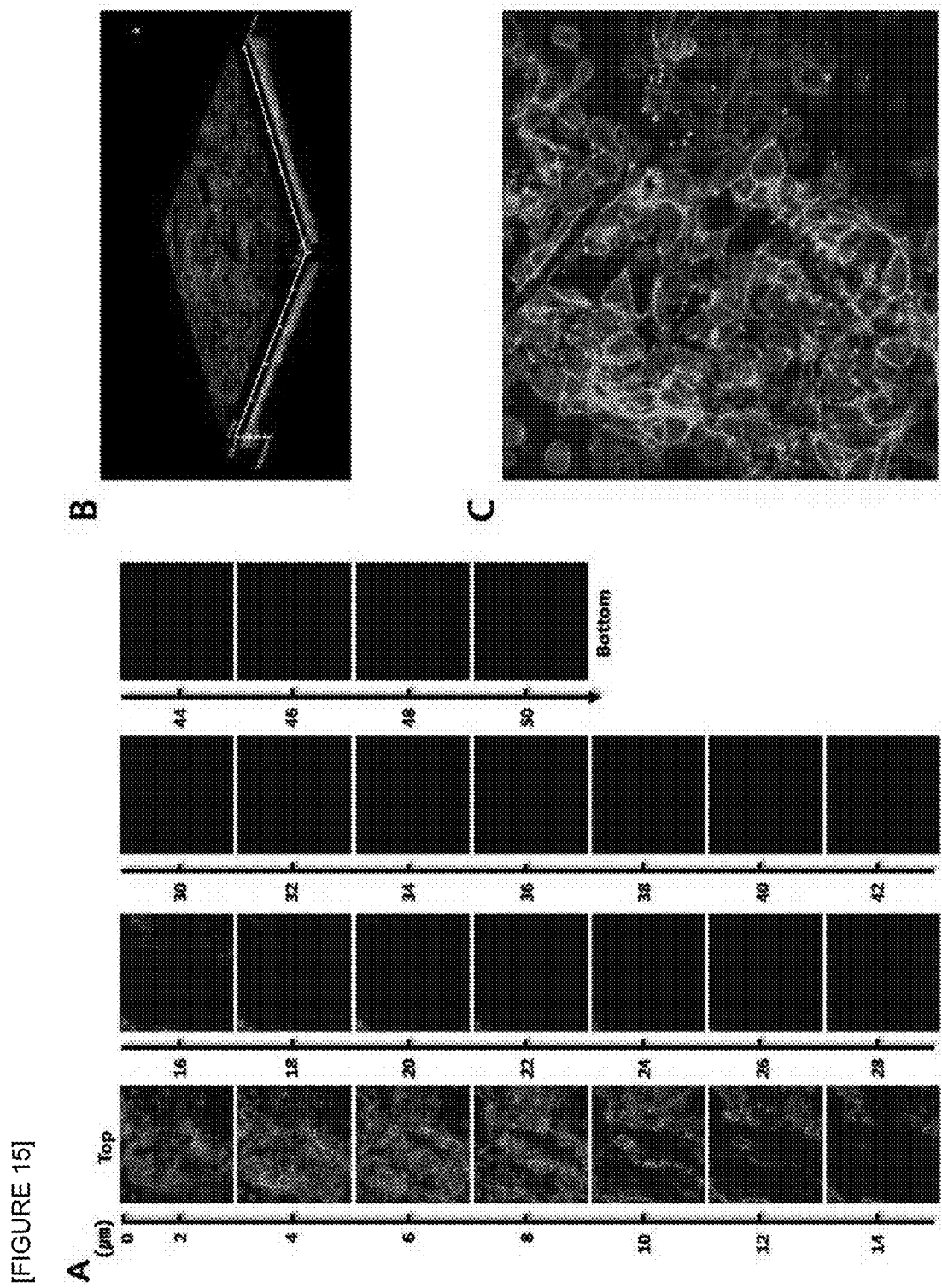
[FIGURE 15]

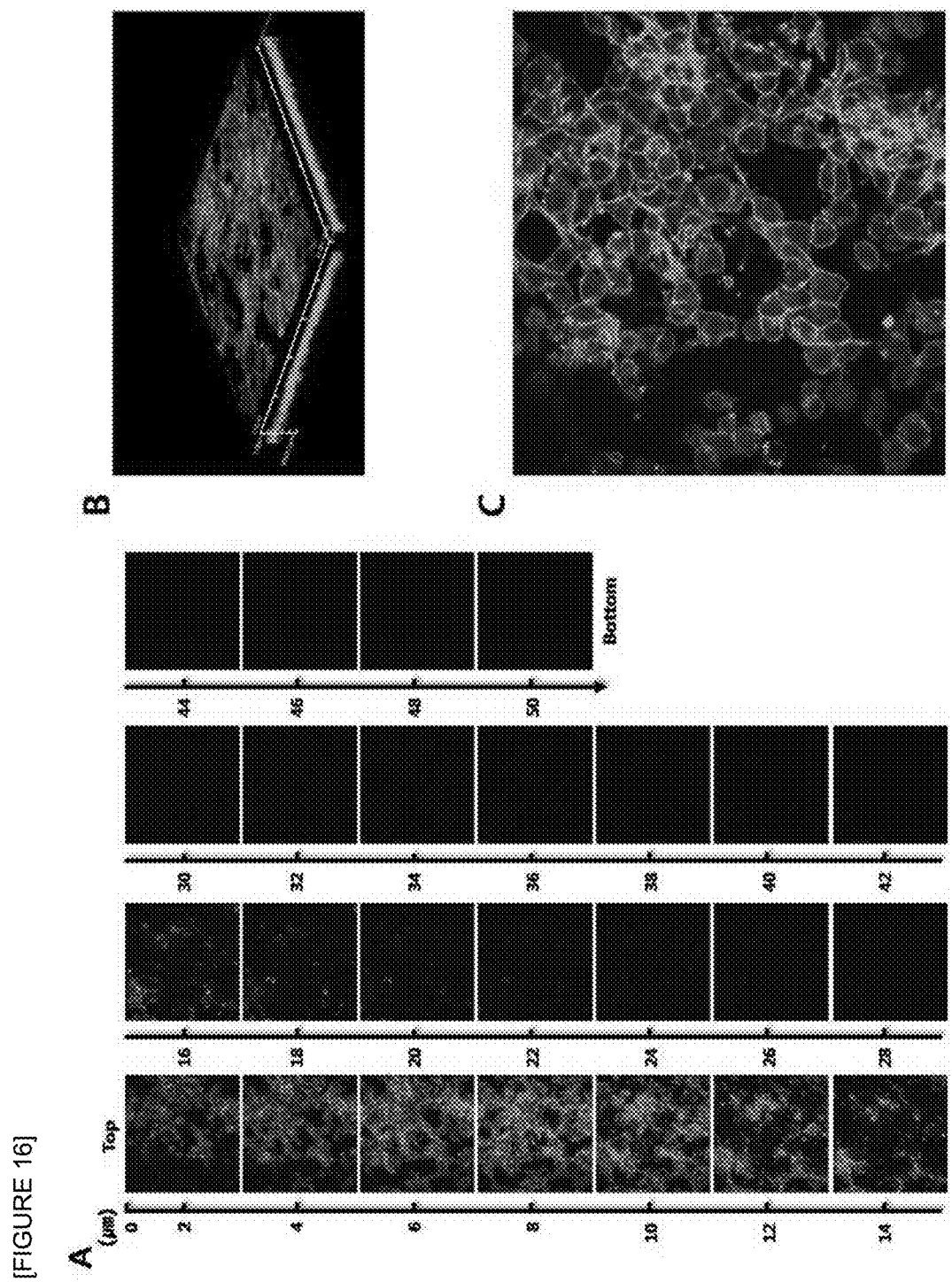
[FIGURE 16]

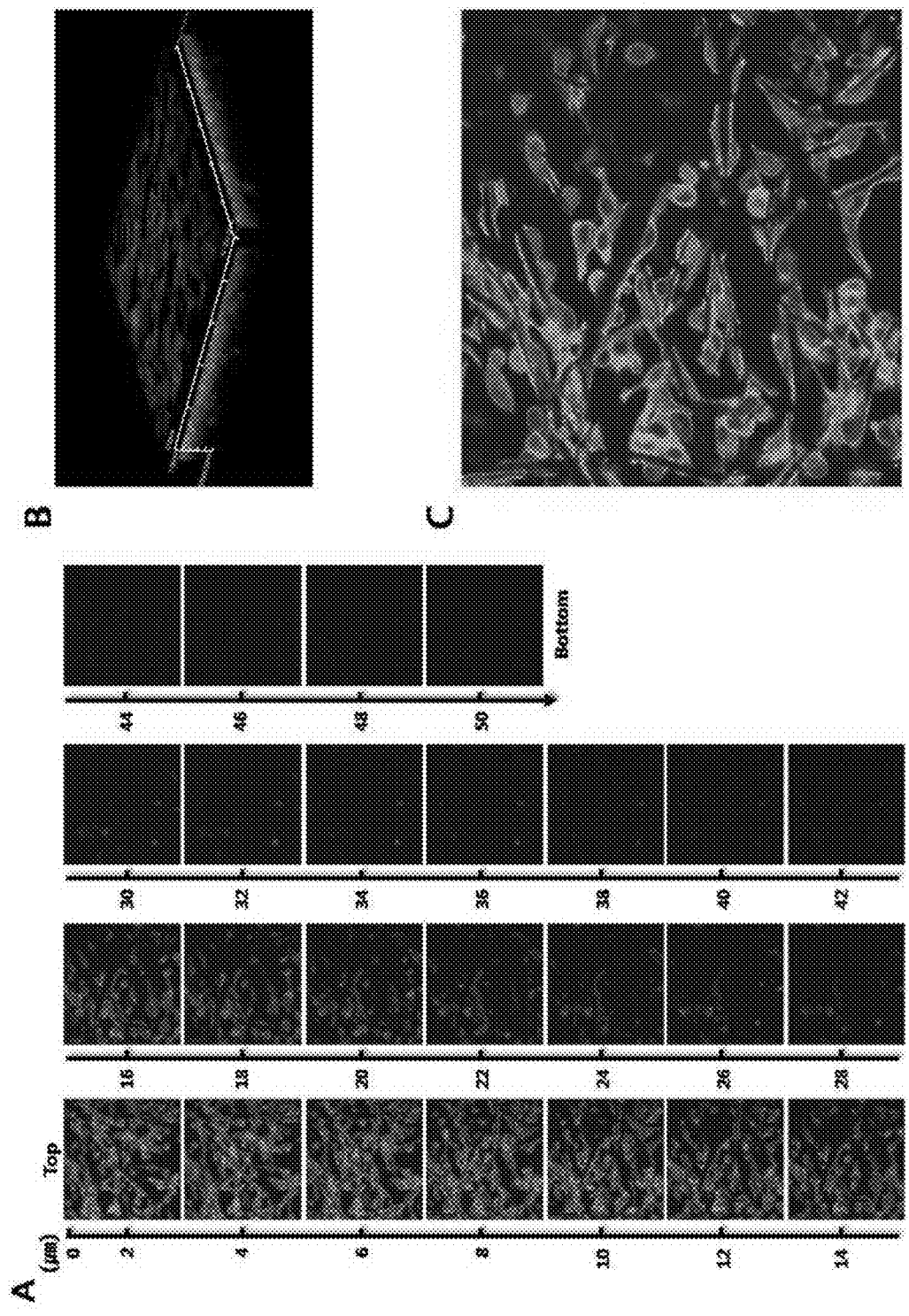
[FIGURE 17]

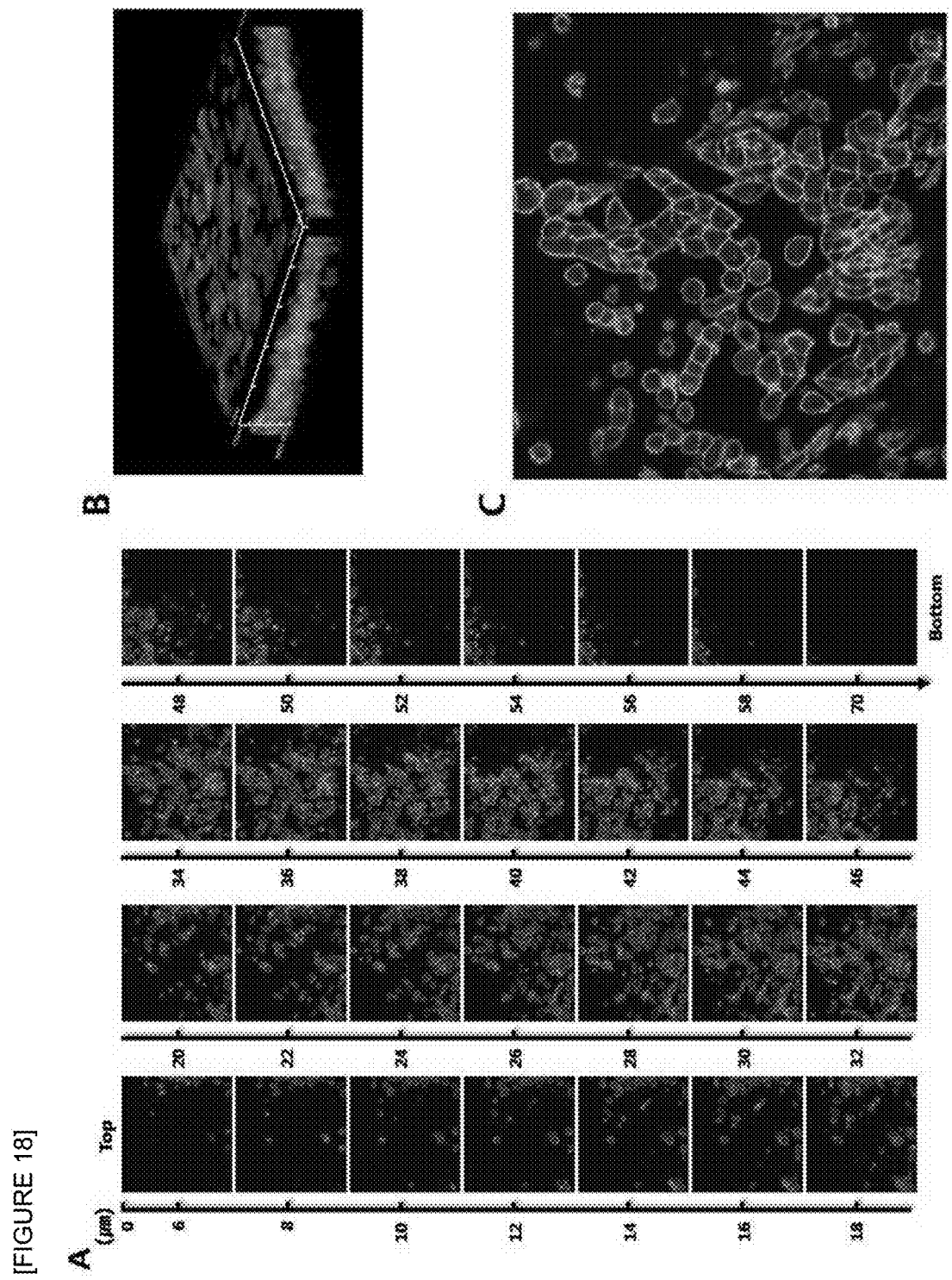
[FIGURE 18]

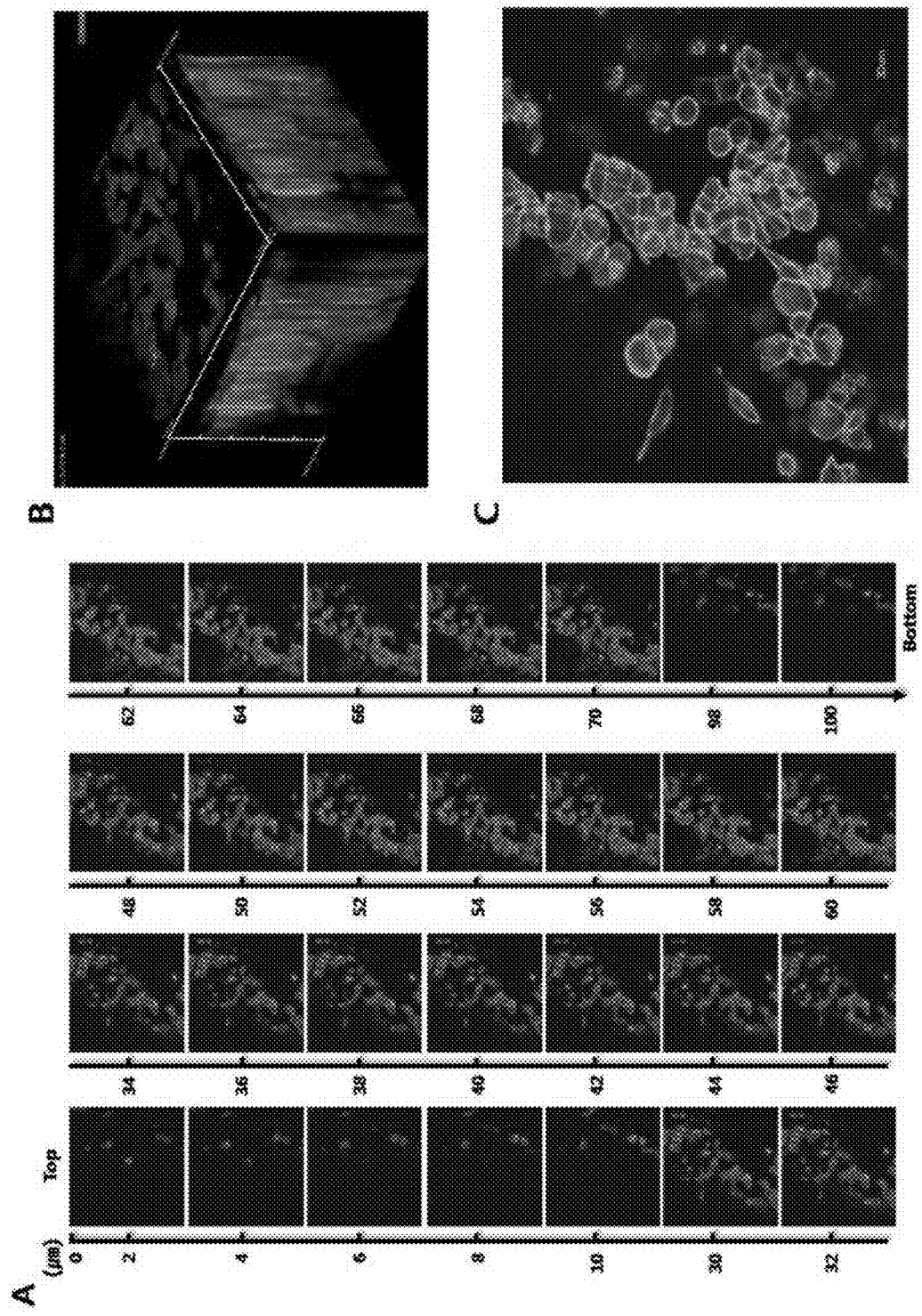
[FIGURE 19]

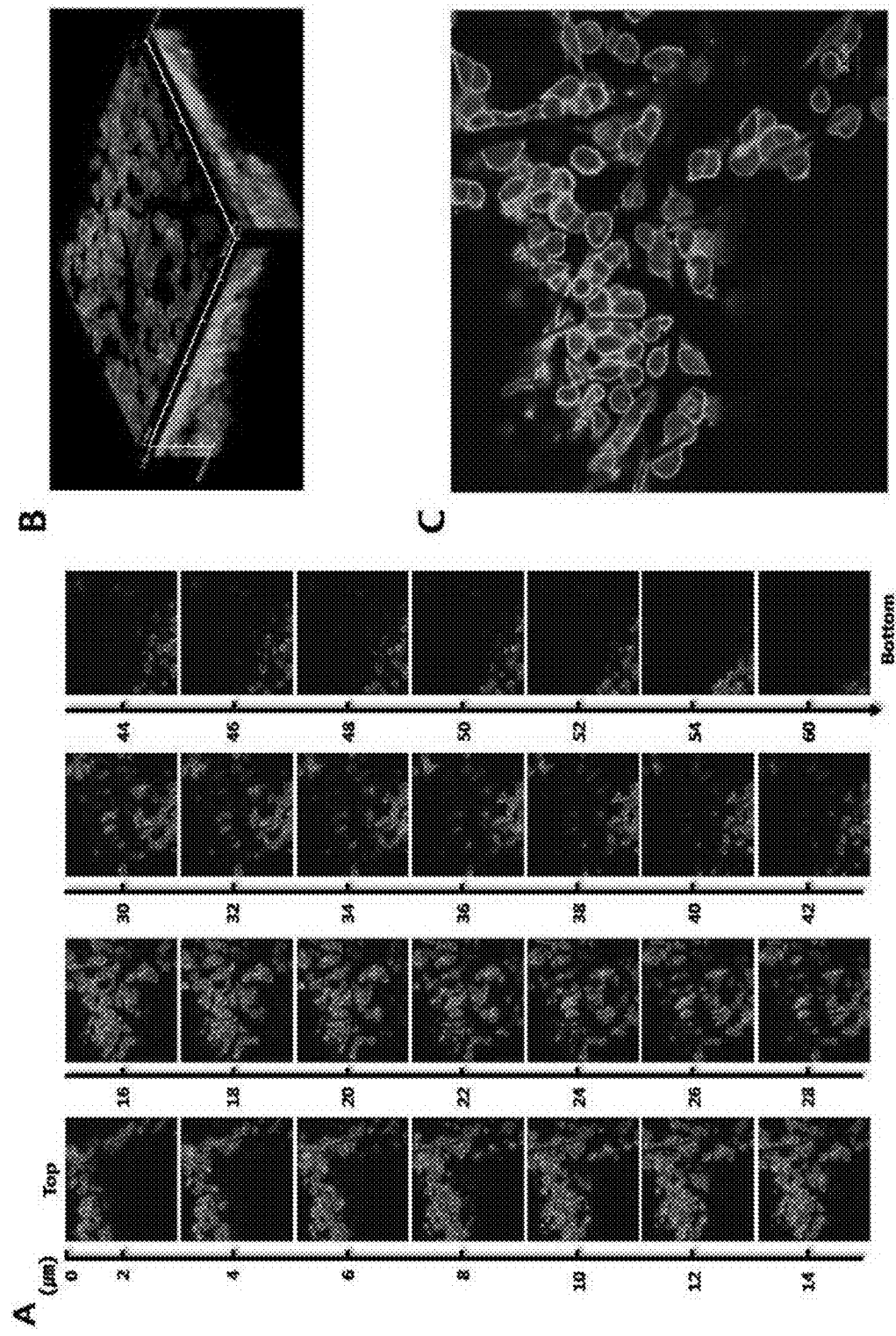
[FIGURE 20]

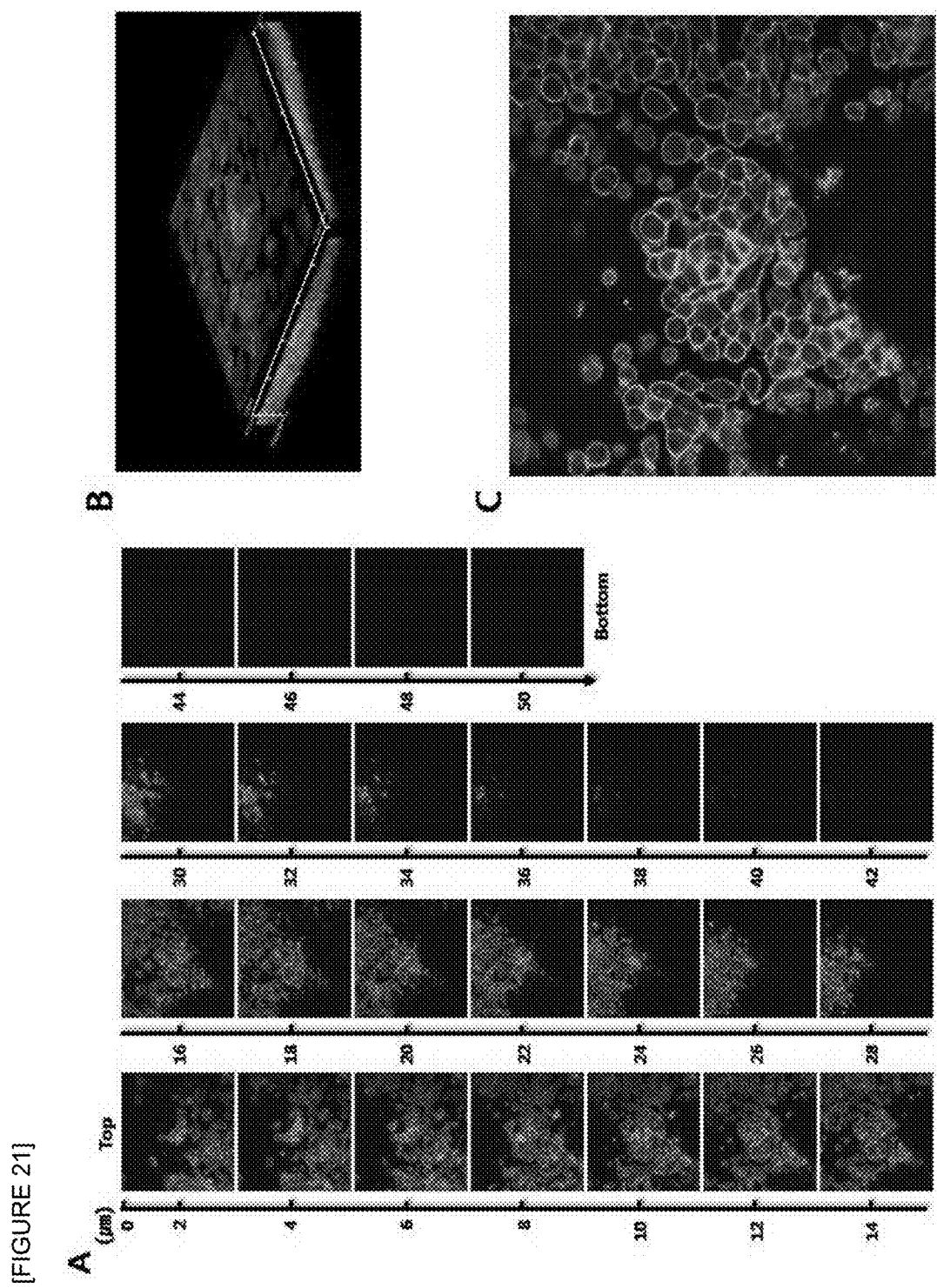
[FIGURE 21]

[FIGURE 22]
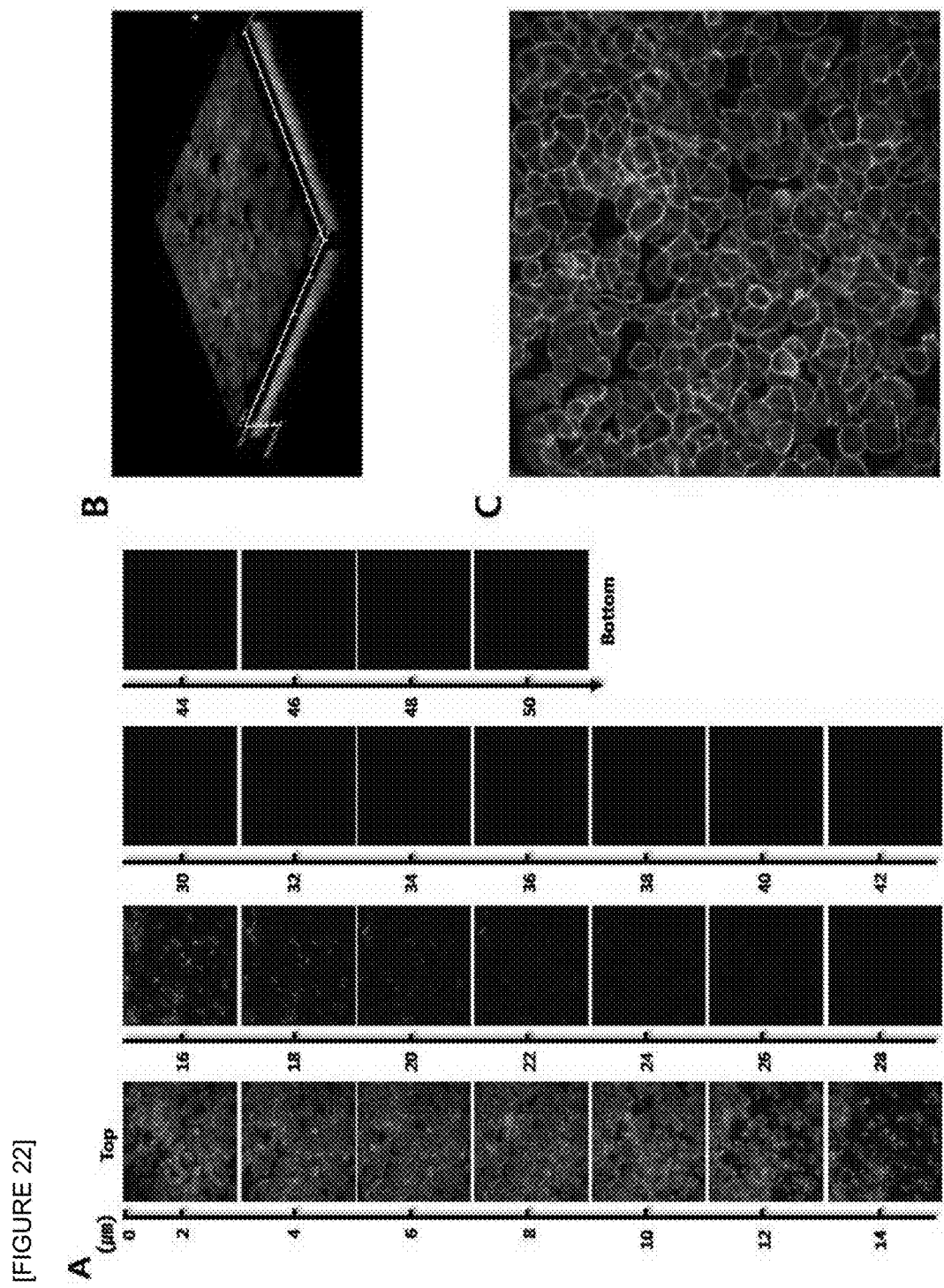

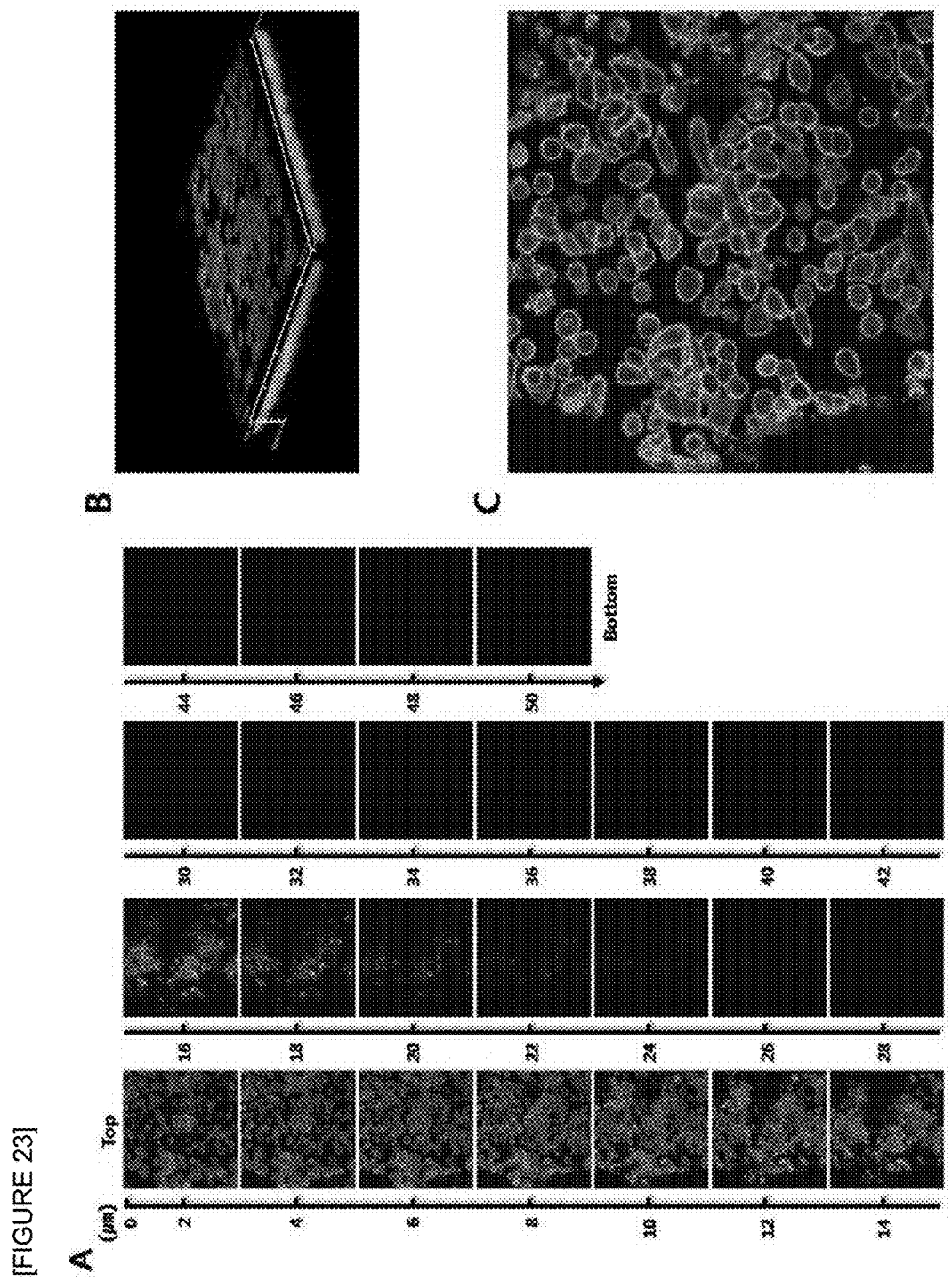
[FIGURE 23]

[FIGURE 24]
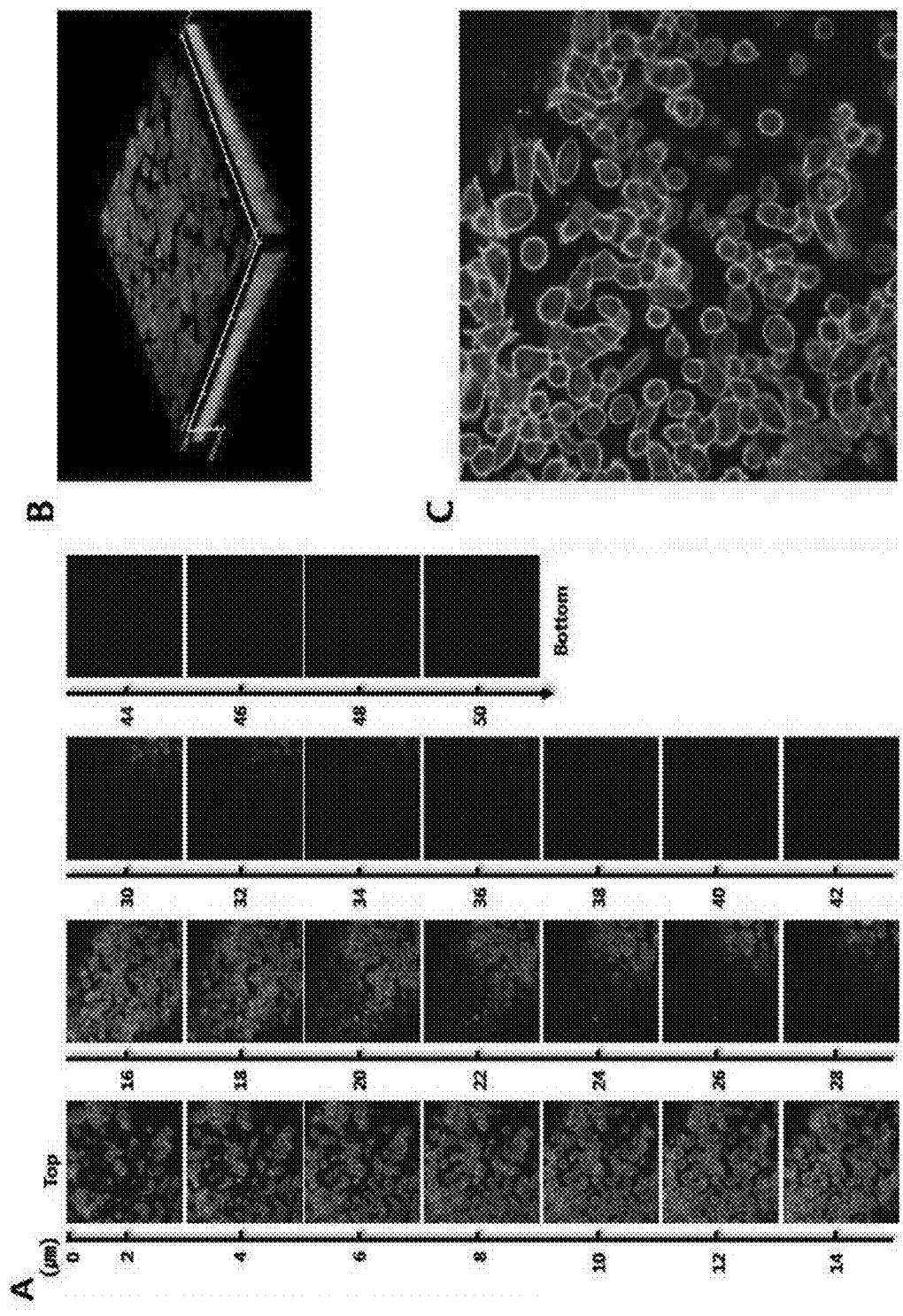

[FIGURE 25]
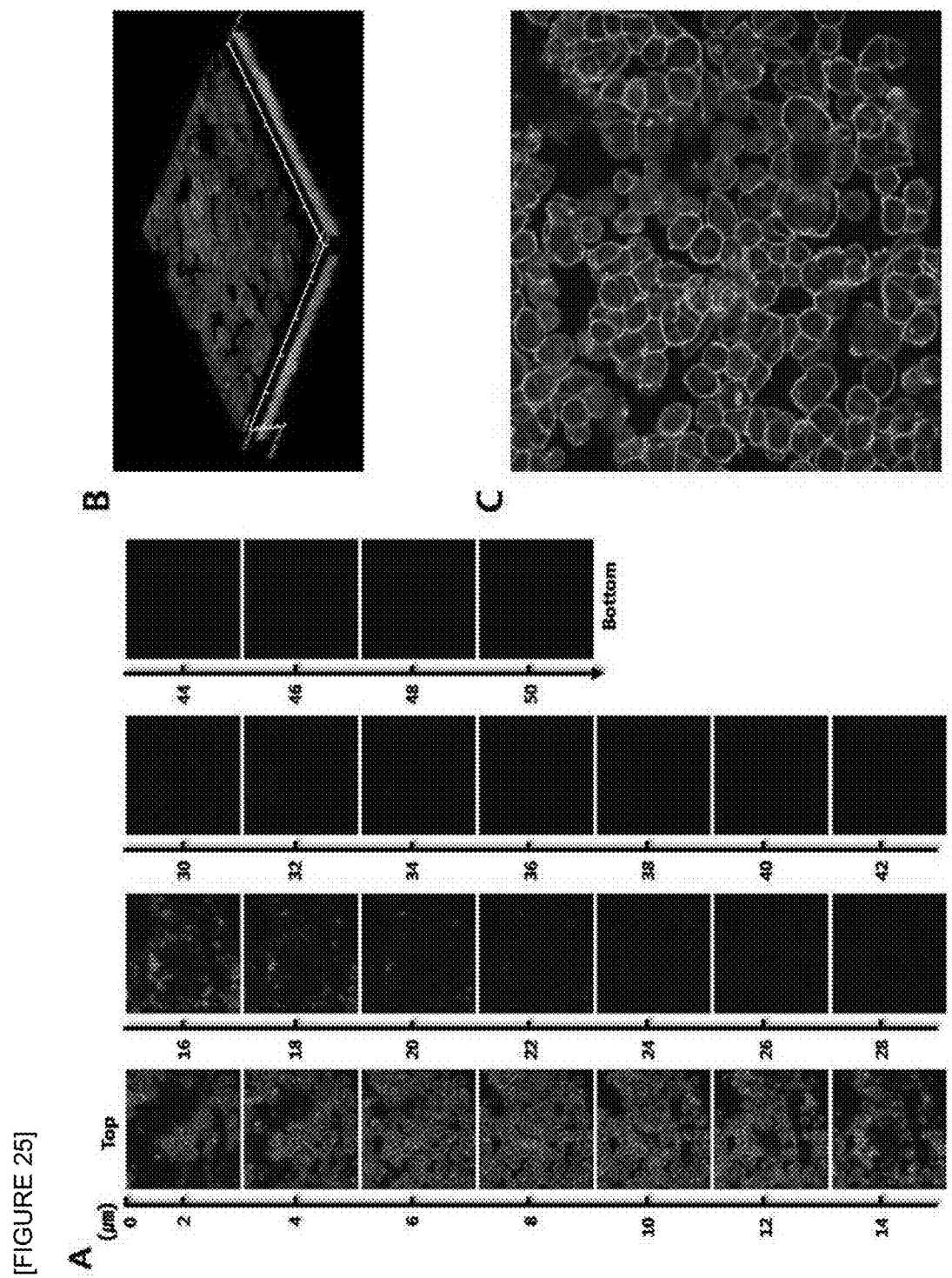

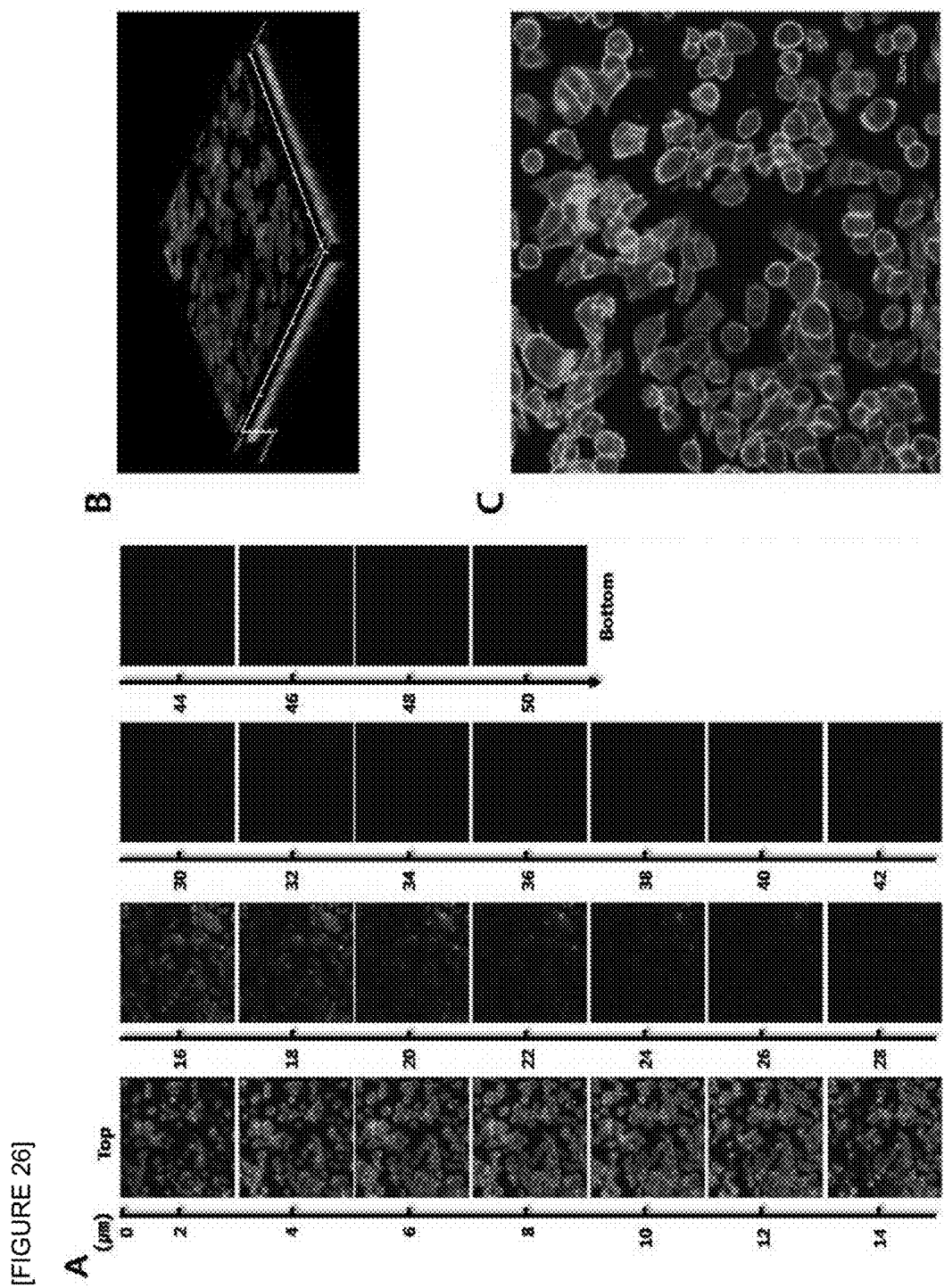
[FIGURE 26]

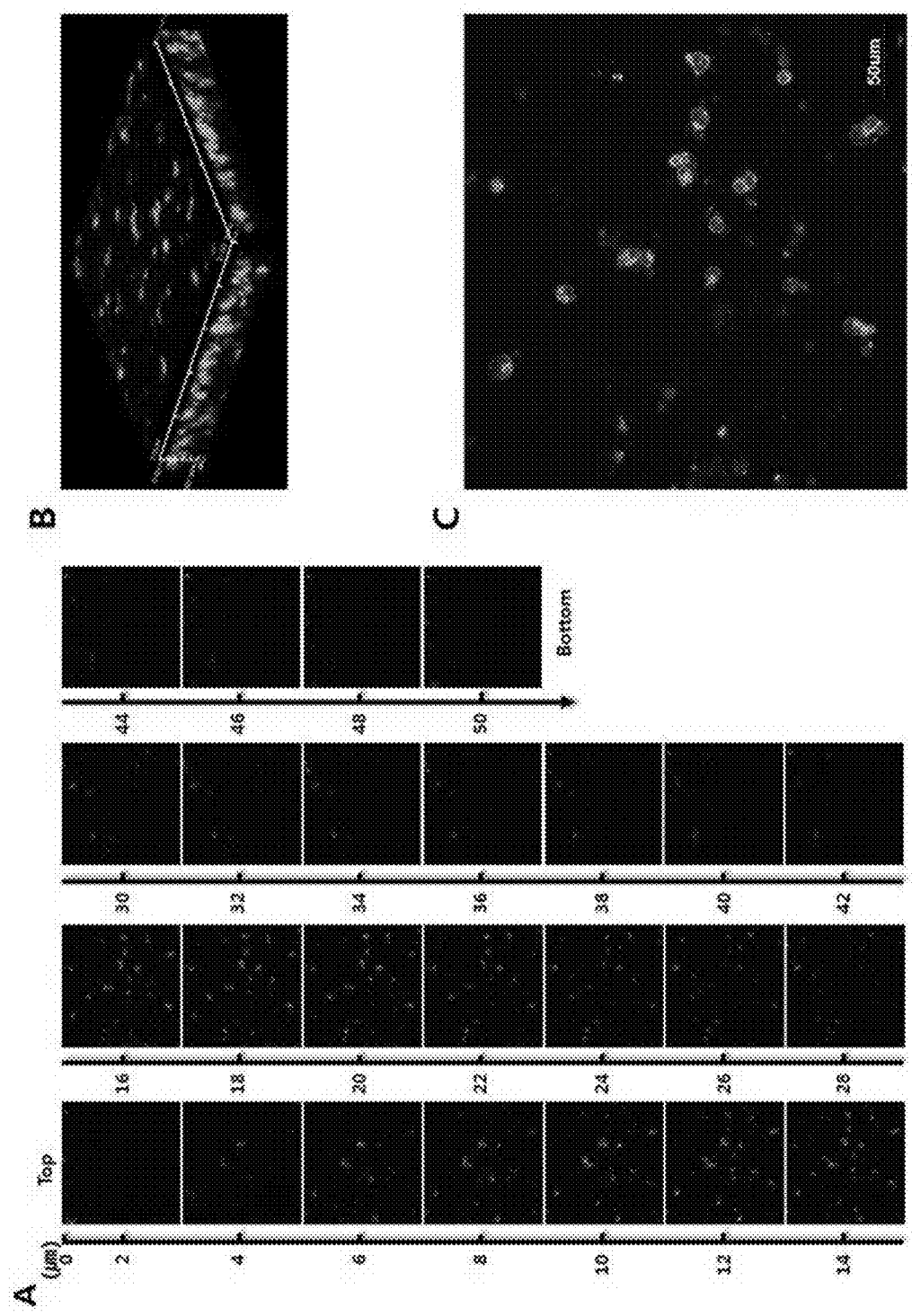
[FIGURE 27]

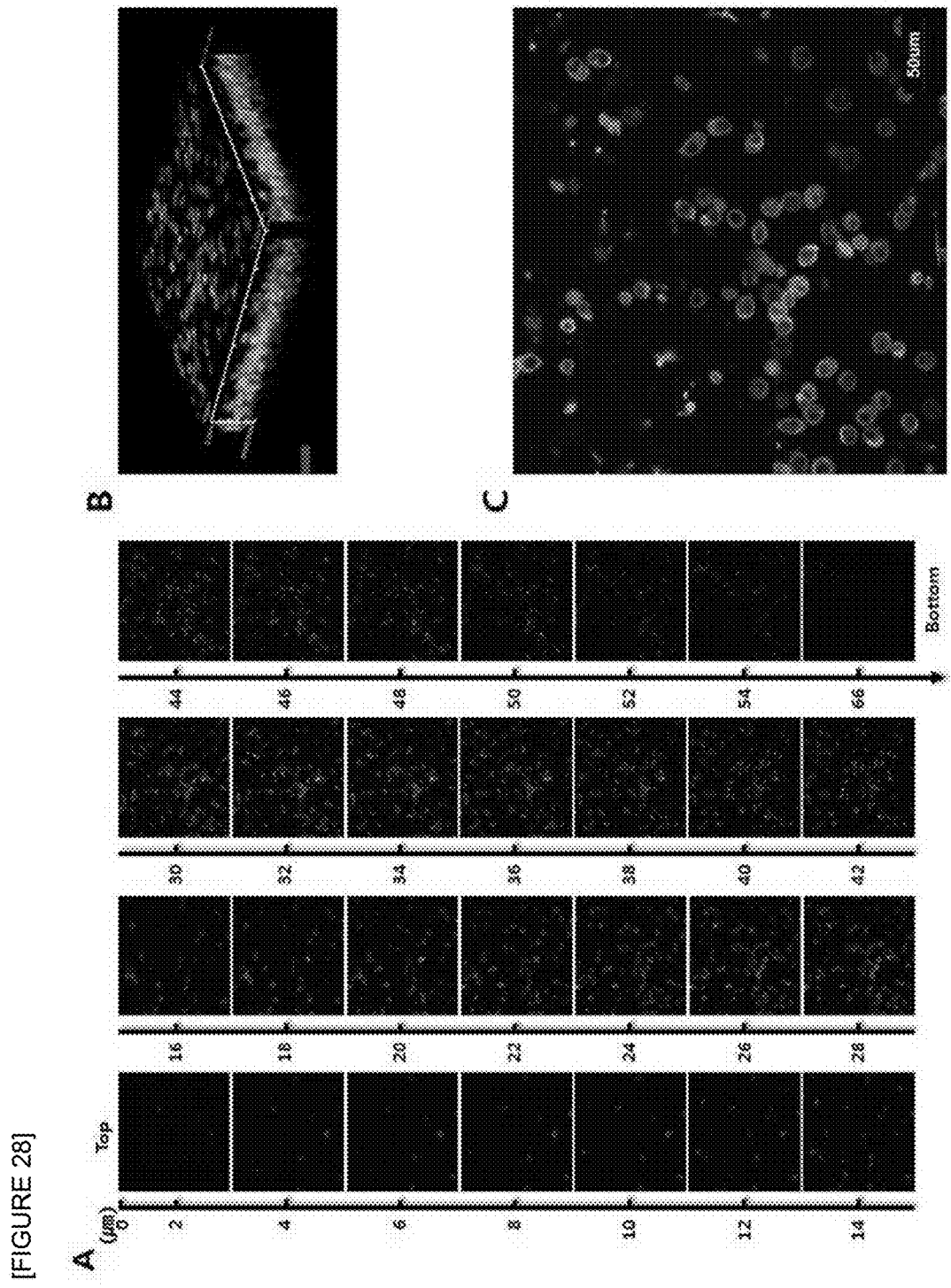
[FIGURE 28]

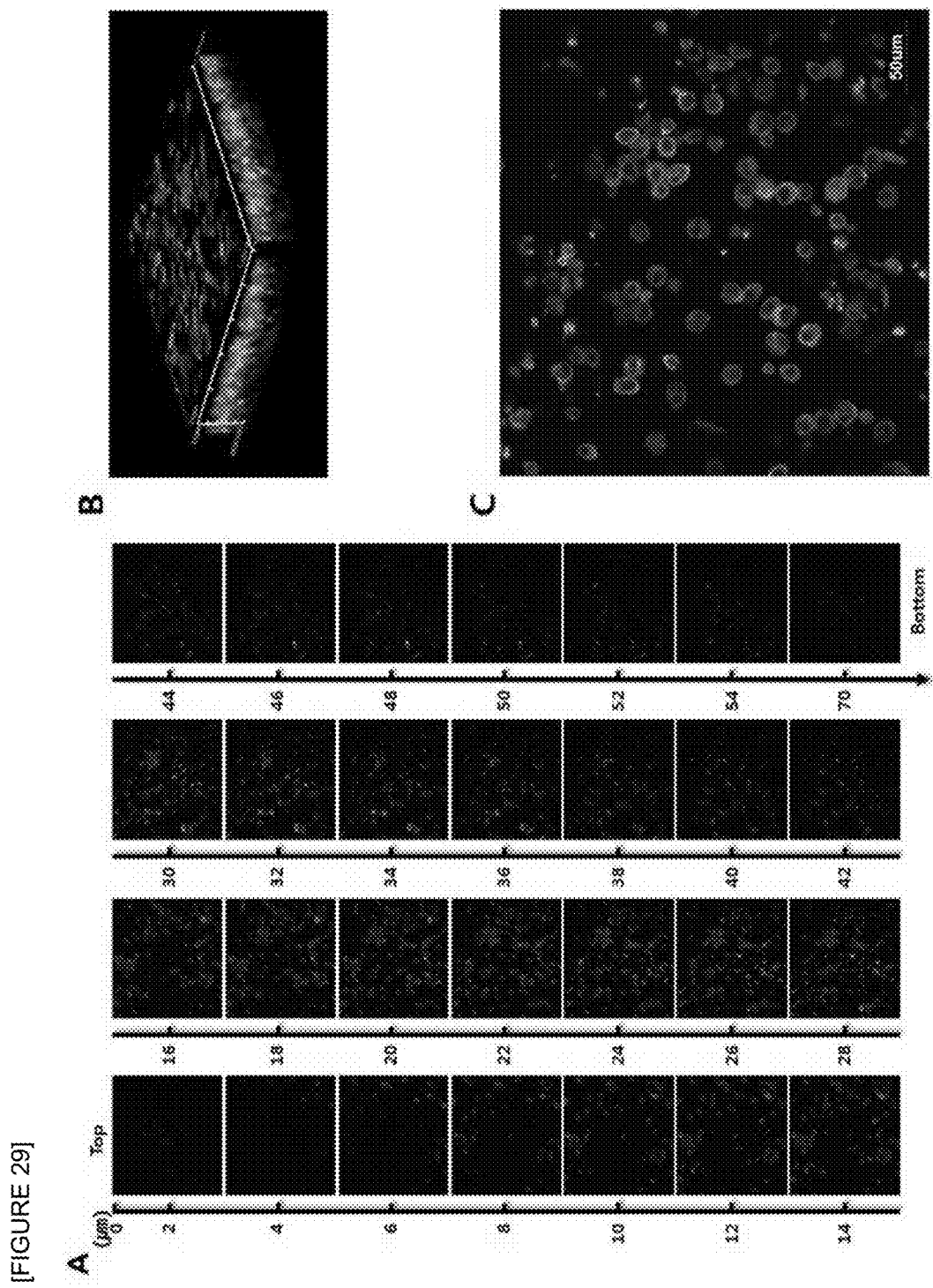
[FIGURE 29]

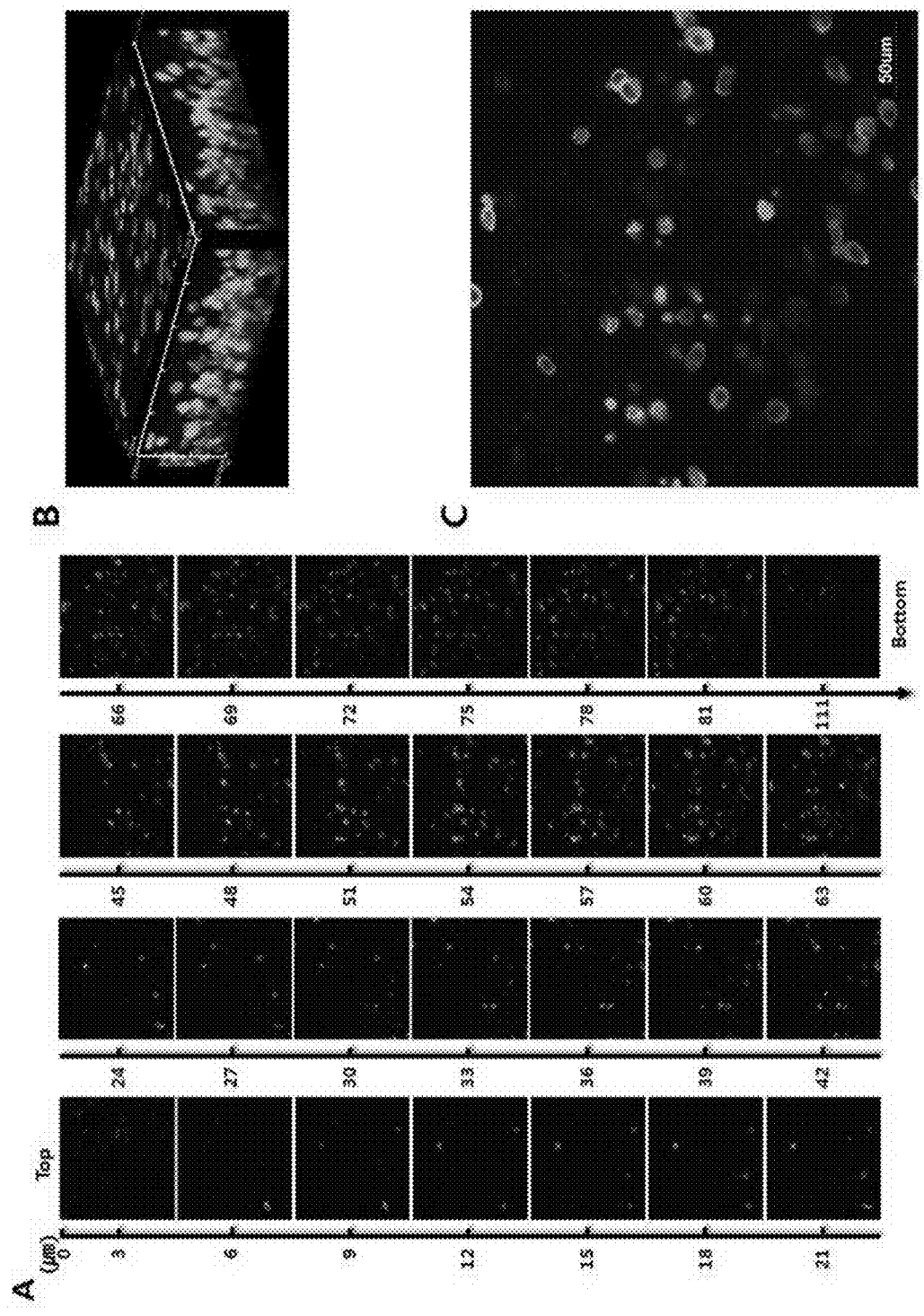
[FIGURE 30]

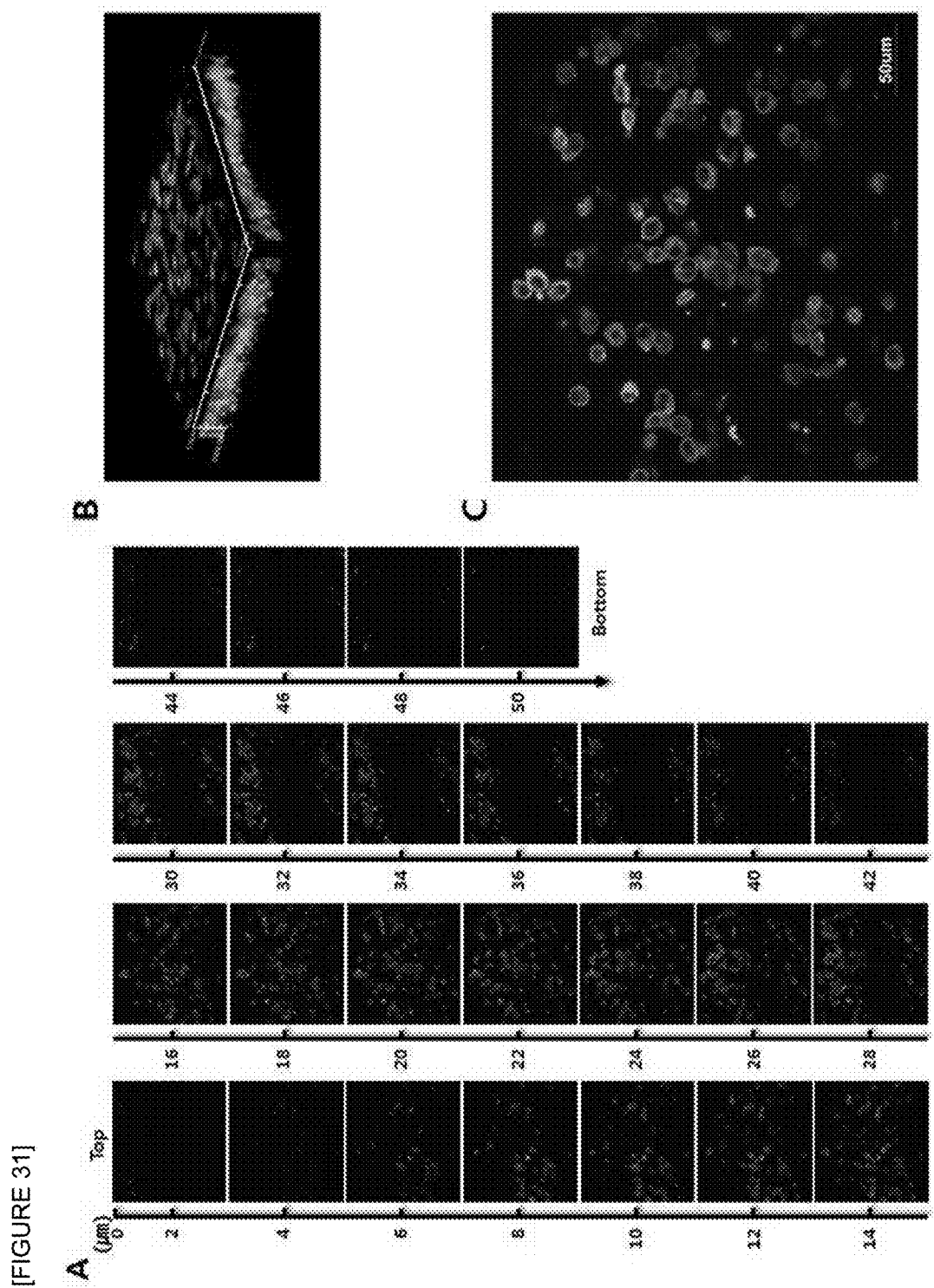
[FIGURE 31]

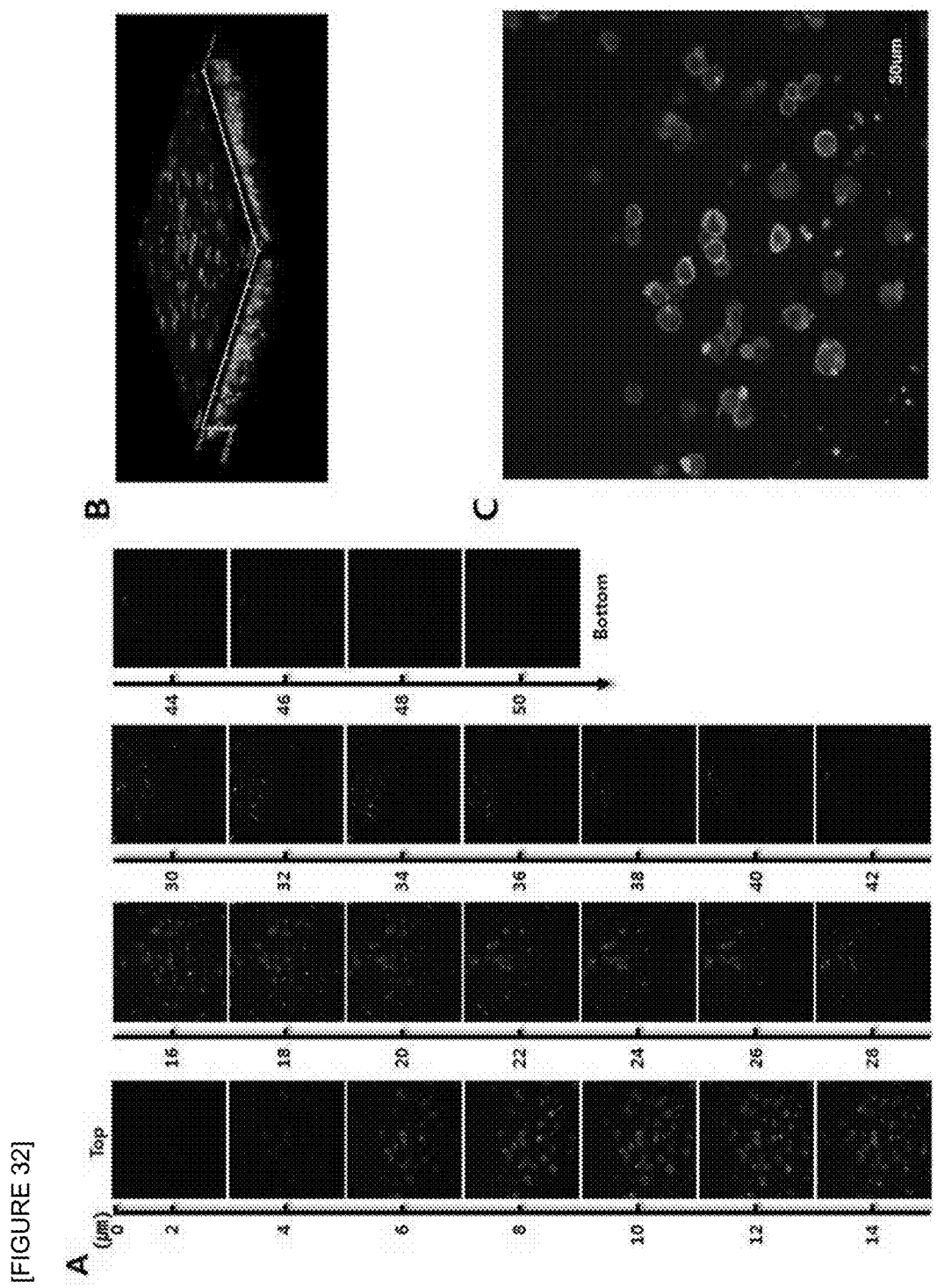
[FIGURE 32]

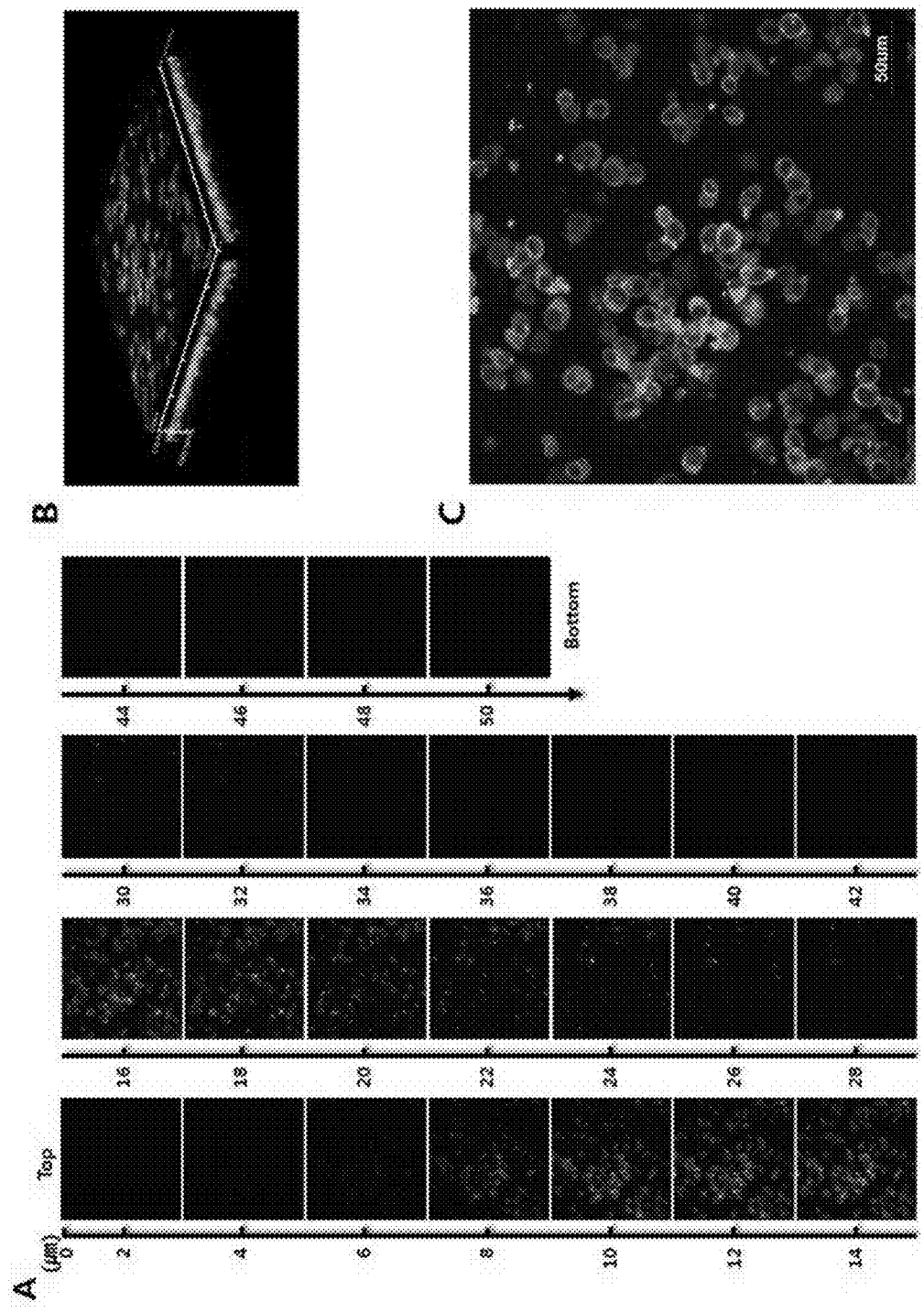
[FIGURE 33]

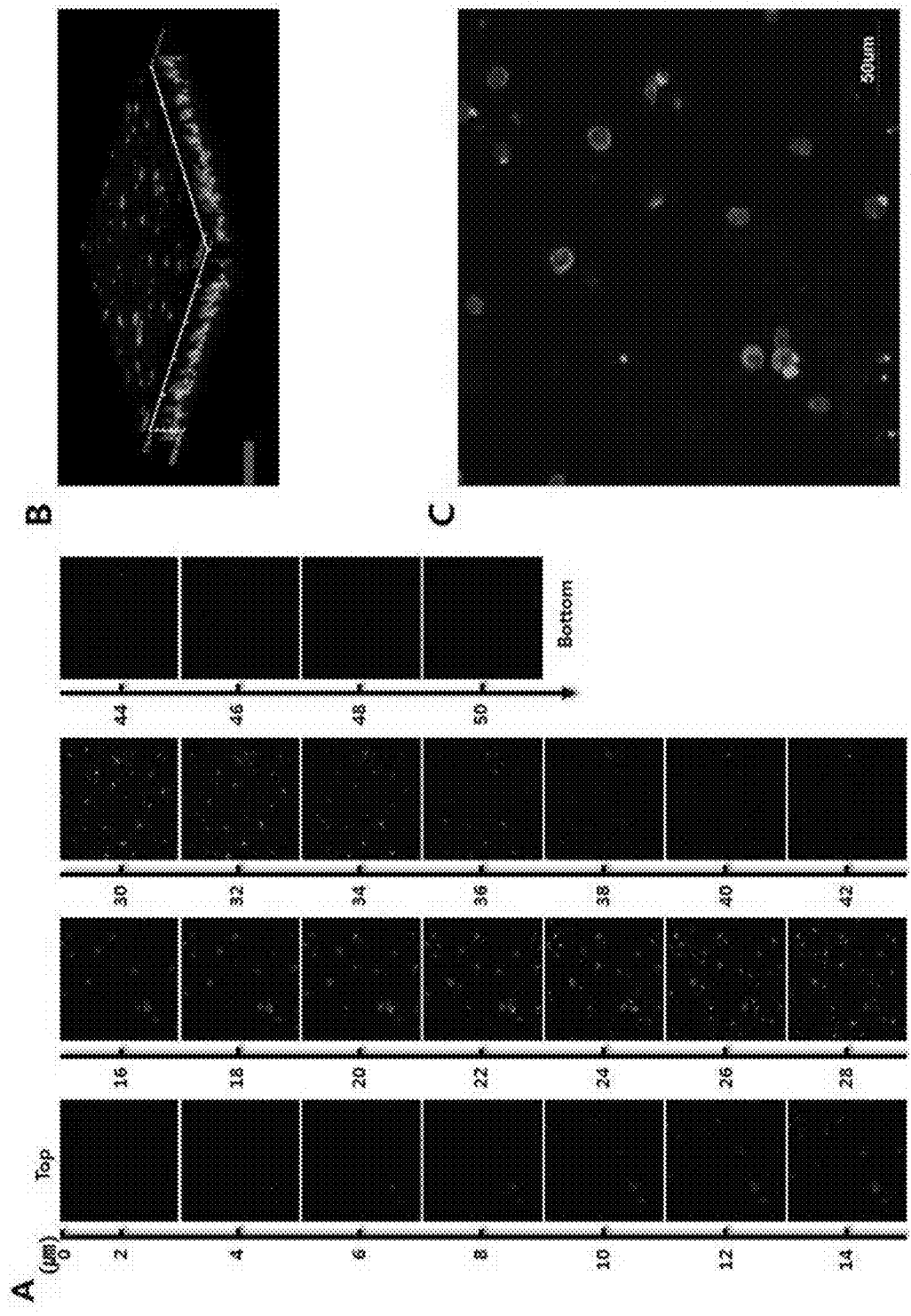
[FIGURE 34]

[FIGURE 35]
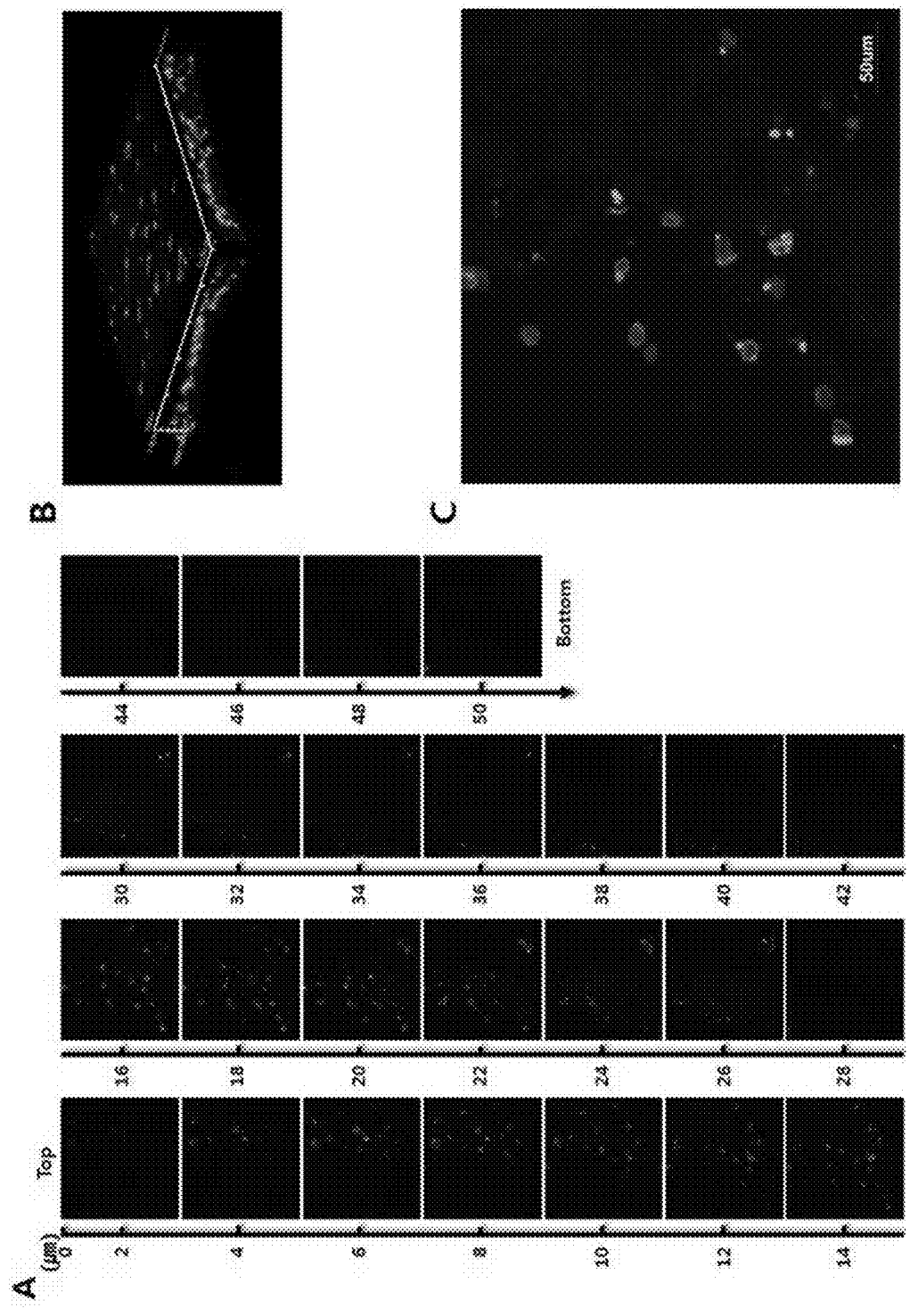

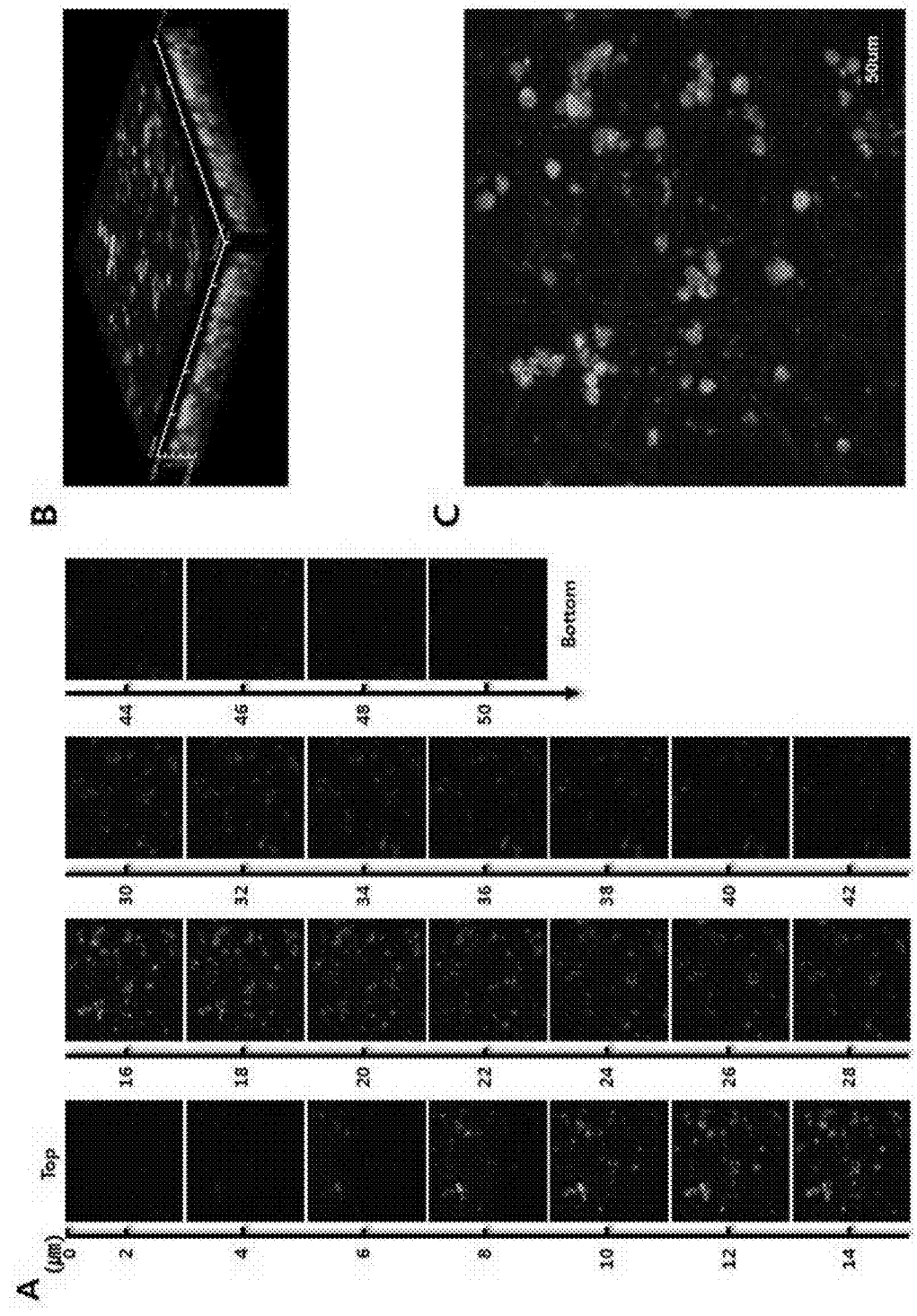
[FIGURE 36]

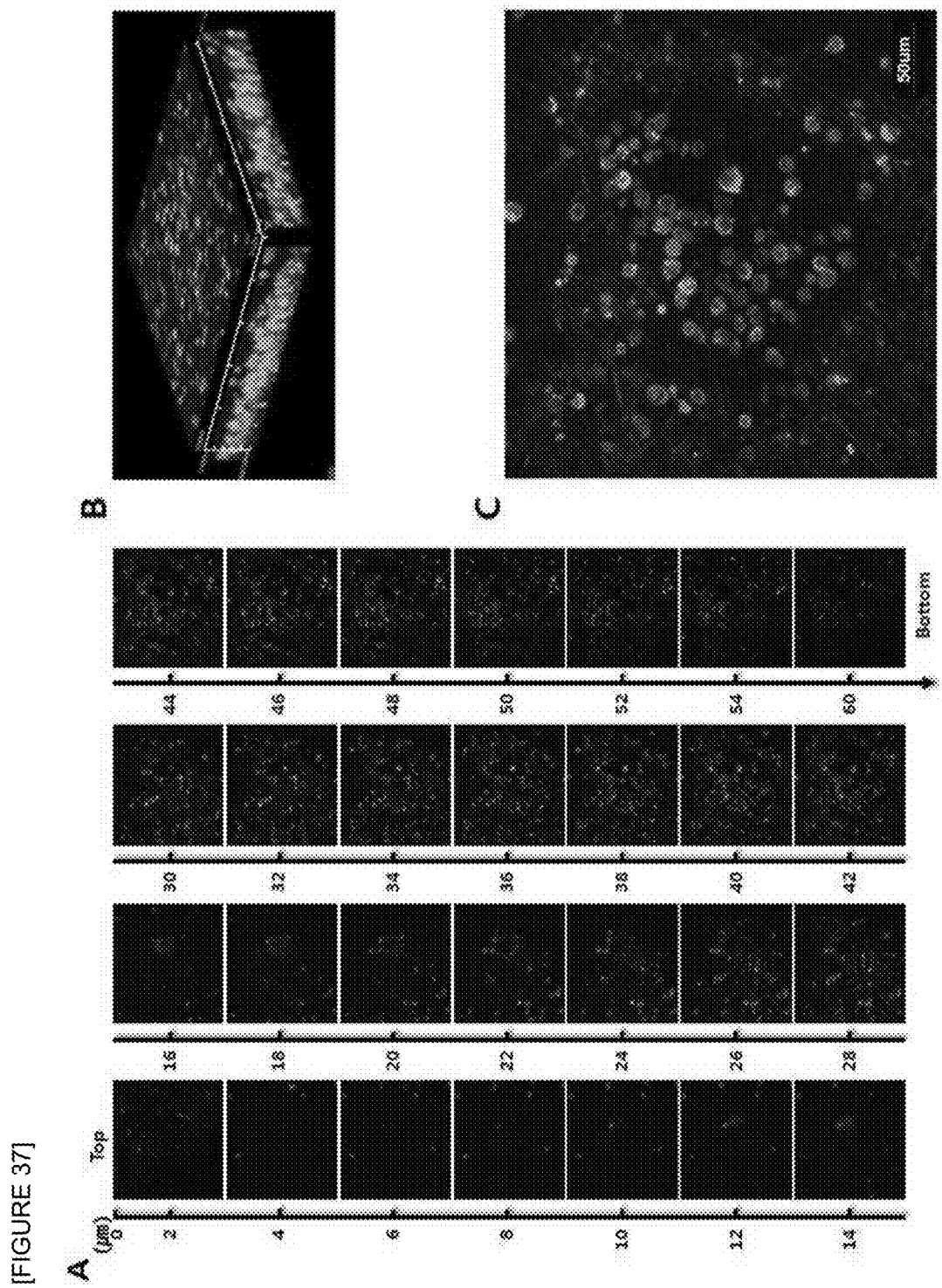
[FIGURE 37]

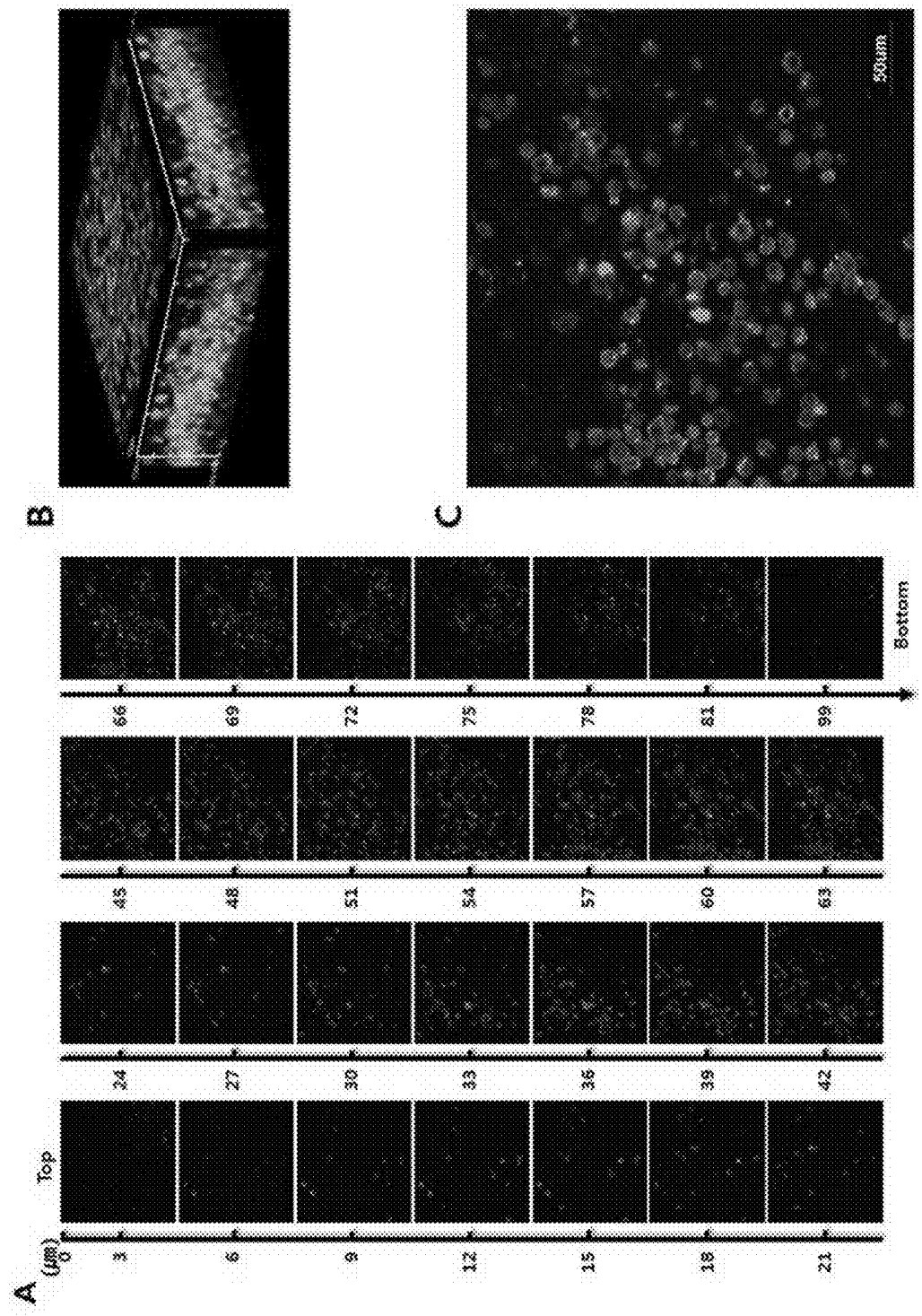
[FIGURE 38]

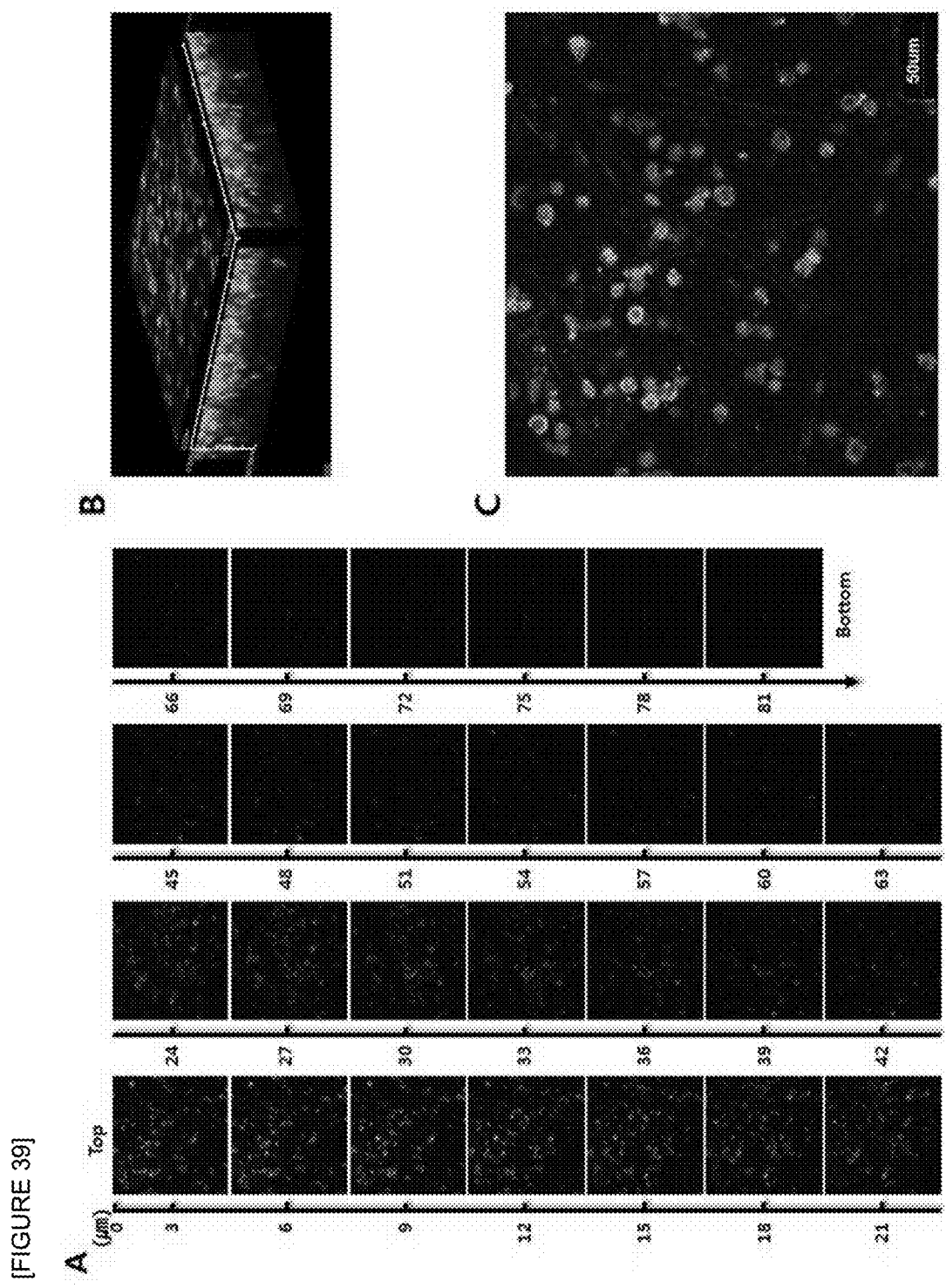
[FIGURE 39]

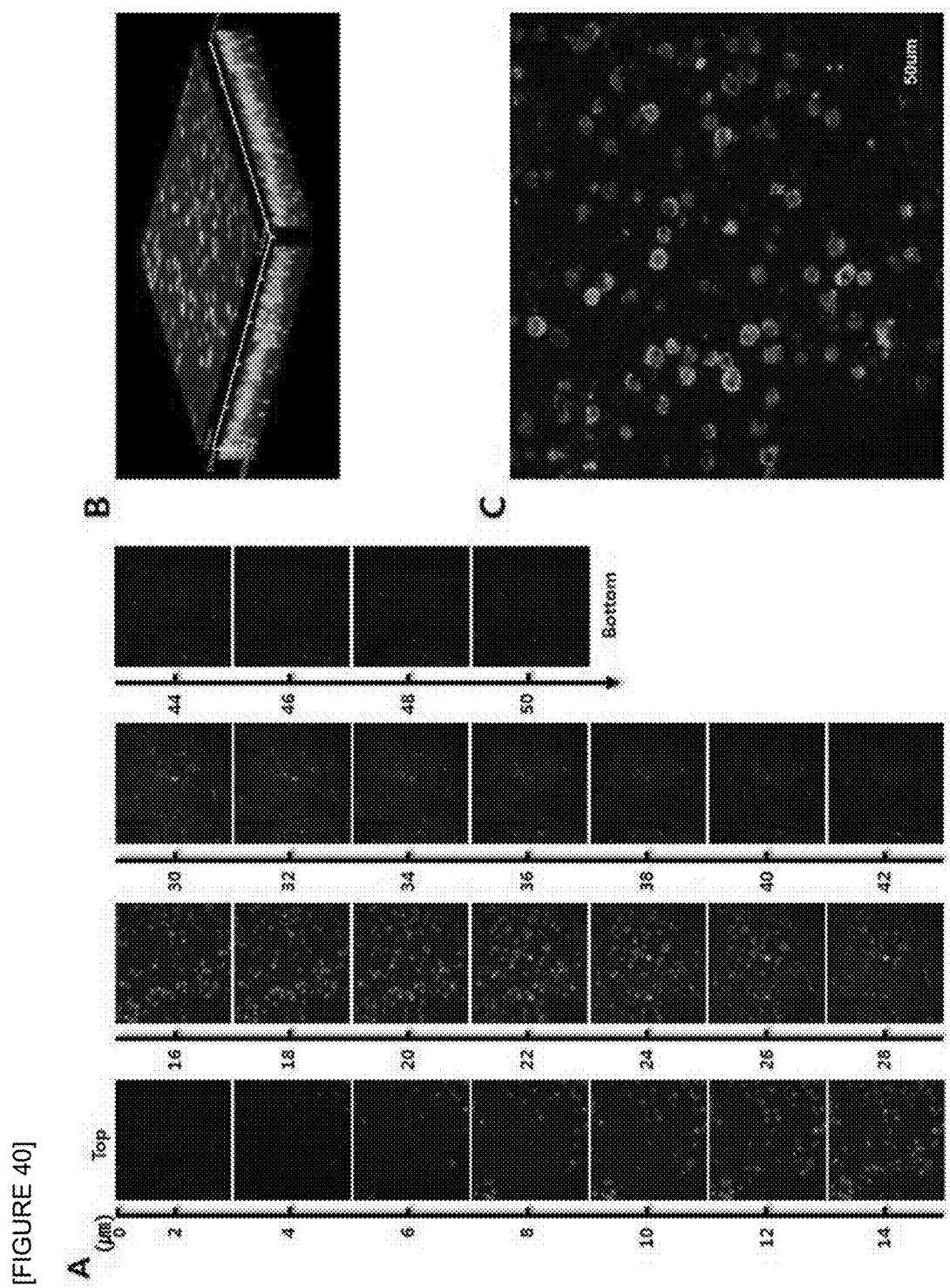
[FIGURE 40]

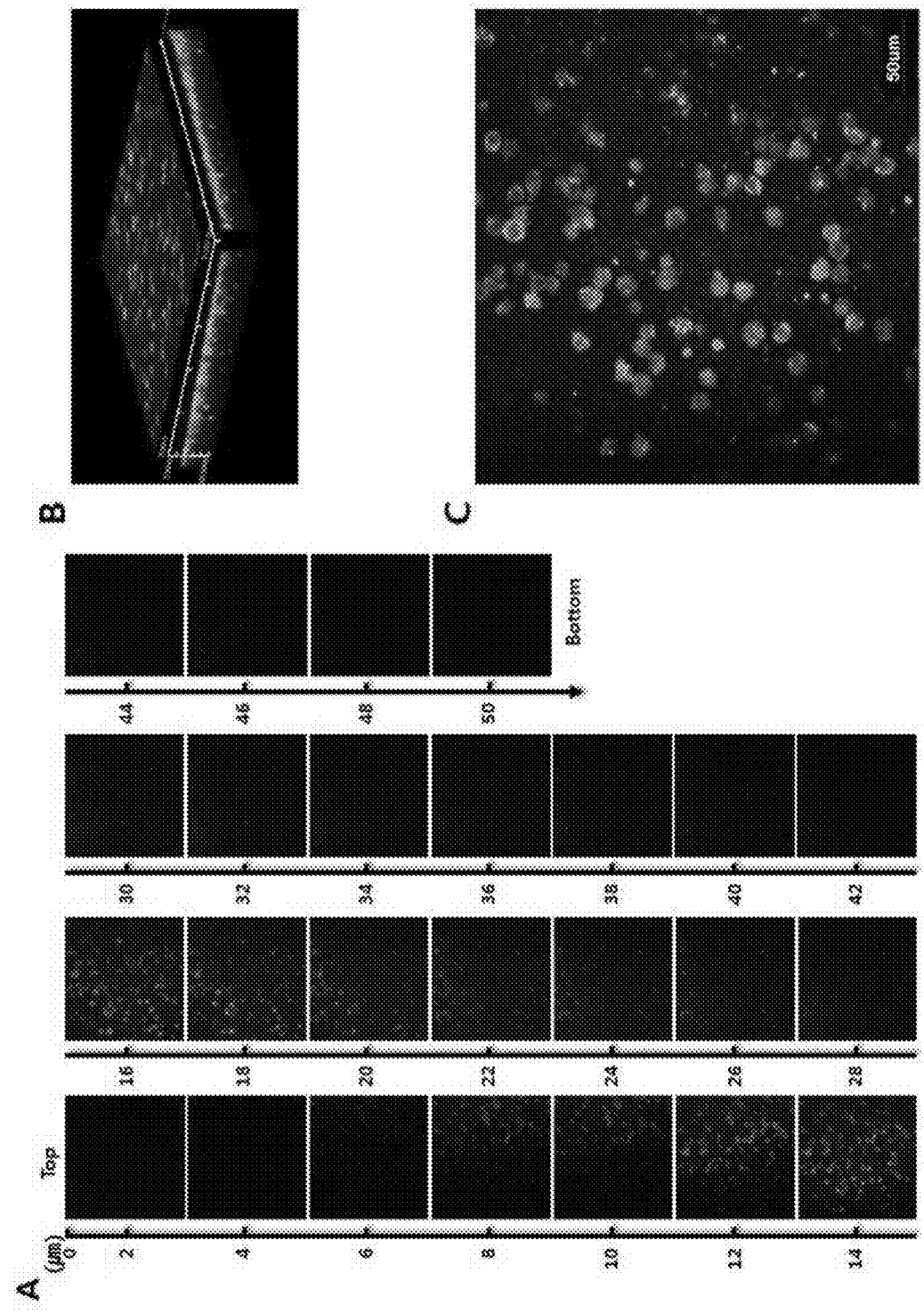
[FIGURE 41]

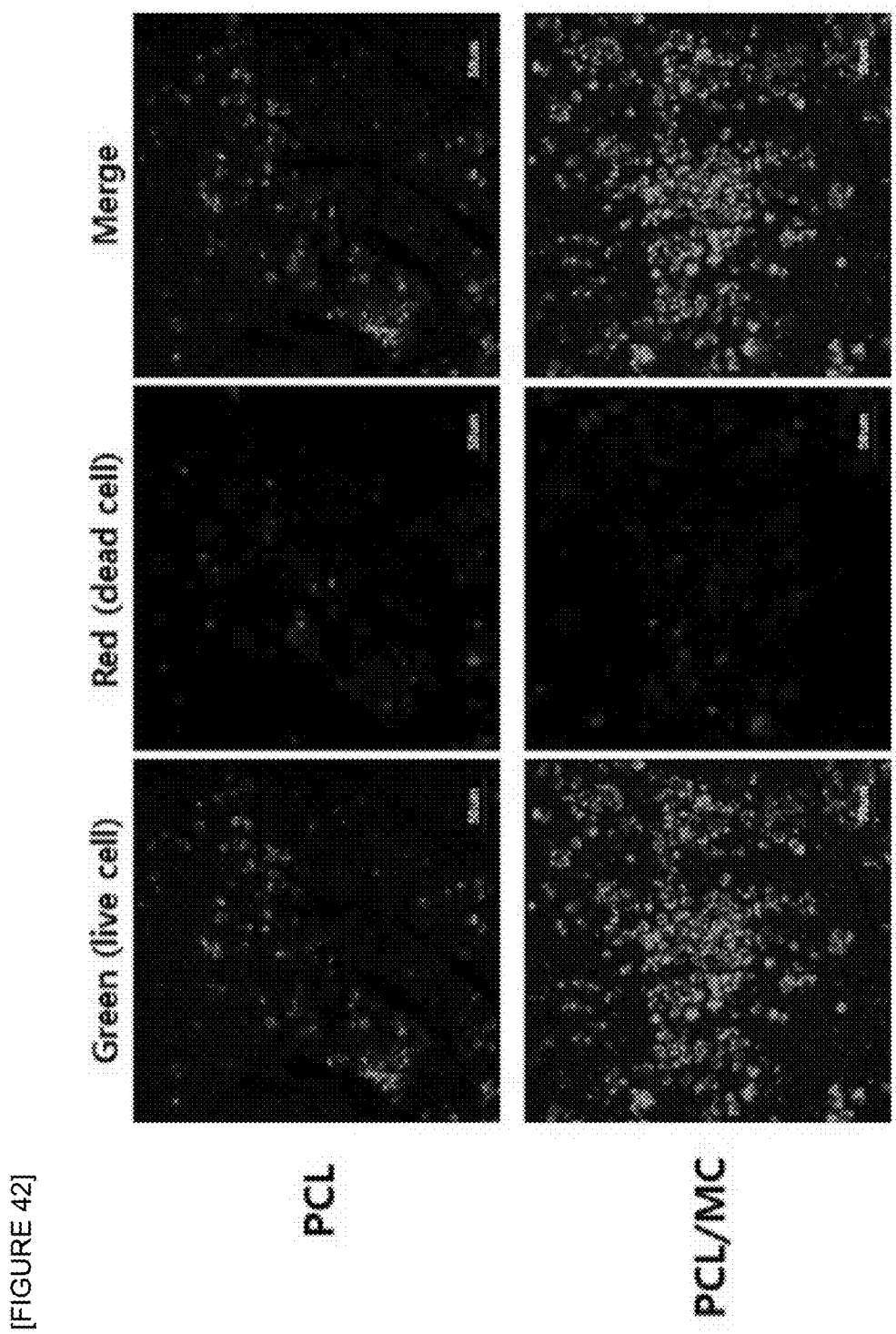
[FIGURE 42]

[FIGURE 43]
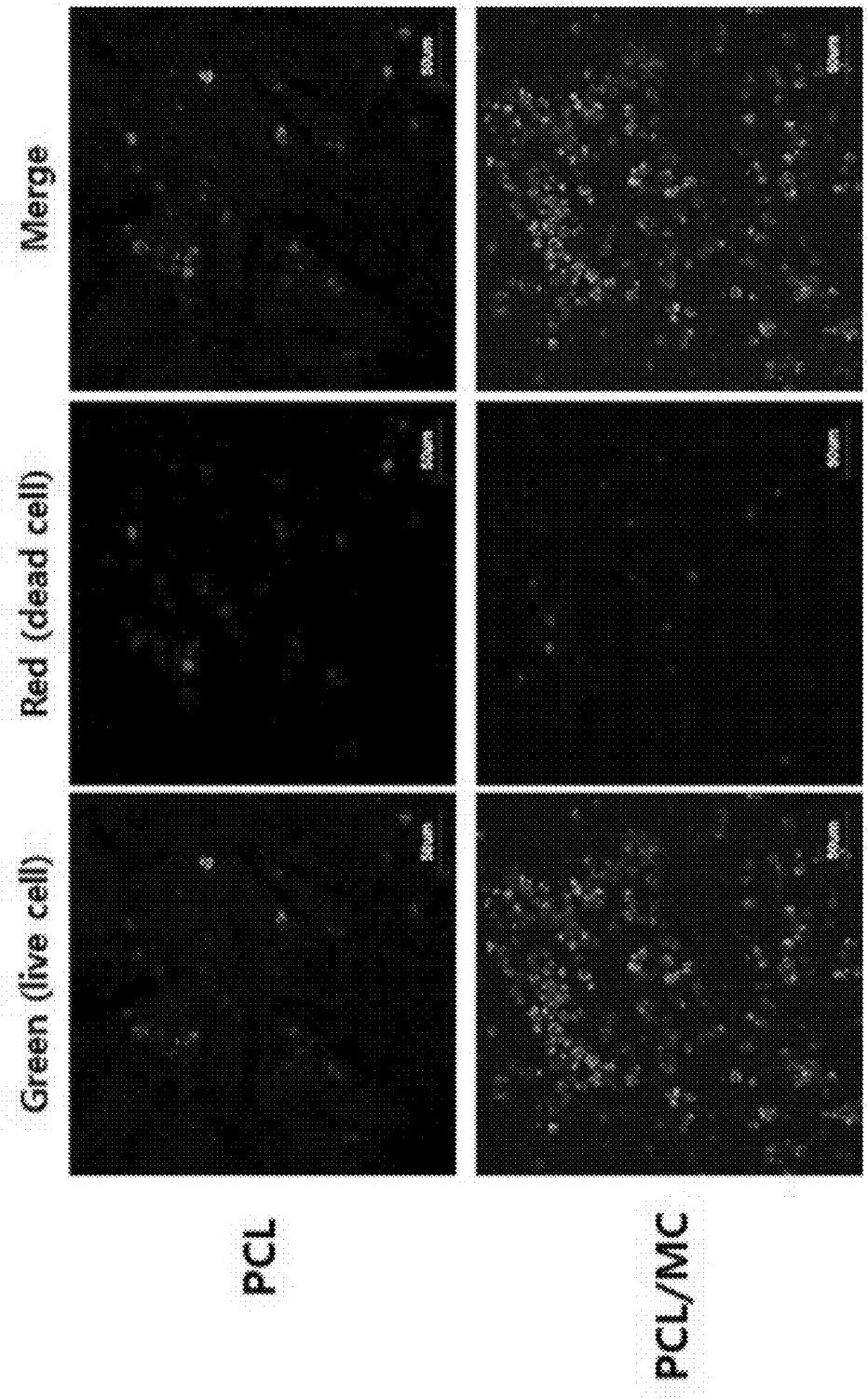

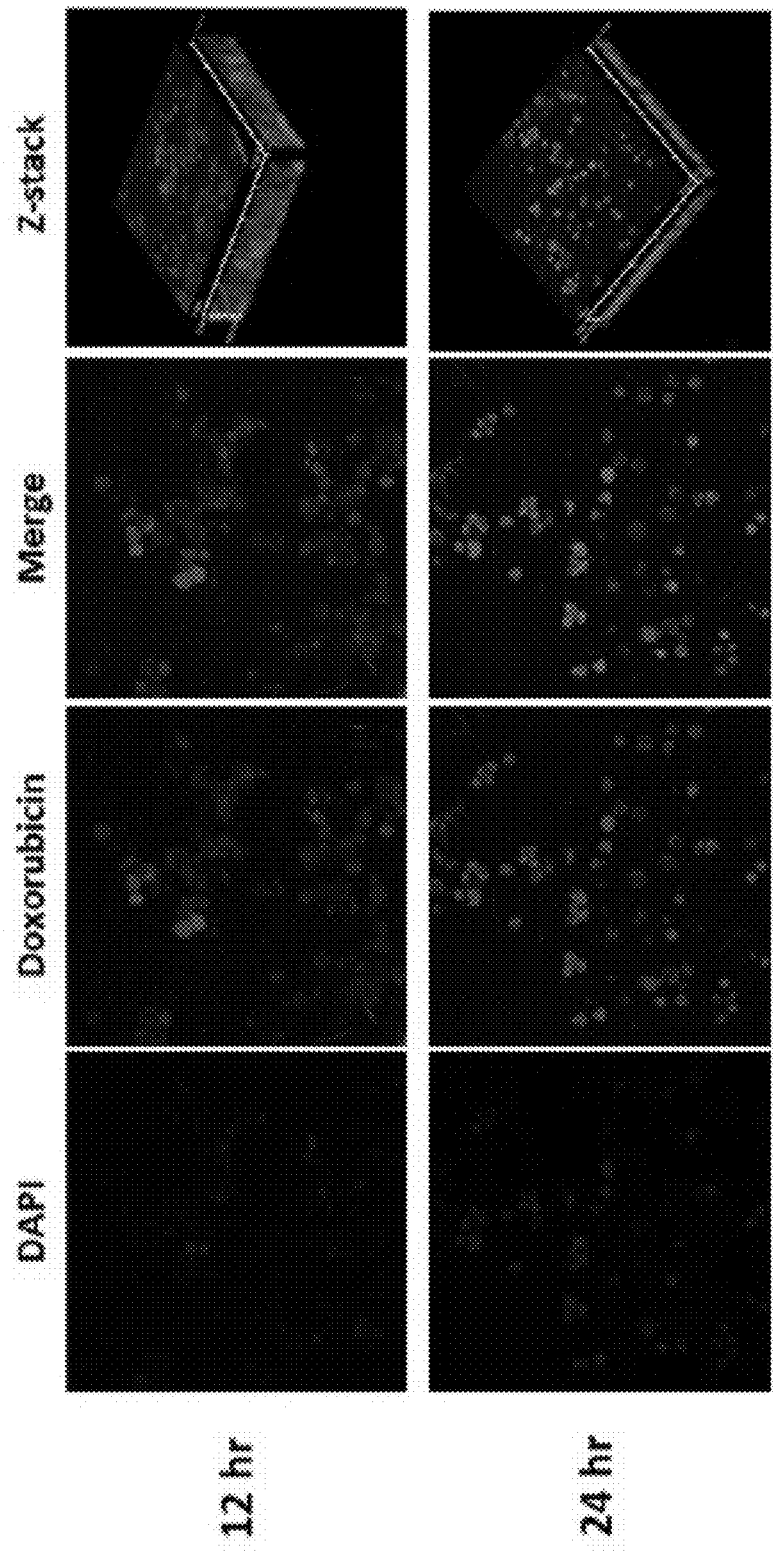
[FIGURE 44]

[FIGURE 45]
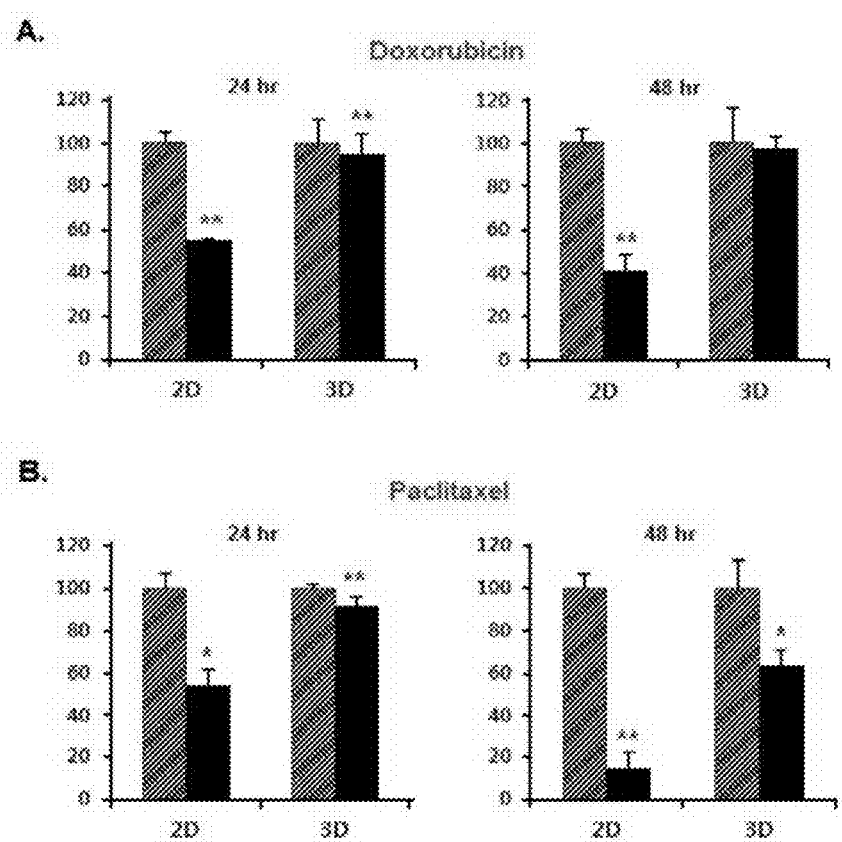

[FIGURE 46]
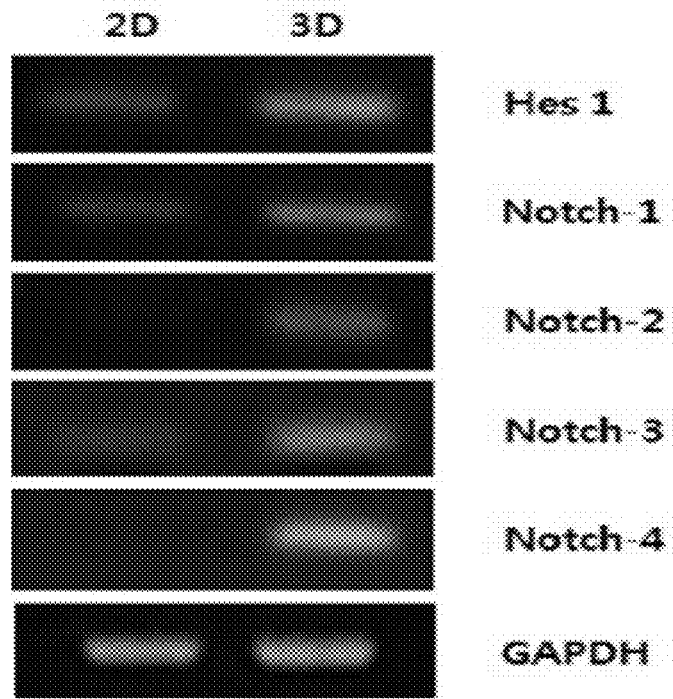
[FIGURE 47]
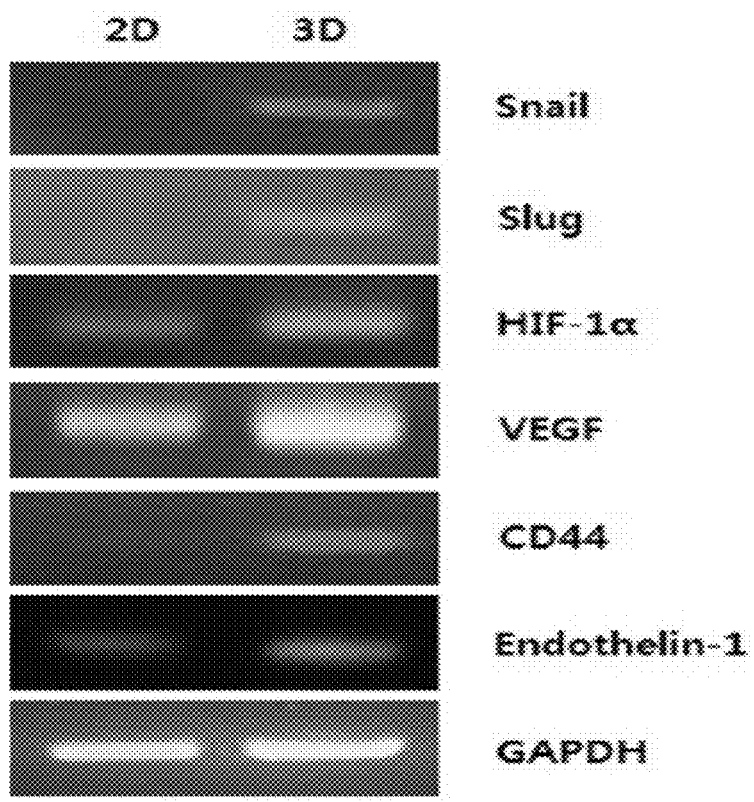

[FIGURE 48]
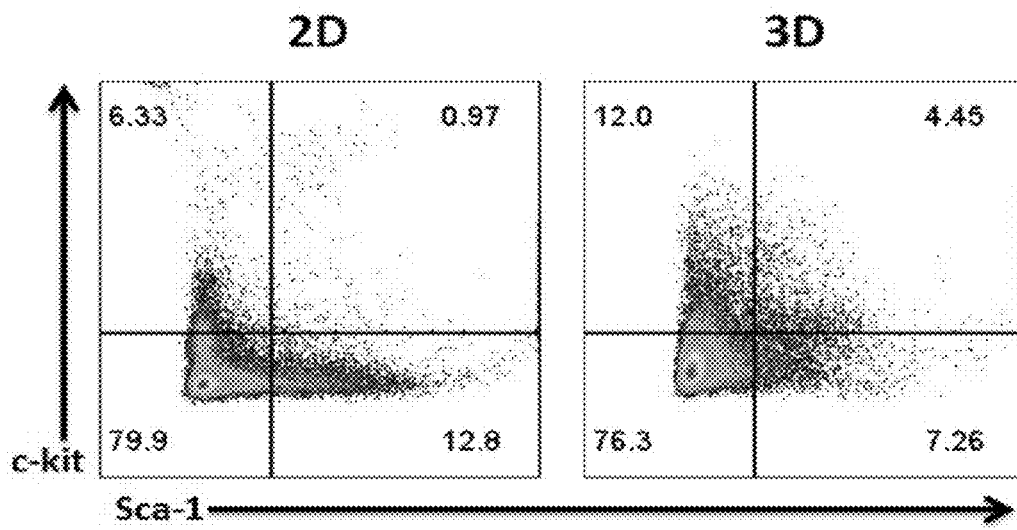
[FIGURE 49]
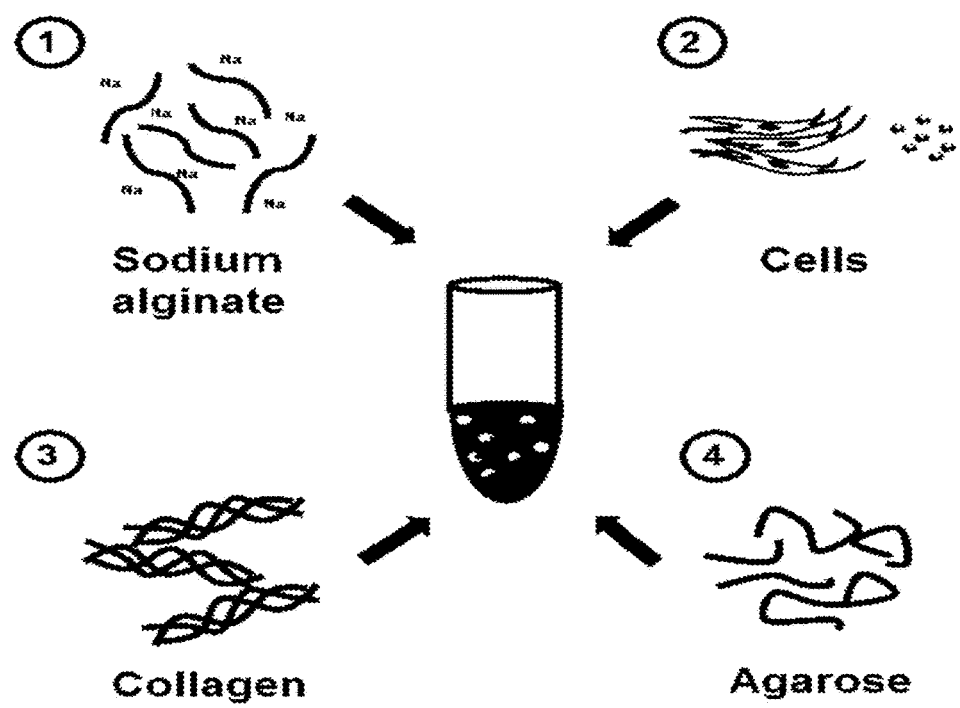

[FIGURE 50]
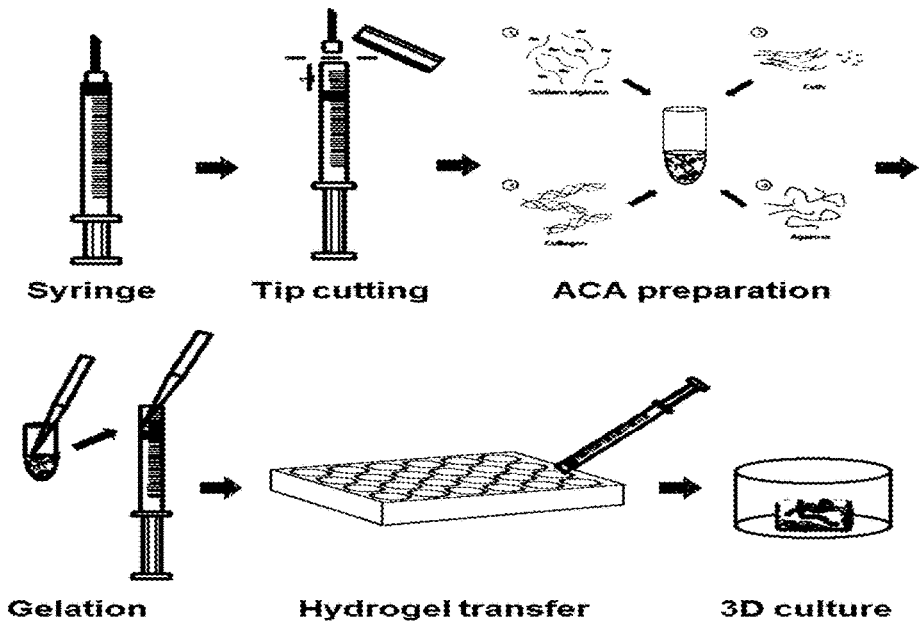
[FIGURE 51]
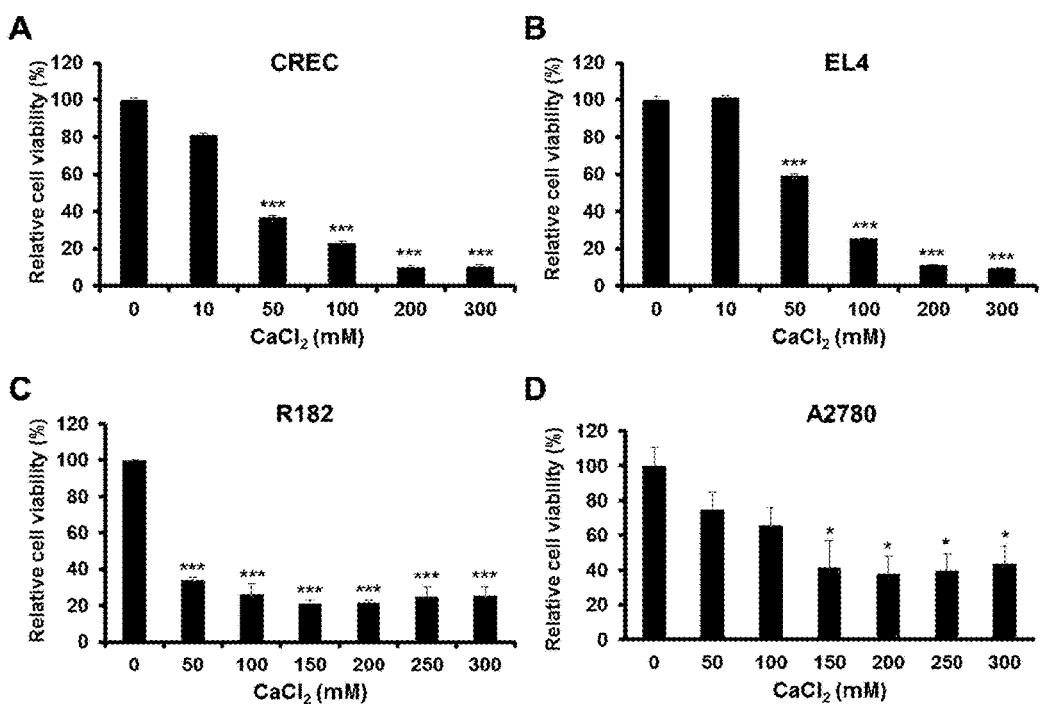

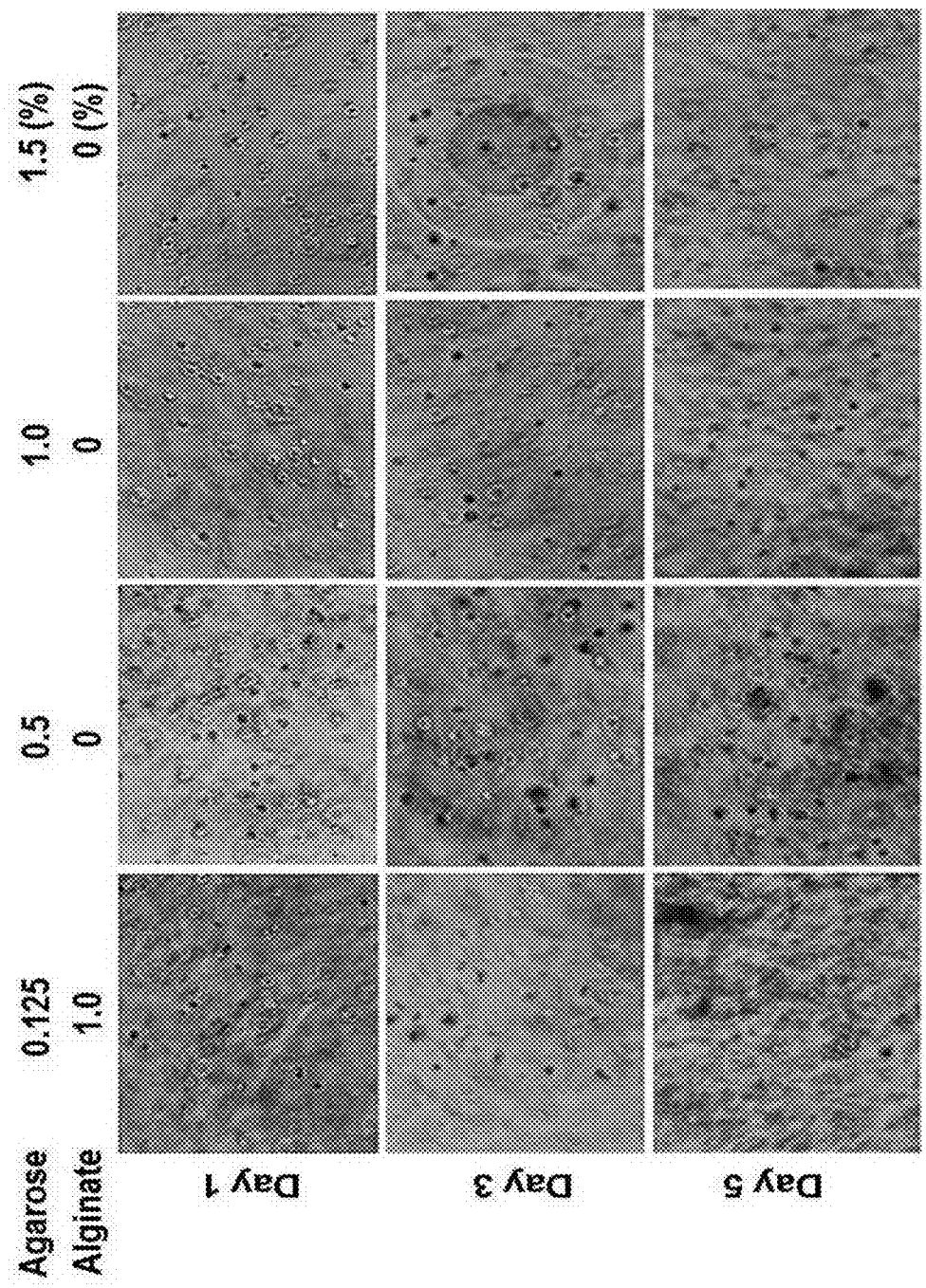
[FIGURE 52]

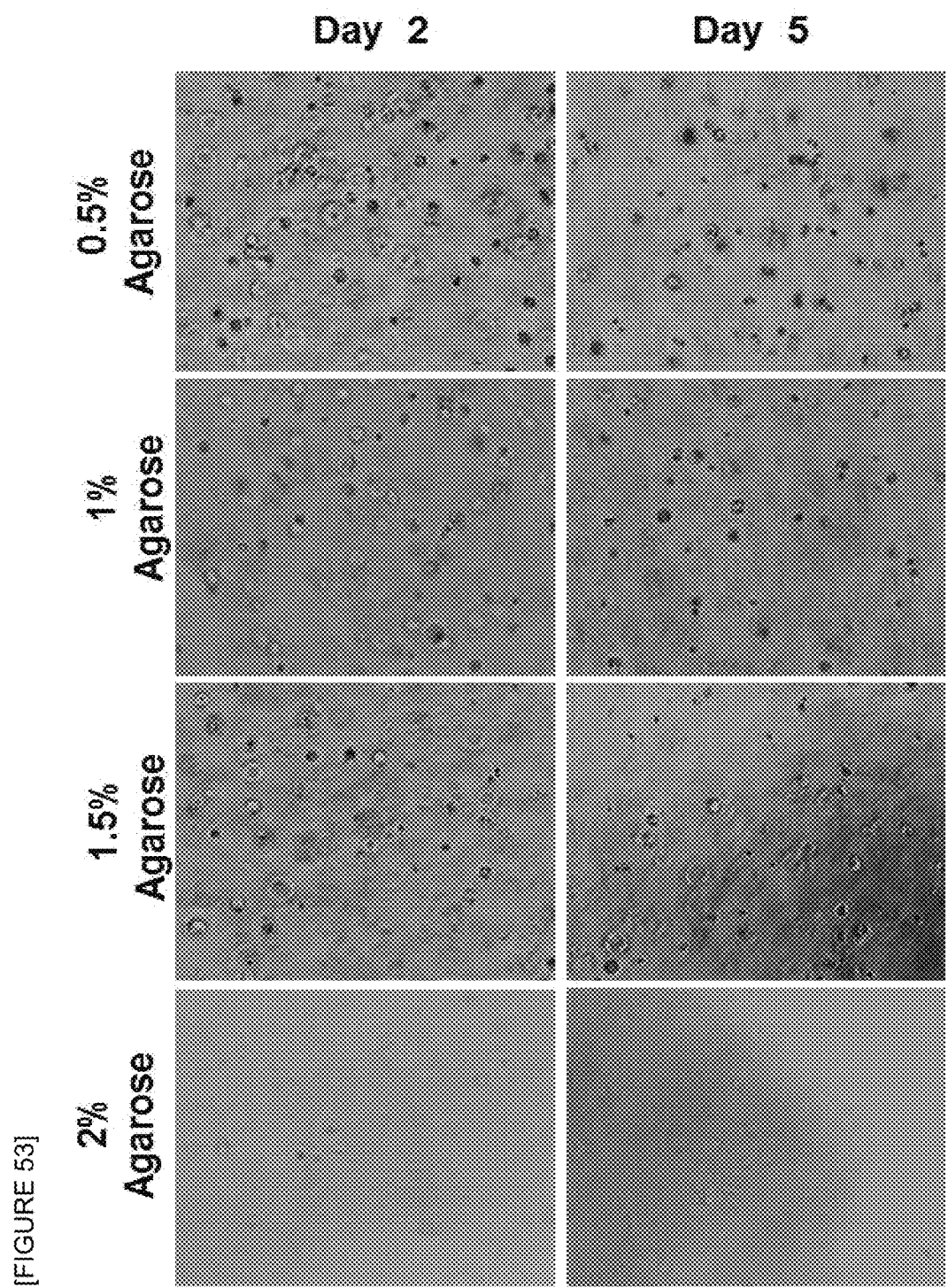
[FIGURE 53]

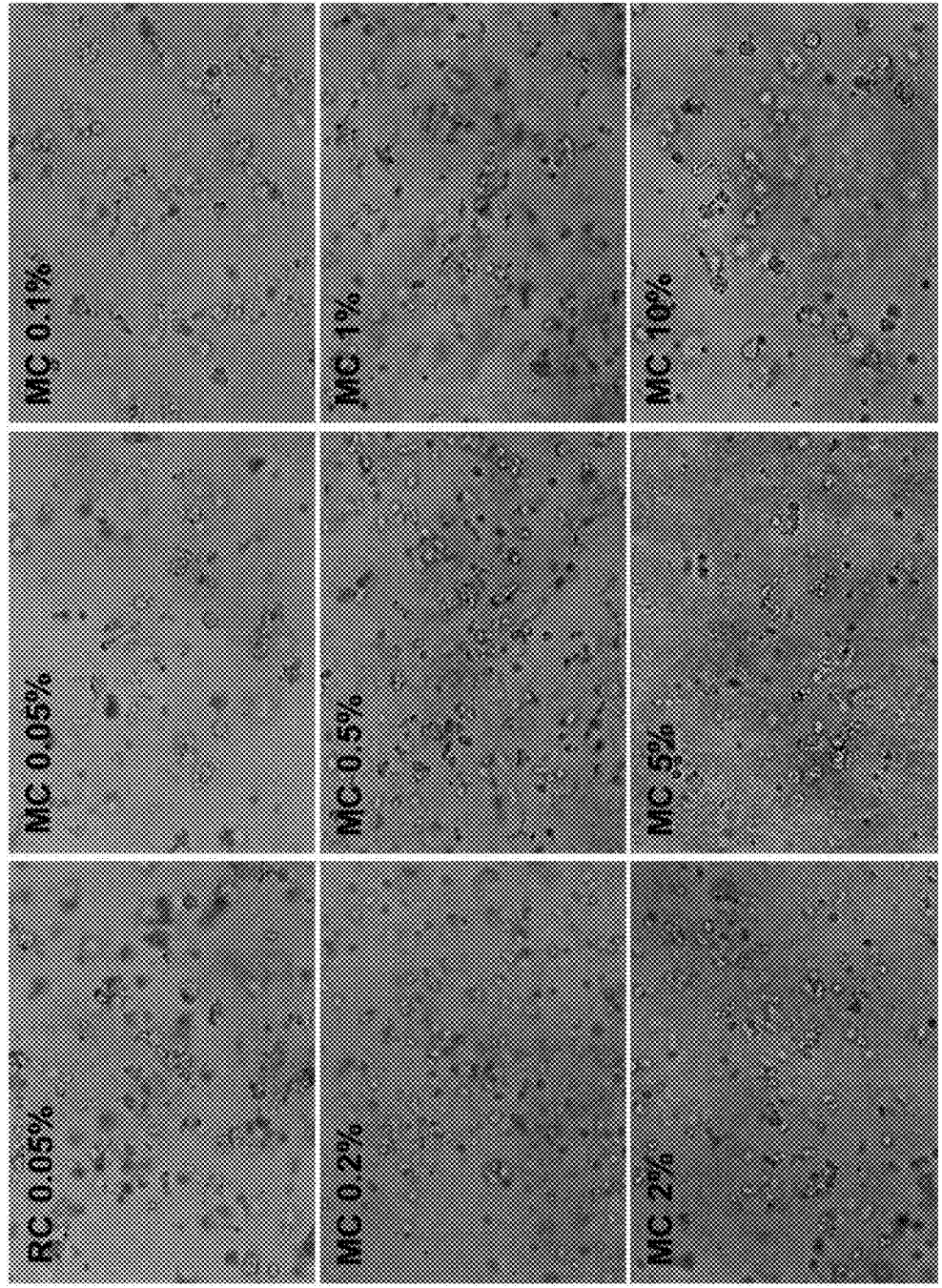
[FIGURE 54]

[FIGURE 55]
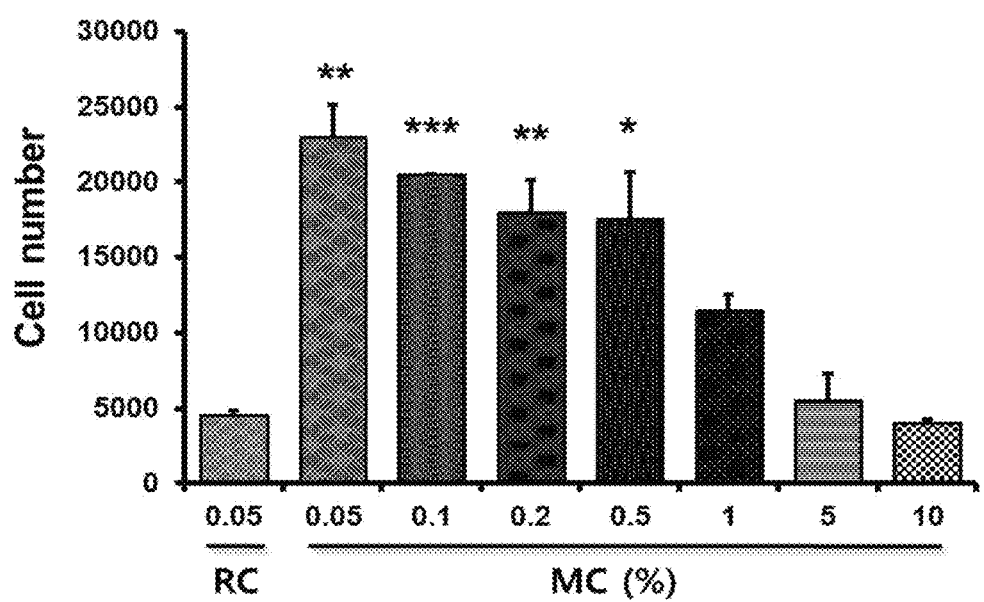

[FIGURE 56]
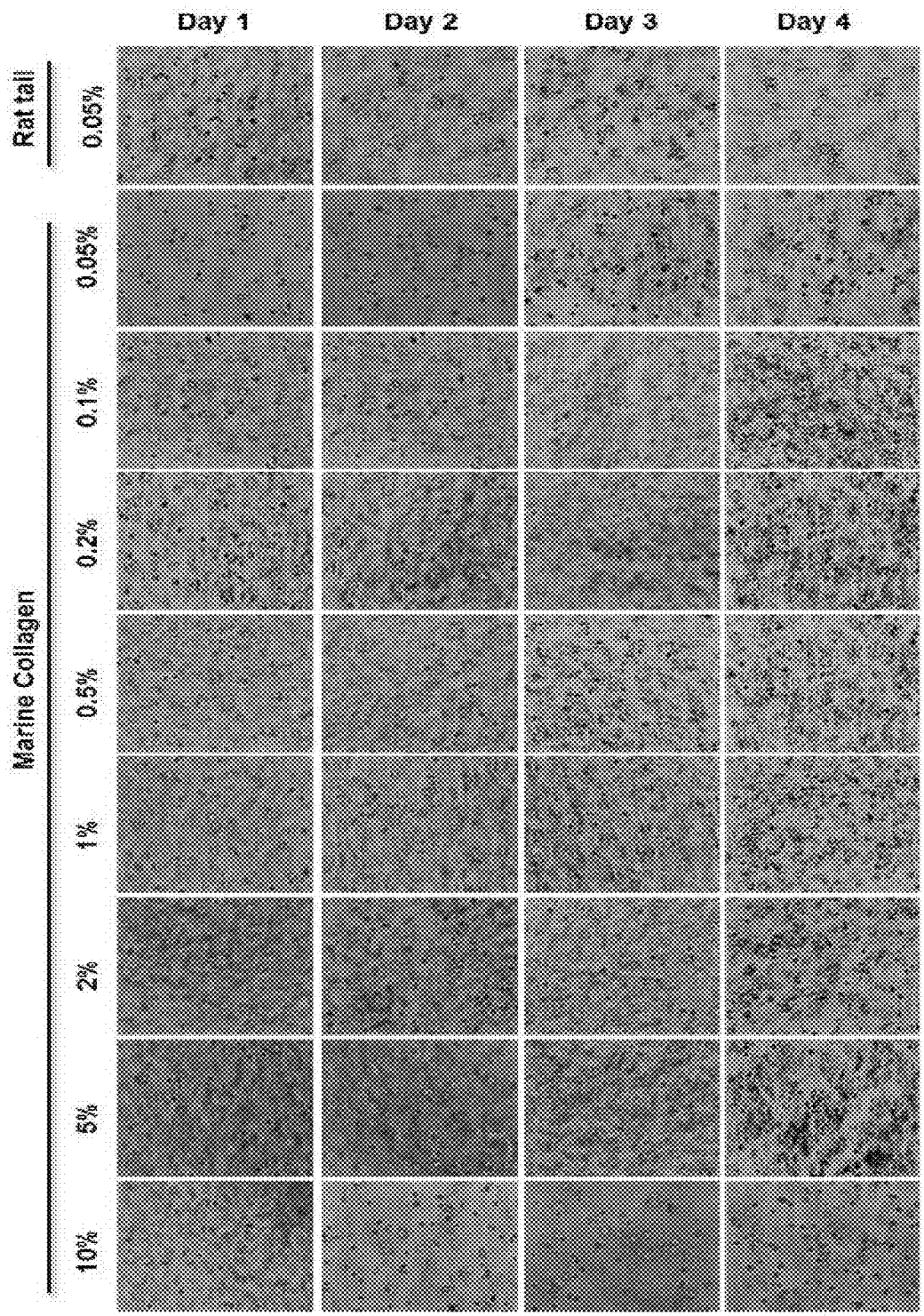

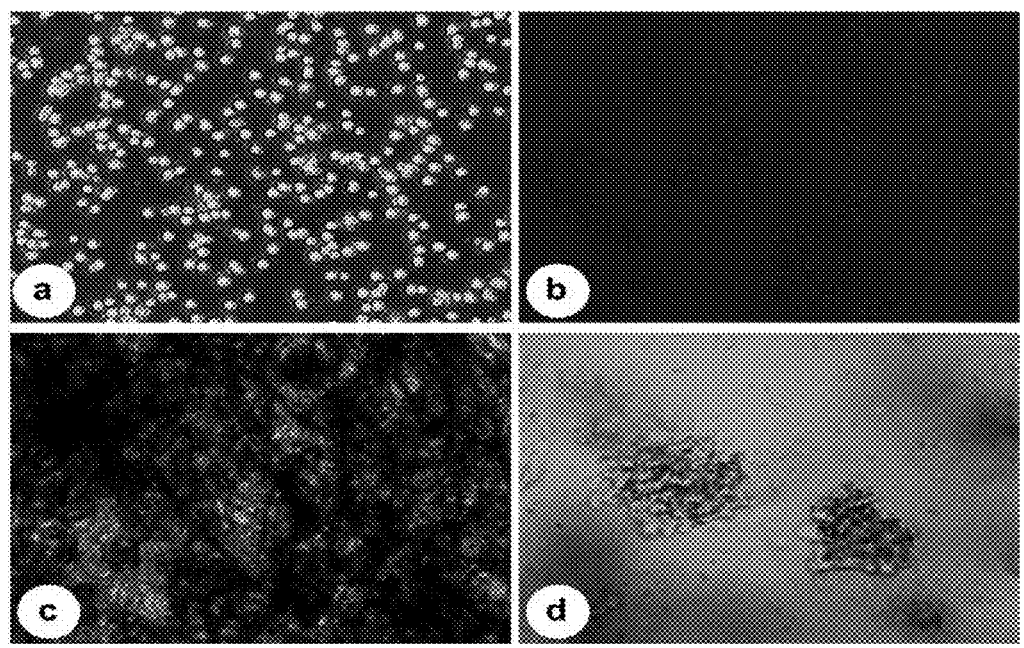
[FIGURE 57]
[FIGURE 58]

[FIGURE 59]
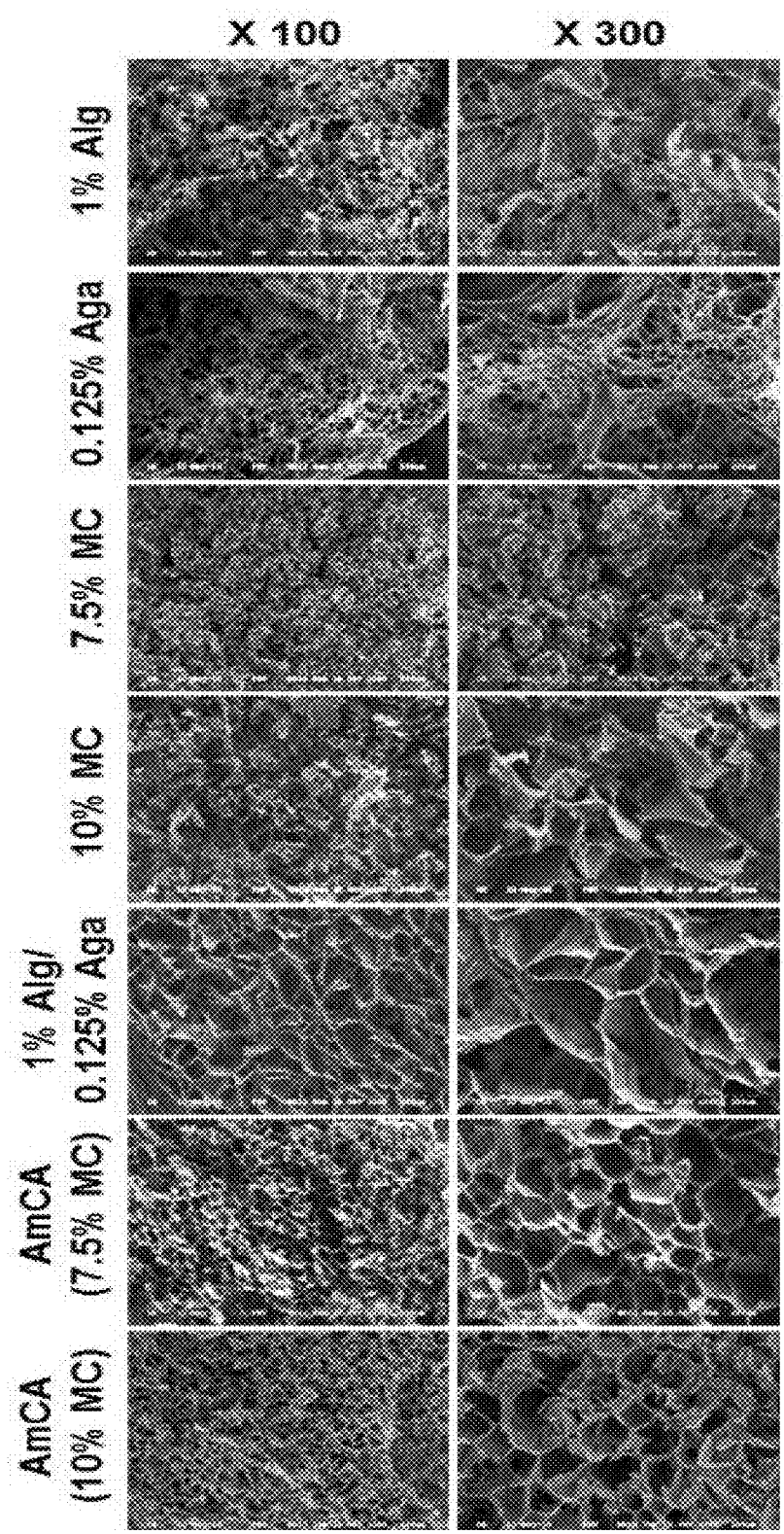

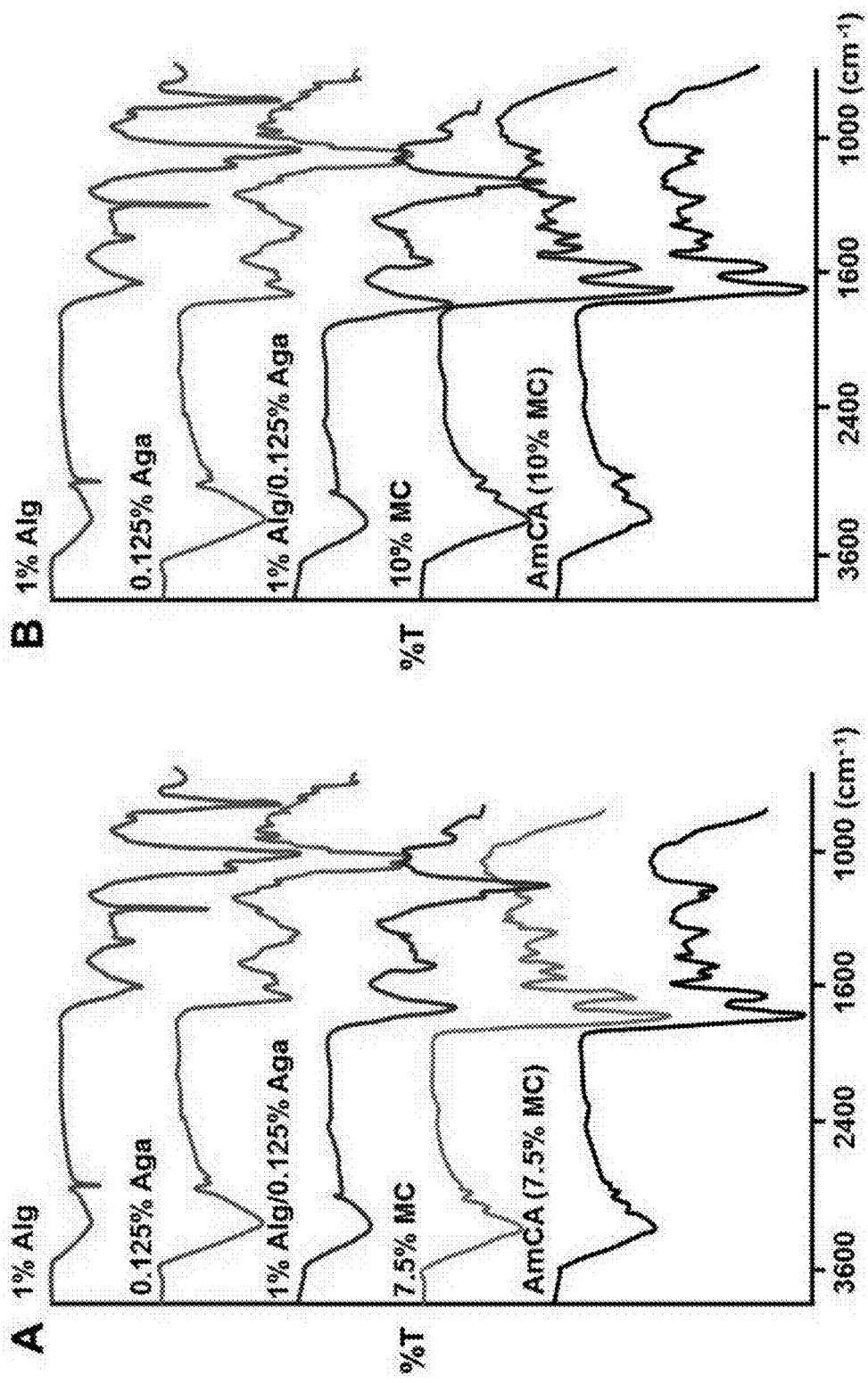
[FIGURE 60]

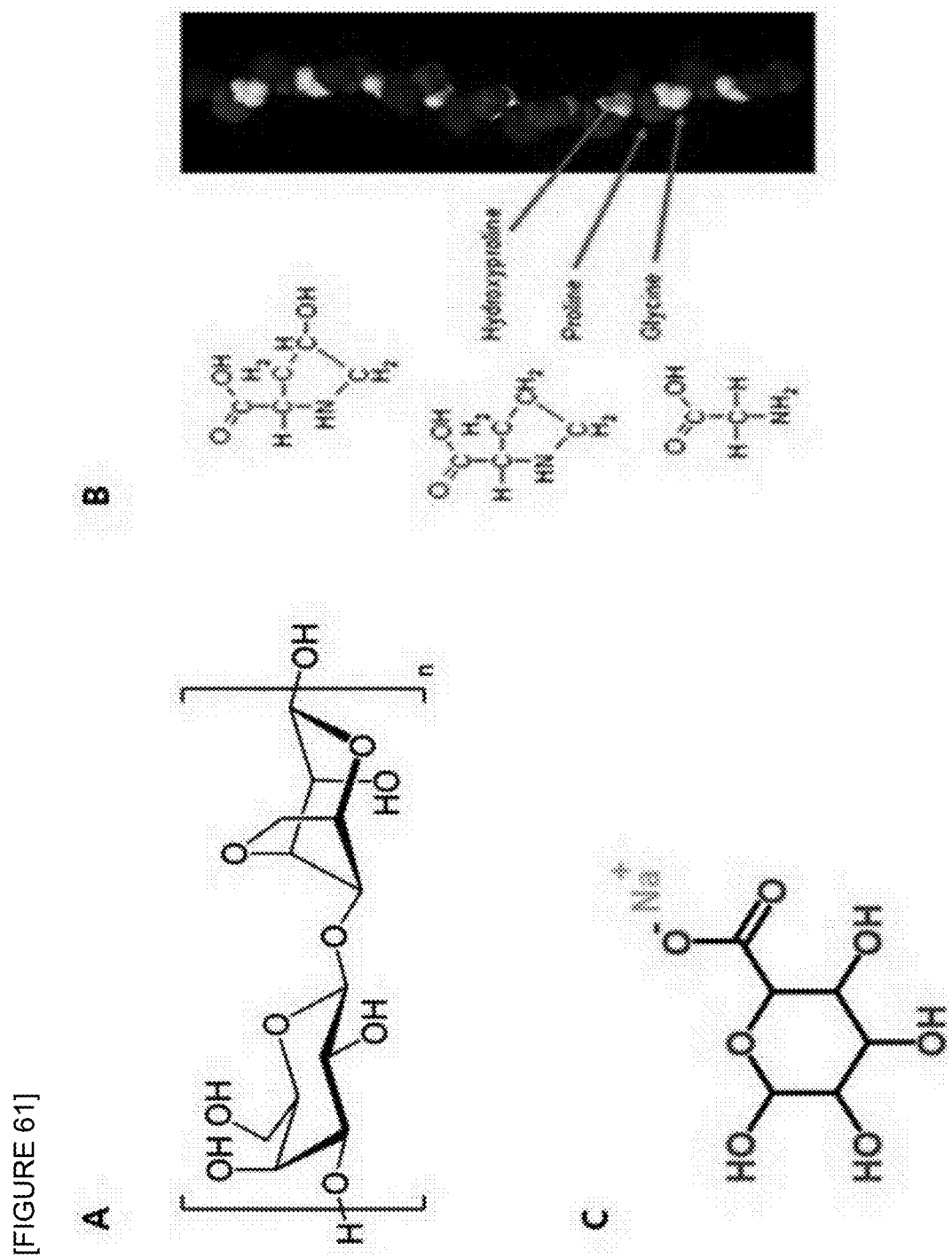
[FIGURE 61]

[FIGURE 62]
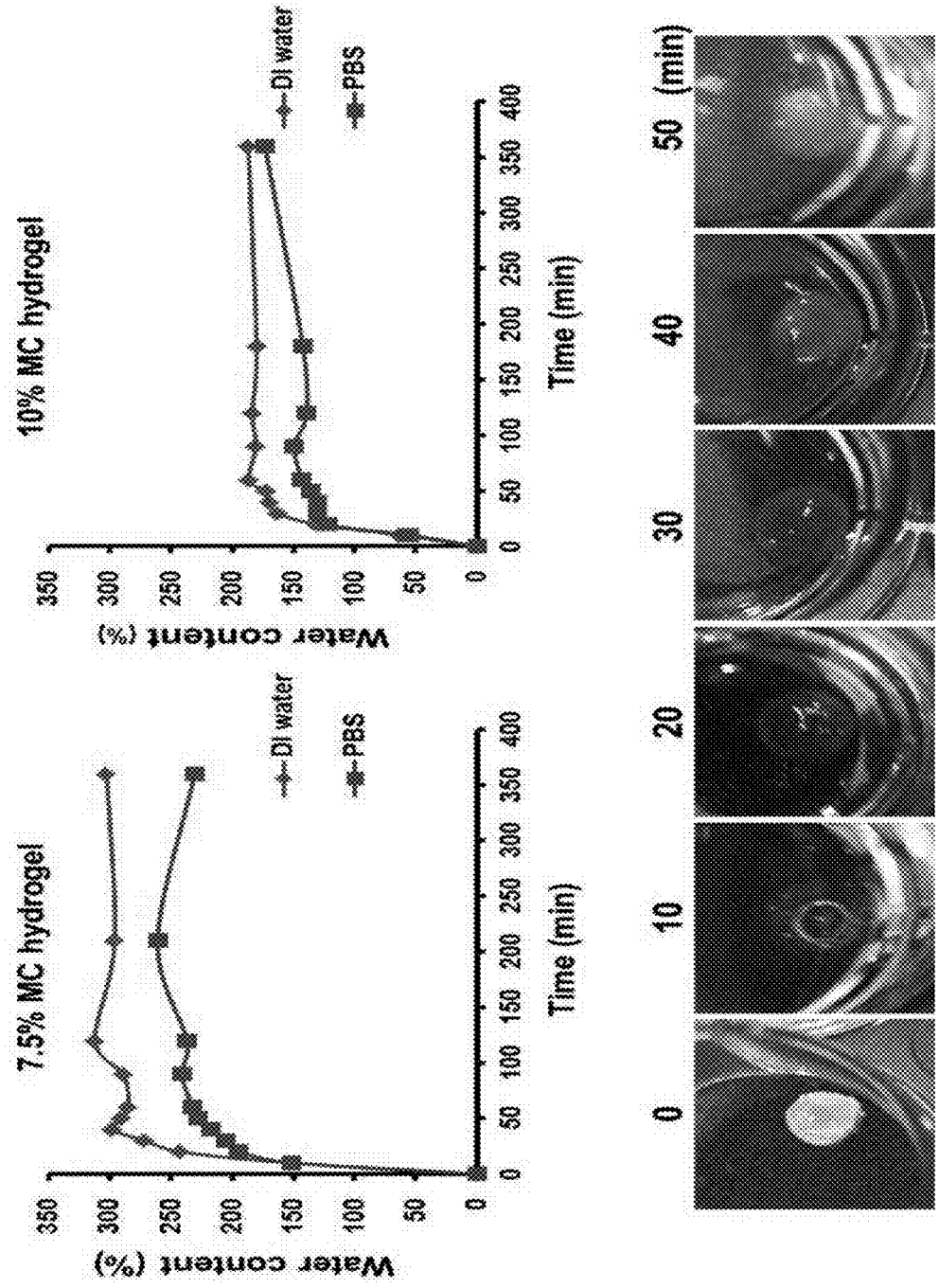

[FIGURE 63]
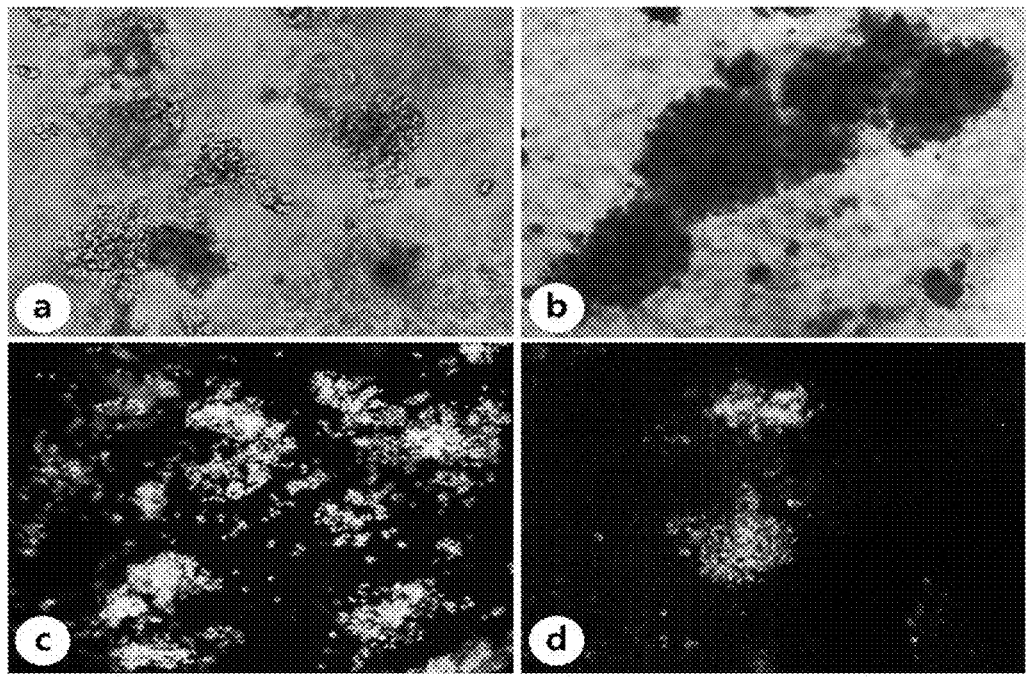
[FIGURE 64]
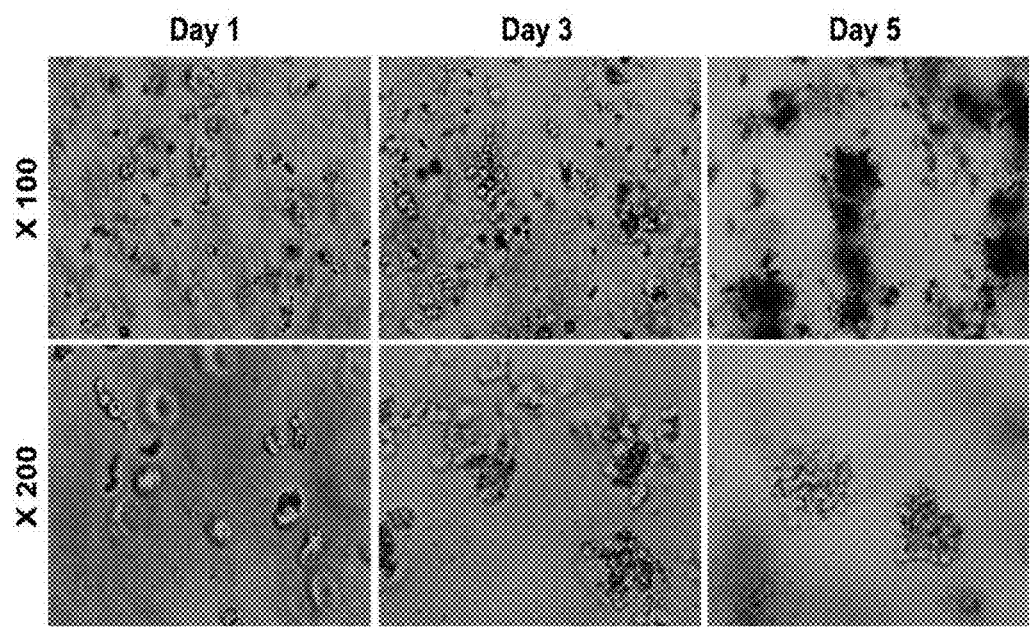

[FIGURE 65]
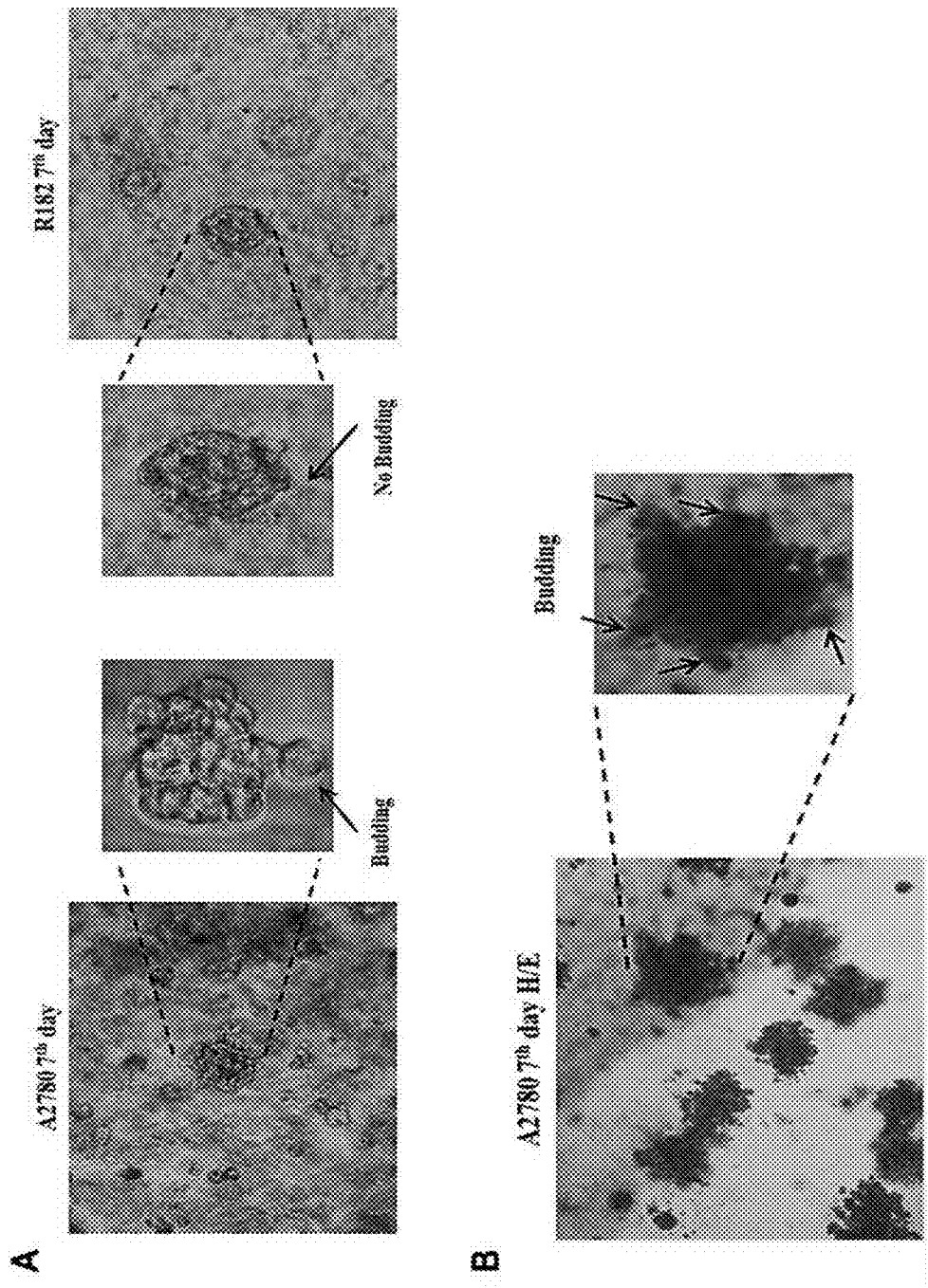

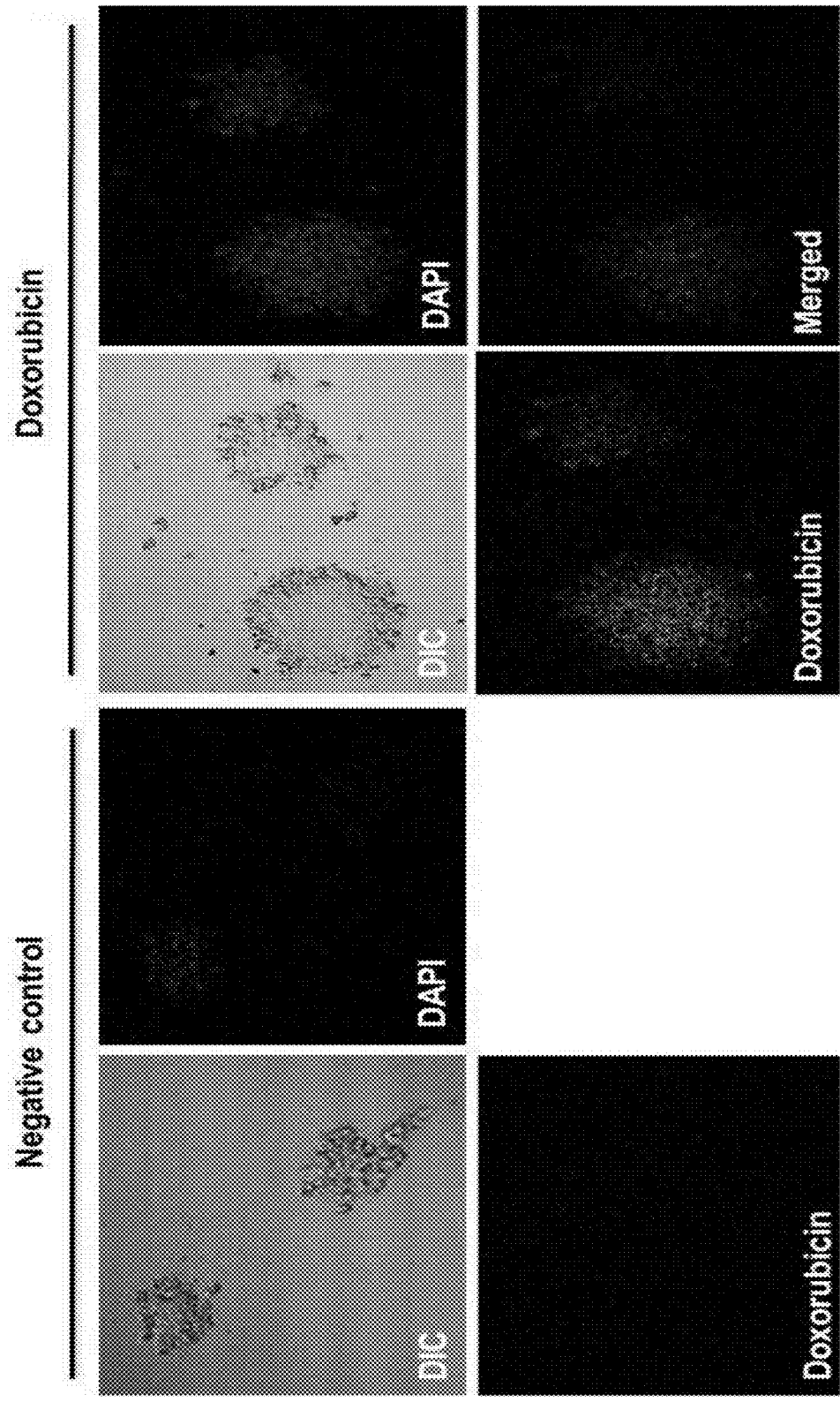
[FIGURE 66]

[FIGURE 67]
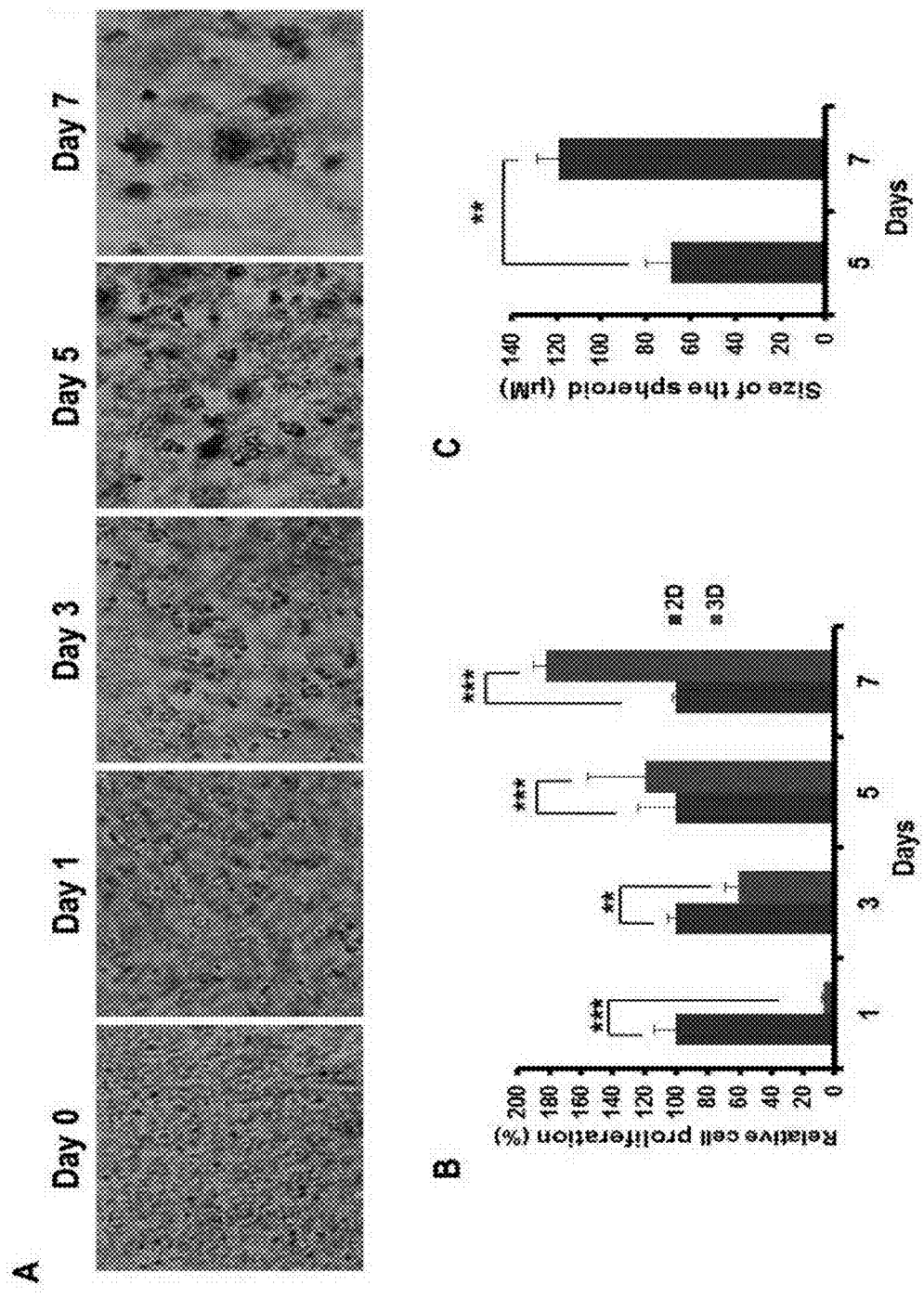

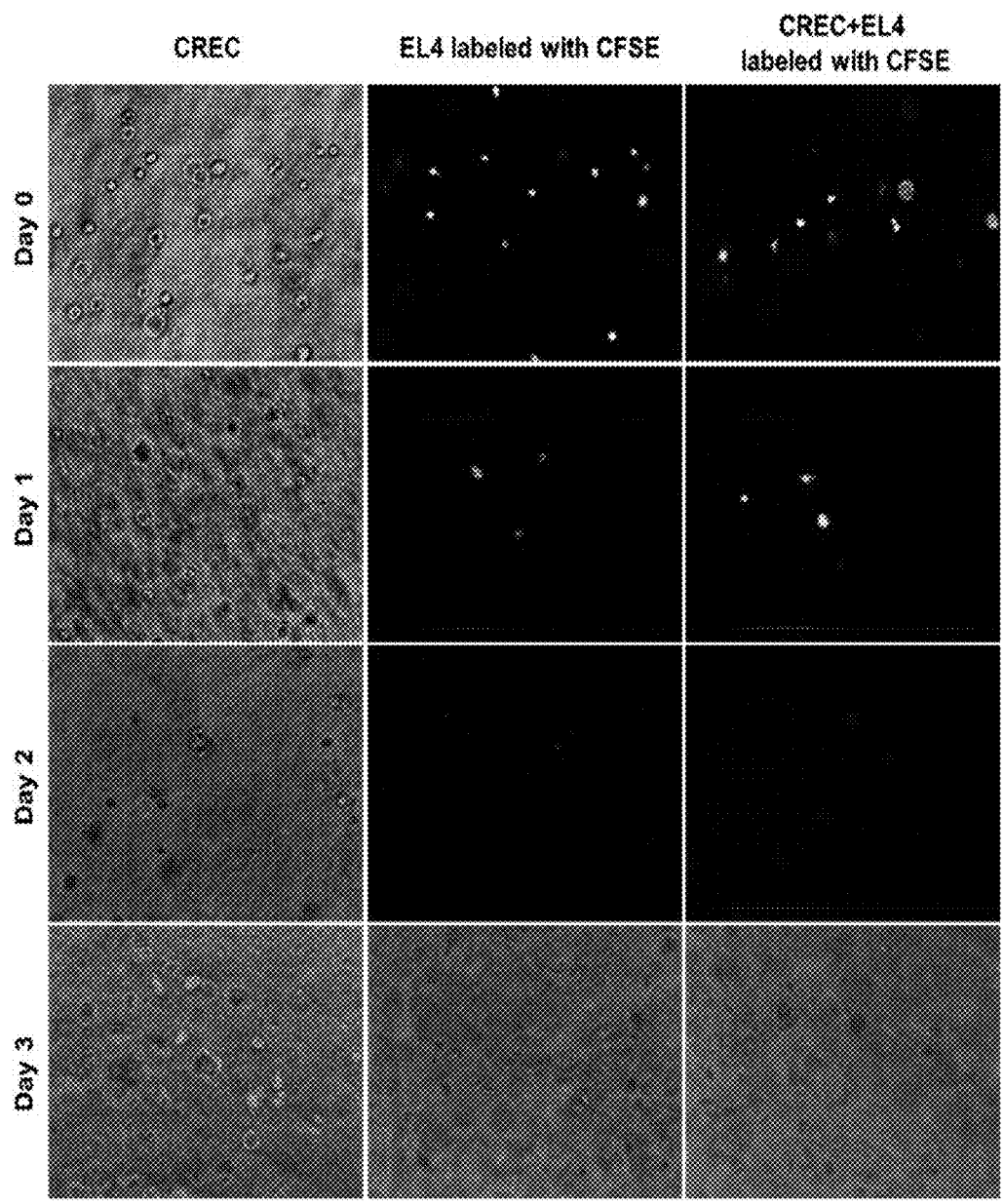
[FIGURE 68]

[FIGURE 69]
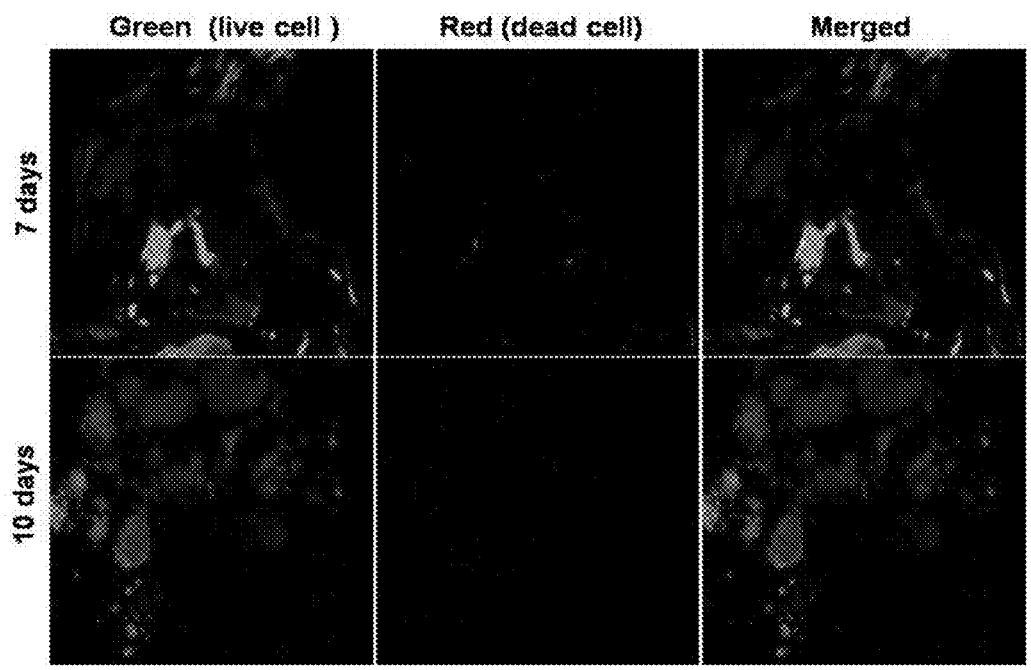
[FIGURE 70]
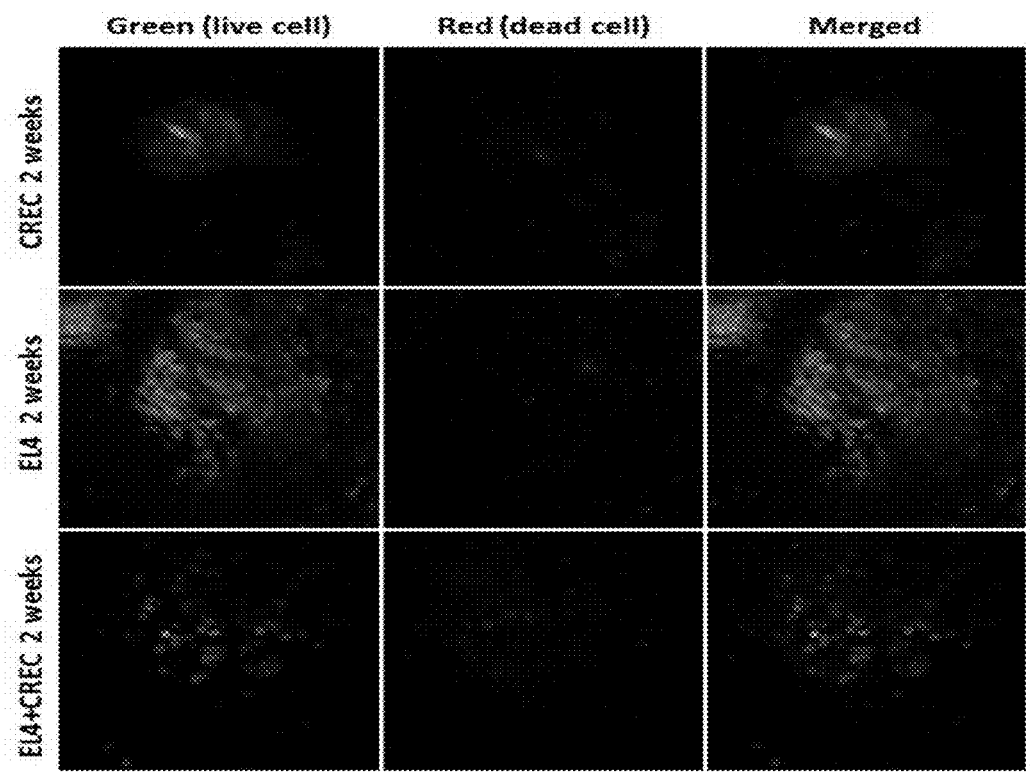

[FIGURE 71]
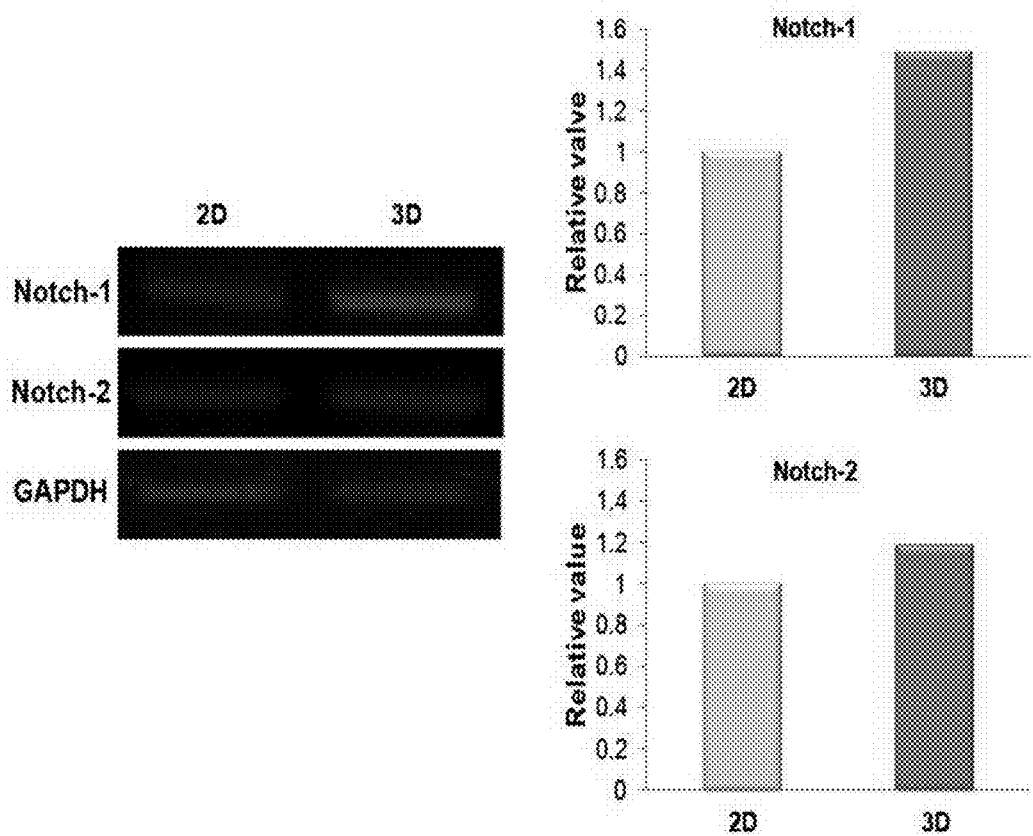
[FIGURE 72]
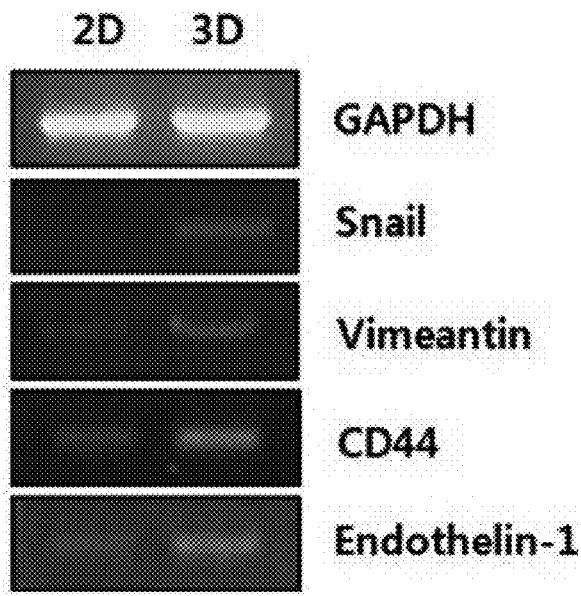

[FIGURE 73]
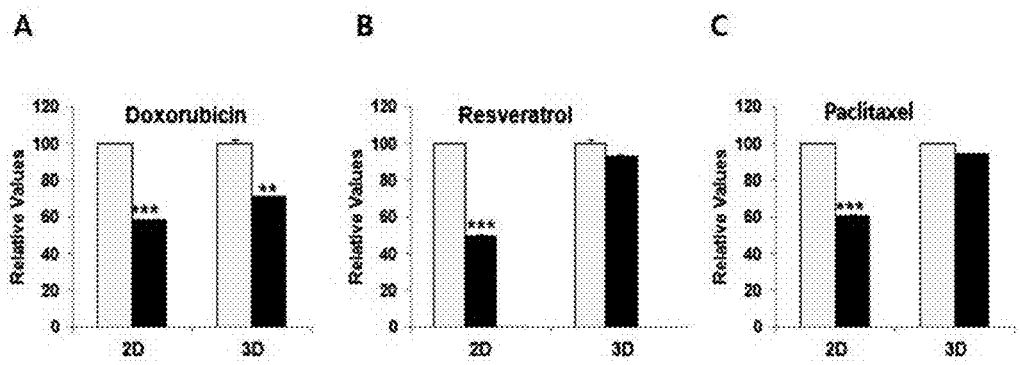
[FIGURE 74]
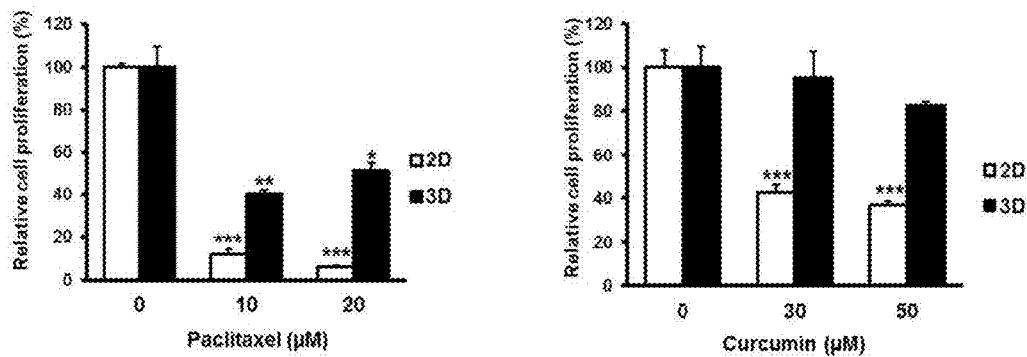
[FIGURE 75]
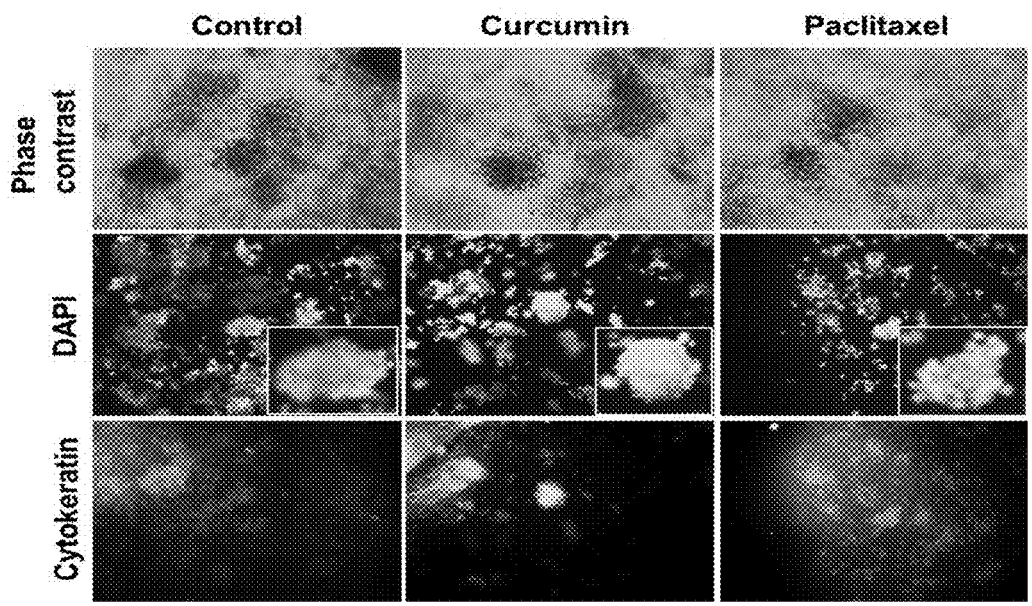

[FIGURE 76]
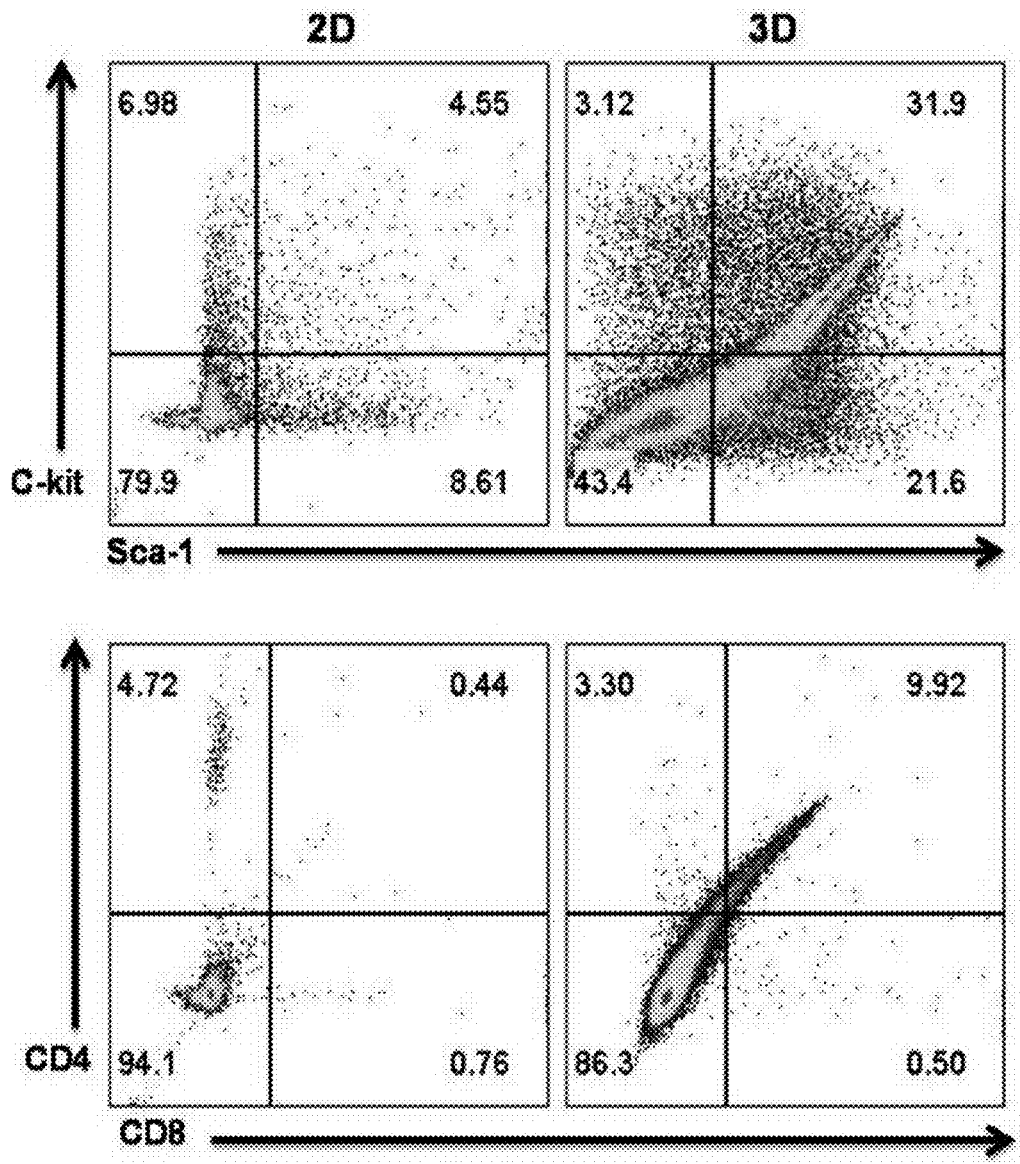

BIOMIMETIC SUPPORT FOR THREE-DIMENSIONAL CELL CULTURING, METHOD FOR MANUFACTURING SAME, AND USE THEREOF

CROSS REFERENCE TO PRIOR APPLICATIONS

This application is a National Stage Application of PCT International Patent Application No. PCT/KR2015/007394 filed on Jul. 16, 2015, under 35 U.S.C. § 371, which claims priority to Korean Patent Application Nos. 10-2014-0089858 filed on Jul. 16, 2014, and 10-2014-0098995 filed on Aug. 1, 2014, which are all hereby incorporated by reference in their entirety.

TECHNICAL FIELD

The present invention relates to a method of preparing nanofiber scaffolds prepared by electrospinning in a mixture solution comprising hydrophilic natural polymers of fish collagen and hydrophobic synthetic polymers, as active ingredients and a use thereof, and a method of biomimetic three-dimensional cell culture using a hydrogel support comprising agarose, collagen and alginate, as active ingredients and a use thereof.

BACKGROUND ART

A tissue engineering has recently attracted an attention as a convergence technology which is intended to be used for clinical treatment by maintaining, enhancing, restoring or replacing vital functions through a combinatory use of cells, engineering materials and appropriate physiological/biochemical factors etc.

The most fundamental technique of this tissue engineering is to attach cells separated from a biological tissue to porous scaffolds made of a biodegradable polymer and to transplant them in vivo or to culture them for a certain period of time in vitro to produce new biological tissues. As it is used in various fields such as restoring or replacing a part or whole of tissues such as bones, cartilage, blood vessels, bladder, skin or muscles, etc., advancement of bio-environmental simulation technology as well as biomaterials, cells, and biologically active factors is essential to develop artificial tissues/organs for the advance of tissue engineering, So far, cell culture methods have been based on culturing cells on a two-dimensional (2D) surface of substrates composed of polystyrene or glass so as to support the growth of adherent cells. However, since a monolayer cell culture method of culturing on the 2D surface cannot accurately reflect the biotissue environment of the three-dimensionally grown cells attached to the extracellular matrix, there are many differences between two-dimensional and the body tissue environment of the cell. As a result, 2D cell culture and three-dimensional (3D) cell culture show overall morphological differences, and phenomena occurring in the actual tissue environment such as expression of receptor, gene transcription regulation, cell migration and apoptosis, are different from those which occur through conventional 2D cell culture.

In addition, because the same cell type is generally cultured in the conventional 2D cell culture, it is difficult to observe interactions between different cell types. Although some attempts have been made to solve these problems partially through 2D co-culture, this 2D co-culture cannot fully mirror the cellular environment in living tissues.

In order to solve the problems of the 2D cell culture, there is a need for research and development of a 3D cell culture method taking account of the spatial organization of the cells. As a method of constructing a simulated cell culture environment for a living cell to solve the problem, research and development have been carried out in order to build a 3D cell culture environment by culturing cells in a porous biocompatible scaffold. As a results, studies on how to manufacture scaffolds using synthetic polymers and natural polymers and on precise cell culture methods specific to the tissues to be studied have been progressed.

However, to date, methods for the production of scaffolds most suitable for regenerating living tissues are not yet known.

DISCLOSURE

Technical Problem

In order to solve the above-mentioned problems, the present invention provides a method of preparing a nanofiber support by electrospinning a mixture solution of fish collagen which is a hydrophilic natural polymer and poly-ε-caprolactone (PCL) which is a hydrophobic polymer, and a biomimetic model for highly functional and highly efficient 3D cell culture by using the same. The present invention also provides a method and a use of 3D cell culturing having extraordinarily high cell culture efficiency using a novel, specially manufactured, agarose-collagen-alginate composite hydrogel support, by which the problems of conventional natural polymer materials can be solved.

Technical Solution

The present invention provides a method of preparing a composite nanofiber support comprising: a first step of dissolving a synthetic polymer in an organic solvent; a second step of dissolving a fish collagen in water to prepare an aqueous fish collagen solution; a third step of adding the aqueous fish collagen solution prepared in the second step to the synthetic polymer solution prepared in the first step, followed by mixing homogeneously; and a fourth step of electrospinning a mixture solution prepared in the third step to prepare a nanofiber support.

The present invention provides a method of culturing three-dimensional cell comprising: a first step of dissolving a synthetic polymer in an organic solvent; a second step of dissolving a fish collagen in water to prepare an aqueous fish collagen solution; a third step of adding the aqueous fish collagen solution prepared in the second step to the synthetic polymer solution prepared in the first step, followed by mixing homogeneously; a fourth step of electrospinning a mixture solution prepared in the third step to prepare a nanofiber support; and a step of culturing cell on the nanofiber support prepared in the fourth step.

The present invention provides a method of culturing three-dimensional cell comprising: a step of mixing and culturing an alginate solution and cells; a step of adding a collagen solution to the alginate-cell mixture to prevent cell detachment; and a step of adding the agarose solution to the alginate-cell-collagen mixture and allowing the mixture to stand, thereby inducing gelation.

The present invention provides a method of measuring cell activity comprising: a step of mixing and culturing an alginate solution and cells; a step of adding a collagen solution to the alginate-cell mixture to prevent cell detachment; a step of adding an agarose solution to the alginatecell-collagen mixture and allowing the mixture to stand and induce gelation, and culturing the cells three-dimensionally; and analyzing growth, proliferation, death, differentiation and migration of cells cultured three-dimensionally.

The present invention provides a method of measuring sensitivity to anticancer drugs comprising: a step of mixing and culturing an alginate solution and cells; a step of adding a collagen solution to the alginate-cell mixture to prevent cell detachment; a step of adding an agarose solution to the alginate-cell-collagen mixture and allowing the mixture to stand and induce gelation, and culturing the cells three-dimensionally; and a step of analyzing cell viability by adding an anticancer drug to cells cultured three-dimensionally.

Advantageous Effects

The fish collagen/synthetic polymer nanofiber support according to the present invention is a composite nanofiber support prepared by electrospinning a solution prepared by adding a natural polymer, fish collagen to a conventional synthetic polymer material and it can exhibit higher mechanical stability than the nanofiber support made of the conventional synthetic polymer materials. In addition, as a result of cell culture using the fish collagen/synthetic polymer nanofiber scaffold of the present invention, it was confirmed that the fish collagen/synthetic polymer nanofiber scaffold of the present invention not only provides a cell culture environment much similar to a living body to remarkably improve 3D cell culture efficiency such as cell adhesion ability, cell viability and cell distribution efficiency and but also shows excellent biomimetic function, indicating its suitability as a 3D cell culture support. Furthermore, since the concentration of the solvent can be easily controlled, a suitable 3D environment can be provided according to the cell to be cultured. Therefore, the 3D cell culture method using the fish collagen/synthetic polymer nanofiber support of the present invention is suitable as a 3D cell culture model which can be used in research for drug sensitivity test, cancer cell formation, growth, metastasis and death, tissue engineering, and regenerative medicine for restoring or replacing a part or whole of tissues such as bones, cartilage, blood vessels, bladder, skin or muscles.

In addition, the agarose-collagen-alginate composite hydrogel support according to the present invention solves the problem of cytotoxicity induced by chemical crosslinking, by inducing gelation by a physical method without chemical crosslinking using ions, and provides high transparency property that allows easy observation of cells by phase-contrast microscope without need of cell staining during culture. In addition, the agarose-collagen-alginate composite hydrogel of the present invention uses marine-derived collagen (hereinafter, referred to as marine collagen), thereby exhibiting the same cell growth effect as a composite hydrogel support using the conventional animal collagen and is economically superior to animal collagen and has high cell affinity, biocompatibility and low cytotoxicity and provides a safe and efficient cell culture method for cells during cell culture.

It is confirmed that the method of 3D cell culture using the agarose-collagen-alginate composite hydrogel support constructs provide a cell culture environment much similar to that of a living body, and has superior spheroid forming ability, drug diffusion ability and cell growth ability. Therefore, the biomimetic 3D cell culture method using the composite hydrogel support according to the present invention can be used for biological activity analysis through observation of cell growth, proliferation, death, differentiation and migration. In addition, it can be used for studies of cancer development, malignant alternation, invasion and metastasis, susceptibility to anticancer drugs and cancer prognosis analysis or evaluation, and can also be effectively used in research for development of therapeutic agents having excellent bioavailability.

DESCRIPTION OF DRAWINGS

FIG. 1 is a photograph (×400) showing the fish collagen/PCL nanofiber and confirming the complete mixing of fish collagen and PCL according to the present invention by a confocal laser scanning microscope after rhodamine staining.

FIG. 2 is a photograph (×400) of a confocal laser scanning microscope showing the cell adhesion by F-actin staining on $F_c$ 0.1 wt %-$S_c$ 20 wt %, $F_c$ 1 wt %-$S_c$ 20 wt % and $F_c$ 2%-$S_c$ 20 wt % fish collagen/PCL nanofiber support, prepared from different concentration of fish collagen (Fc) with the fish collagen stock solution ($S_c$) 20%. The green is F-actin and the blue color is DAPI.

FIG. 3 is a scanning electron microscope image showing the microstructure of fish collagen/PCL nanofiber support prepared from $F_c$ 2 wt %, $F_c$ 3 wt %, $F_c$ 4 wt %, $F_c$ 5 wt % and $F_c$ 10 wt % using fish collagen stock solution of $S_c$ 50 wt %.

FIG. 4 is a scanning electron microscope image showing the microstructure of fish collagen/PCL nanofiber support prepared from $F_c$ 2 wt %, $F_c$ 3 wt %, $F_c$ 4 wt %, $F_c$ 5 wt % and $F_c$ 10 wt % using fish collagen stock solution of $S_c$ 70 wt %.

FIG. 5 is a scanning electron microscope image showing the microstructure of fish collagen/PCL nanofiber support prepared from $F_c$ 2 wt % using fish collagen stock solution ($S_c$) having concentrations of 20 wt %, 30 wt %, 40 wt % and 50 wt %.

FIG. 6 is a scanning electron microscope image showing the microstructure of fish collagen/PCL nanofiber support prepared from $F_c$ 4 wt % using fish collagen stock solution ($S_c$) having concentrations of 40 wt % and 50 wt %.

FIG. 7 is confocal laser scanning micrographs of human lung squamous cell carcinoma cell line (NCI-H1703) seeded onto the electrospun PCL nanofiber support ($F_c$ 0%; PCL 100%) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400). The green is F-actin and the blue color is DAPI (×400).

FIG. 8 is confocal laser scanning micrographs of human lung squamous cell carcinoma cell line (NCI-H1703) seeded onto the electrospun fish collagen/PCL nanofiber support ($F_c$ 2 wt %-$S_c$ 30 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 9 is confocal laser scanning micrographs of human lung squamous cell carcinoma cell line (NCI-H1703) seeded onto the electrospun fish collagen/PCL nanofiber support ($F_c$ 2 wt %-$S_c$ 50 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 10 is confocal laser scanning micrographs of human lung squamous cell carcinoma cell line (NCI-H1703) seeded onto the electrospun fish collagen/PCL nanofiber support ($F_c$ 2 wt %-$S_c$ 70 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 11 is confocal laser scanning micrographs of human lung squamous cell carcinoma cell line (NCI-H1703) seeded onto the electrospun fish collagen/PCL nanofiber support ($F_c$ 5 wt %-$S_c$ 50 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 12 is confocal laser scanning micrographs of human lung squamous cell carcinoma cell line (NCI-H1703) seeded onto the electrospun fish collagen/PCL nanofiber support ($F_c$ 5 wt %-$S_c$ 70 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 13 is confocal laser scanning micrographs of human lung squamous cell carcinoma cell line (NCI-H1703) seeded onto the electrospun fish collagen/PCL nanofiber support ($F_c$ 10 wt %-$S_c$ 50 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 14 is confocal laser scanning micrographs of human lung squamous cell carcinoma cell line (NCI-H1703) seeded onto the electrospun fish collagen/PCL nanofiber support ($F_c$ 10 wt %-$S_c$ 70 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 15 is confocal laser scanning micrographs of human lung squamous cell carcinoma cell line (NCI-H1703) seeded onto the electrospun fish collagen/PCL nanofiber support ($F_c$ 15 wt %-$S_c$ 70 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 16 is confocal laser scanning micrographs of human lung squamous cell carcinoma cell line (NCI-H1703) seeded onto the electrospun fish collagen/PCL nanofiber support ($F_c$ 20 wt %-$S_c$ 70 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 17 is confocal laser scanning micrographs of human prostate cancer cell line (DU-145) seeded onto the electrospun PCL nanofiber support ($F_c$ 0%; PCL 100%) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 18 is confocal laser scanning micrographs of human prostate cancer cell line (DU-145) seeded onto the electrospun fish collagen/PCL nanofiber support ($F_c$ 2 wt %-$S_c$ 30 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 19 is confocal laser scanning micrographs of human prostate cancer cell line (DU-145) seeded onto the electrospun fish collagen/PCL nanofiber support ($F_c$ 2 wt %-$S_c$ 50 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 20 is confocal laser scanning micrographs of human prostate cancer cell line (DU-145) seeded onto the electrospun fish collagen/PCL nanofiber support ($F_c$ 2 wt %-$S_c$ 70 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 21 is confocal laser scanning micrographs of human prostate cancer cell line (DU-145) seeded onto the electrospun fish collagen/PCL nanofiber support ($F_c$ 5 wt %-$S_c$ 50 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 22 is confocal laser scanning micrographs of human prostate cancer cell line (DU-145) seeded onto the electrospun fish collagen/PCL nanofiber support ($F_c$ 5 wt %-$S_c$ 70 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 23 is confocal laser scanning micrographs of human prostate cancer cell line (DU-145) seeded onto the electrospun fish collagen/PCL nanofiber support ($F_c$ 10 wt %-$S_c$ 50 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 24 is confocal laser scanning micrographs of human prostate cancer cell line (DU-145) seeded onto the electrospun fish collagen/PCL nanofiber support ($F_c$ 10 wt %-$S_c$ 70 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 25 is confocal laser scanning micrographs of human prostate cancer cell line (DU-145) seeded onto the electrospun fish collagen/PCL nanofiber support ($F_c$ 15 wt %-$S_c$ 70 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 26 is confocal laser scanning micrographs of human prostate cancer cell line (DU-145) seeded onto the electrospun fish collagen/PCL nanofiber support ($F_c$ 20 wt %-$S_c$ 70 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 27 is confocal laser scanning micrographs of mouse B cell lymphoma cell line (A20) seeded onto the electrospun PCL nanofiber support ($F_c$ 0%; PCL 100%) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 28 is confocal laser scanning micrographs of mouse B cell lymphoma cell line (A20) seeded onto the electrospun fish collagen/PCL nanofiber support ($F_c$ 2 wt %-$S_c$ 30 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 29 is confocal laser scanning micrographs of mouse B cell lymphoma cell line (A20) seeded onto the electrospun fish collagen/PCL nanofiber support ($F_c$ 2 wt %-$S_c$ 50 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 30 is confocal laser scanning micrographs of mouse B cell lymphoma cell line (A20) seeded onto the electrospun fish collagen/PCL nanofiber support ($F_c$ 2 wt %-$S_c$ 70 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 31 is confocal laser scanning micrographs of mouse B cell lymphoma cell line (A20) seeded onto the electrospun fish collagen/PCL nanofiber support ($F_c$ 5 wt %-$S_c$ 50 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 32 is confocal laser scanning micrographs of mouse B cell lymphoma cell line (A20) seeded onto the electrospun fish collagen/PCL nanofiber support ($F_c$ 5 wt %-$S_c$ 70 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 33 is confocal laser scanning micrographs of mouse B cell lymphoma cell line (A20) seeded onto the electrospun fish collagen/PCL nanofiber support ($F_c$ 10 wt %-$S_c$ 70 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 34 is confocal laser scanning micrographs of mouse B cell lymphoma cell line (A20) seeded onto the electrospun fish collagen/PCL nanofiber support ($F_b$ 15 wt %-$S_c$ 70 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 35 is confocal laser scanning micrographs of mouse B cell lymphoma cell line (A20) seeded onto the electrospun fish collagen/PCL nanofiber support ($F_c$ 20 wt %-$S_c$ 70 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 36 is confocal laser scanning micrographs of mouse T cell lymphoma cell line (EL4) seeded onto the electrospun PCL nanofiber support ($F_c$ 0%; PCL 100%) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 37 is confocal laser scanning micrographs of mouse T cell lymphoma cell line (EL4) seeded onto the electrospun fish collagen/PCL nanofiber support ($F_c$ 2 wt %-$S_c$ 30 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 38 is confocal laser scanning micrographs of mouse T cell lymphoma cell line (EL4) seeded onto the electrospun fish collagen/PCL nanofiber support ($F_c$ 2 wt %-$S_c$ 50 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 39 is confocal laser scanning micrographs of mouse T cell lymphoma cell line (EL4) seeded onto the electrospun fish collagen/PCL nanofiber support ($F_c$ 2 wt %-$S_c$ 70 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 40 is confocal laser scanning micrographs of mouse T cell lymphoma cell line (EL4) seeded onto the electrospun fish collagen/PCL nanofiber support ($F_c$ 5 wt %-$S_c$ 50 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 41 is confocal laser scanning micrographs of mouse T cell lymphoma cell line (EL4) seeded onto the electrospun fish collagen/PCL nanofiber support ($F_c$ 5 wt %-$S_c$ 70 wt %) after 1 day of 3D cell culture. Z-stack images of different planes showing from surface to bottom with 1 μm plane thickness (A), a reconstructed 3D projection image (B), and an enlarged image (C) are shown. Cells were stained with FITC-phalloidin (green) for F-actin cytoskeleton and DAPI (blue) for nucleus (×400).

FIG. 42 illustrates an analysis result of an effect of the PCL nanofiber support and the $F_c$ 2 wt %-$S_c$ 50 wt % fish collagen/PCL nanofiber support on survival of mouse B-cell lymphoma cells during cell culture thereof by a confocal laser scanning microscopic observation (×400) of the Live/Dead cells after seeding the mouse B cell lymphoma cell and culturing for 2 days.

FIG. 43 illustrates an analysis result of an effect of the PCL nanofiber support and the $F_c$ 2 wt %-$S_c$ 50 wt % fish collagen/PCL nanofiber support on survival of mouse B-cell lymphoma cells during cell culture thereof by a confocal laser scanning microscopic observation (×400) of the Live/Dead cells after seeding the mouse B cell lymphoma cell and culturing for 6 days.

FIG. 44 shows a result of diffusion degree of anti-cancer agents after treating 1 μM doxorubicin, a standard anti-cancer drug against lymphoma, to 3D culture model of mouse T lymphoma cells using $F_c$ 2 wt %-Sc 50 wt % fish collagen/PCL nanofiber support according to the present invention, for evaluating the diffusion ability of the drug to reach cancer cells in a 3D environment.

FIG. 45 shows the sensitivity of anticancer drugs by measuring the cell viability of human lung cancer cells (NCI-H1703, A) and prostate cancer cells (DU-145, B) cultured in a conventional two-dimensional environment and three-dimensional environment using $F_c$ 4 wt %-$S_c$ 50 wt % fish collagen/PCL nanofiber support according to the present invention.

FIG. 46 shows expression levels of Hes 1 and Notch genes related to malignancy by RT-PCR of human prostate cancer cells (DU-145, B) cultured in a conventional two-dimensional environment and three-dimensional environment using $F_c$ 4 wt %-$S_c$ 50 wt % fish collagen/PCL nanofiber support according to the present invention.

FIG. 47 shows expression levels of snail, slug, endothelin-1, CD44, VEGF, and HIF-1α genes related to malignancy by RT-PCR of human prostate cancer cells (DU-145, B) cultured in a conventional two-dimensional environment and three-dimensional environment using $F_c$ 4 wt %-$S_c$ 50 wt % fish collagen/PCL nanofiber support according to the present invention.

FIG. 48 shows flow cytometric analysis of measuring the cancer stem cell-forming ability and the differentiation ability of mouse T cell lymphoma cell line cultured three-dimensionally in $F_c$ 2 wt %-$S_c$ 50 wt % fish collagen/PCL nanofiber support according to the present invention.

FIG. 49 is a schematic diagram showing a composition of agarose-collagen-alginate composite hydrogel according to the present invention.

FIG. 50 is a schematic diagram showing a production process of agarose-collagen-alginate composite hydrogel according to the present invention.

FIG. 51 is a WST-1 analysis result of cytotoxic effect of $CaCl_2$ after treating a mouse normal cell, CREC and cancer cell lines, EL4, R182 and A2780 cells with $CaCl_2$ having various concentrations (10, 50, 100, 200 and 300 mM) for 18 to 24 hours.

FIG. 52 is photographs by a phase-contrast microscope to investigate three-dimensional cell growth environment after culturing the A2780 cells in agarose-alginate composite hydrogel in which the final concentration of the agarose is 0.125 wt % and the final concentration of the alginate is 1 wt % in mixed solution prepared from 0.5, 1 and 1.5 wt % agarose solution (referred to as hereinafter "0.125 wt % agarose-1 wt % alginate composite hydrogel").

FIG. 53 is photographs by a phase-contrast microscope to investigate EL4 cell growth after culturing EL4 cells three-dimensionally in pure agarose gels having concentrations of 0.5, 1, 1.5 and 2 wt % for 2, 5 and 10 days.

FIGS. 54 and 55 are photographs by a phase-contrast microscope to investigate the detached cells from the hydrogels. EL4 cells were seeded in the 0.125% agarose-1% alginate composite hydrogel containing 0.05% rat tail collagen (RC) and in 0.125% agarose-1% alginate composite hydrogels containing different concentrations of marine collagen at 0.05, 0.1, 0.2, 0.5, 1, 2, 5 and 10%. The encapsulation efficiency of EL4 cells among these hydrogels was observed. FIG. 54 is a phase contrast microscopic image of non-encapsulated cells, and FIG. 55 is a bar graph showing the numbers of non-encapsulated EL4 cells.

FIG. 56 is photographs by a phase-contrast microscope to investigate cell growth after culturing EL4 cells for 18 to 24 hours in supports containing 0.125 wt % agarose-collagen-1 wt % alginate composite hydrogel, in which both conventional animal collagen and marine collagen were used. A marine collagen was attempted firstly according to the present invention, as a source of collagen.

FIG. 57 is photographs by a phase-contrast microscope to investigate cell growth after culturing A2780 cells three-dimensionally in supports containing 0.125 wt % agarose-collagen-1 wt % alginate composite hydrogel, in which the conventional animal collagen and marine collagen were used. A marine collagen was attempted firstly according to the present invention, as a source of collagen.

FIG. 58 is photographs by a phase-contrast microscope to confirm the transparency of agarose-collagen-alginate composite hydrogel support according to the present invention.

FIG. 59 is photographs by a scanning electron microscope to observe the cross section of hydrogel supports composed with 1 wt % of pure alginate, 0.125 wt % of pure agarose, 7.5 or 10 wt % of pure marine collagen, 0.125 wt % agarose-1 wt % alginate composite hydrogel support and 0.125 wt % agarose-7.5 wt % marine collagen-1 wt % alginate and 0.125 wt % agarose-10 wt % marine collagen-1 wt % alginate composite hydrogel support.

FIG. 60 is FT-IR analysis result of hydrogel supports composed with 1 wt % of pure alginate, 0.125 wt % of pure agarose, 7.5 or 10 wt % of pure marine collagen, 0.125 wt % agarose-1 wt % alginate composite hydrogel support and 0.125 wt % agarose-7.5 wt % marine collagen-1 wt % alginate and 0.125 wt % agarose-10 wt % marine collagen-1 wt % alginate composite hydrogel support.

FIG. 61 is a schematic diagram of the molecular structure of each component of the hydrogel material. FIGS. 61A, 61B and 61C are schematic diagrams of the molecular structure of agarose, marine collagen and alginate, respectively.

FIG. 62 is a graph showing the swelling behavior of 0.125 wt % agarose-7.5 wt % marine collagen-1 wt % alginate and 0.125 wt % agarose-10 wt % marine collagen-1 wt % alginate composite hydrogel supports in distilled water and phosphate buffered saline (PBS) according to the invention.

FIG. 63 is results by a light microscope (a), H&E staining (b), DAPI staining (c) and F-actin staining (d) after culturing human ovarian cancer cells for 7 days in 0.125 wt % agarose-7.5 wt % marine collagen-1 wt % alginate composite hydrogel support according to the present invention.

FIG. 64 is results by a phase contrast microscope to observe cell spheroids formed after culturing EL4 cells for 1, 3 and 5 days in 0.125 wt % agarose-10 wt % marine collagen-1 wt % alginate composite hydrogel support according to the present invention.

FIG. 65 is results observing spheroid budding phenomena that play an important role in cell spheroid formation, after culturing A2780 cells in 0.125 wt % agarose-7.5 wt % marine collagen-1 wt % alginate composite hydrogel support according to the present invention. FIGS. 65A and 65B are results by a phase difference microscope and H&E staining, respectively.

FIG. 66 is a result confirming the diffusion ability of the drug to reach the tumor in the three-dimensional environment by using three-dimensional culture model of human ovarian cancer cells A2780 in 0.125 wt % agarose-7.5 wt % marine collagen-1 wt % alginate composite hydrogel support according to the present invention.

FIG. 67 is a result of the cell proliferation ability after culturing human ovarian cancer A2780 for 1, 3, 5 and 7 days in the two-dimensional culture environment and the three-dimensional environment using 0.125 wt % agarose-7.5 wt % marine collagen-1 wt % alginate composite hydrogel support according to the present invention, respectively.

FIG. 68 is a result by a CFSE staining to confirm the cell proliferation after three-dimensionally culturing CREC and EL4 cells in 0.125 wt % agarose-10 wt % marine collagen-1 wt % alginate composite hydrogel support according to the invention.

FIGS. 69 and 70 are results showing the cytotoxicity of the agarose-marine collagen-alginate composite hydrogel support according to the present invention. FIG. 69 is a result by a confocal laser microscopic observation of Live/Dead cells after seeding human ovarian cancer cells A2780 in 0.125 wt % agarose-7.5 wt % marine collagen-1 wt % alginate composite hydrogel support according to the present invention and culturing them for 7 and 10 days. FIG. 70 is a result by a confocal laser microscopic observation of Live/Dead cells after seeding CREC and CL4 cells in 0.125 wt % agarose-10 wt % marine collagen-1 wt % alginate composite hydrogel support according to the present invention and culturing them for 14 days, for confirming the cytotoxicity.

FIG. 71 shows expression levels of Notch genes related to malignancy of the cancer cell by RT-PCR after culturing EL4 cells two dimensionally and three-dimensionally in 0.125 wt % agarose-10 wt % marine collagen-1 wt % alginate composite hydrogel support according to the present invention, respectively.

FIG. 72 shows expression levels of snail and vimentin which are malignancy markers of the cancer cells, CD44 which is an important marker of cancer stem cells, and endothelin-1 which plays a key role in growth and metastasis of tumors after culturing human ovarian cancer cells two dimensionally and three-dimensionally in 0.125 wt % agarose-7.5 wt % marine collagen-1 wt % alginate composite hydrogel support according to the present invention, respectively.

FIG. 73 is a result identifying the cell viability of anticancer drugs after culturing lymphoma cells (EL4) and human ovarian cancer cells (A2780) two dimensionally and three-dimensionally in 0.125 wt % agarose-10 wt % marine collagen-1 wt % alginate composite hydrogel support according to the present invention, respectively.

FIG. 73 is a result identifying the cell viability against anticancer drugs after culturing lymphoma cells (EL4) and human ovarian cancer cells (A2780) two dimensionally and three-dimensionally in 0.125 wt % agarose-10 wt % marine collagen-1 wt % alginate composite hydrogel support according to the present invention, respectively.

FIG. 74 is a result identifying the cell viability of ovarian cancer cells against a standard anticancer agent, paclitaxel and curcumin, which have anticancer effect against various cancer cells, after culturing human ovarian cancer cells (A2780) two dimensionally and three-dimensionally in 0.125 wt % agarose-7.5 wt % marine collagen-1 wt % alginate composite hydrogel support according to the present invention, respectively.

FIG. 75 is results observing the cells by phase contrast microscopy and fluorescence microscopy in human ovarian cancer cells (A2780) cultured three-dimensionally in 0.125 wt % agarose-7.5 wt % marine collagen-1 wt % alginate composite hydrogel support according to the present invention after immunostaining with antibodies against cytokeratin which is a marker specifically expressed in the epithelial cells.

FIG. 76 shows flow cytometric analysis of measuring the cancer stem cell-forming ability and the differentiation ability of EL4 cells cultured three-dimensionally in 0.125 wt % agarose-10 wt % marine collagen-1 wt % alginate composite hydrogel support according to the present invention.

BEST MODE

The present invention provides a method of preparing a composite nanofiber support comprising: a first step of dissolving a synthetic polymer in an organic solvent; a second step of dissolving a fish collagen in water to prepare an aqueous fish collagen solution; a third step of adding the aqueous fish collagen solution prepared in the second step to the synthetic polymer solution prepared in the first step, followed by mixing homogeneously; and a fourth step of electrospinning a mixture solution prepared in the third step to prepare a nanofiber support.

The synthetic polymer solution in the first step may be prepared by dissolving 8 to 10 parts by weight of a synthetic polymer, based on 100 parts by weight of the organic solvent. More preferably, the synthetic polymer solution of 8.8 wt % may be prepared, but is not limited thereto.

If the addition range of the synthetic polymer is out of the range, electrospinning may not be performed, or it may be difficult to produce homogeneous nanofibers during electrospinning.

The synthetic polymer may be one or more selected from the group consisting of poly($\varepsilon$-caprolactone) (PCL), poly (lactic acid) (PLA), poly(glycolic acid) (PGA), poly(hydroxy valerate) (PHV), poly (lactic-co-glycolic acid) (PLGA), poly-hydroxy butyrate (PHB), poly (hydroxy butyrate-co-valerate (PHBV), polyanhydride, polyorthoester, poly (vinyl alcohol) (PVA), polyethylene glycol (PEG), polyurethane, polyacrylic acid (PAA), poly-N-isopropylacrylamide, diol/biacid-based aliphatic polyester and polyester-amide/polyester-urethane. More preferably, the synthetic polymer may be poly($\varepsilon$-caprolactone) (PCL), but is not limited thereto.

The poly($\varepsilon$-caprolactone) (PCL) is a synthetic polymer having a semi-crystalline powder form with a low melting point, and it melts easily compared to other polymers. In addition, the poly($\varepsilon$-caprolactone) (PCL) is a non-toxic and biocompatible material that exhibits very slow decomposition rates and is widely used as a material for scaffolds for tissue engineering.

The organic solvent may be selected from the group consisting of chloroform, hexafluoroisopropane, tetrahydrofuran, dimethylformamide, dichloromethane, acetone, dioxane, trifluoroethane and mixture thereof.

The aqueous fish collagen solution of the second step may be prepared by dissolving fish collagen of 10 to 70 parts by weight based on 100 parts by weight of water.

If the addition amount of the fish collagen is out of the range, the fish collagen does not dissolve homogeneously in water or a homogeneous fish collagen-PCL mixture solution cannot be obtained or homogeneous nanofibers cannot be produced.

The collagen may be collagen extracted from marine organisms, more preferably fish collagen, but is not limited thereto.

Collagen is a fibrous protein and a natural polymer which is the main component of the extracellular matrix in the connective tissue. This collagen plays a role in regulating the cell recognition and cell adhesion and proliferation, supports the tissues and organs, maintains the body shape surrounding the body surface and regenerates tissues. It can be processed into various forms such as a sponge, a fiber, a gel, a solution, a core material and a tubular material. Fish collagen is a natural polymer substance extracted from marine fish species. The collagen extracted from these marine organisms can undergo easily lower molecular peptidization than collagen extracted from mammals, and has excellent absorption into human body. In addition, the amino acid composition of collagen extracted from marine organisms is different from that of human collagen and can be easily distinguished by special antibodies.

However, collagen has a disadvantage in that it has a very low mechanical strength and is difficult to control the decomposition rate and gelation is difficult by using collagen alone.

The water is the most common solvent in nature and is more economical than organic solvents and does not show toxicity. The present invention demonstrates for the first time that water can be used among solvents that constitute a mixture solution used in the manufacture of nanofibers using electrospinning. Specifically, it is possible to prepare a mixture solution for electrospinning by dissolving a natural polymer in water without toxicity instead of an organic solvent exhibiting toxicity to the cells. Hereafter, other natural polymer in addition to fish collagen which can use water as a solvent may apply to the manufacture of nanofibers by electrospinning.

The mixture solution of the third step is prepared by adding the synthetic polymer solution of the first step so as to comprise the synthetic polymer of 6.3 to 8.5 parts by weight based on 100 parts by weight of the mixture solution. More specifically, poly($\varepsilon$-caprolactone) (PCL) solution 8.8 wt % prepared in the first step may be added in an amount of 71.4 to 97.1 parts by weight based on 100 parts by weight of the mixture solution, but it is not limited thereto. The fish collagen solution may be added in an amount of 2 to 20 parts by weight based on 100 parts by weight of the mixture solution, but it is not limited thereto.

If the amount of the synthetic polymer solution and the fish collagen aqueous solution added in the production of the mixture solution of the third step is out of the range, the electrospinning may not be properly performed or it may be difficult to produce homogeneous nanofibers during electrospinning.

The mixture solution of the third step is prepared by adding water so as to comprise water of 0.9 to 10 parts by weight based on 100 parts by weight of the mixture solution, but it is not limited thereto.

Also, the present invention provides a method of culturing three-dimensional cell comprising: a first step of dissolving a synthetic polymer in an organic solvent; a second step of dissolving a fish collagen in water to prepare an aqueous fish collagen solution; a third step of adding the aqueous fish collagen solution prepared in the second step to the synthetic polymer solution prepared in the first step, followed by mixing homogeneously; a fourth step of electrospinning a mixture solution prepared in the third step to prepare a nanofiber support; and a step of culturing cell on the nanofiber support prepared in the fourth step.

In addition, the present invention provides a method of culturing three-dimensional cell comprising: a step of mixing and culturing an alginate solution and cells; a step of adding a collagen solution to a cultured mixture to prevent cell detachment; and a step of adding the agarose solution to a mixture including collagen and allowing the mixture to stand, thereby inducing gelation.

More specifically, the method of three-dimensional cell culture may comprise mixing the alginate solution and the cells, and culturing at a temperature of 25 to 37° C. for 5 to 30 minutes; adding the collagen solution to the cultured mixture to prevent cell detachment at a temperature of 25 to 37° C. for 5 to 30 minutes; and adding the agarose solution to a mixture including collagen and allowing the mixture to stand for 5 to 30 minutes at a temperature of 4 to 25° C., thereby inducing gelation.

In the step of mixing and culturing the alginate solution and the cells, the incubation temperature and time range are the most preferable temperature and time range for minimizing the influence on the cells.

In the step of adding the collagen solution to the cultured mixture so as to prevent cell detachment, if the temperature and the time do not fall within the range, the collagen is not homogeneously mixed or the cell culture efficiency is lowered.

In addition, in the step of adding the agarose solution is added and allowing the mixture to stand, thereby inducing gelation, if the temperature and the time do not fall within the range, gelation may not be performed or cells may be damaged or killed.

The collagen may be marine-derived collagen, but is not limited thereto.

The alginate may be added in an amount of 0.5 to 2 parts by weight, more preferably 1 part by weight based on 100 parts by weight of the cultured mixture, but is not limited thereto.

The collagen may be added in an amount of 1 to 30 parts by weight, more preferably 7.5 to 10 parts by weight based on 100 parts by weight of the mixture, but is not limited thereto.

If the collagen solution comprises in amount out of the above range, the cells are not be encapsulated so that the cells escape from the gel or affect the growth ability of the cells.

Also, the agarose is added in an amount of 0.1 to 0.5 parts by weight, more preferably 0.125 parts by weight based on 100 parts by weight of the mixture, but is not limited thereto.

The agarose is a polysaccharide composed of galactose extracted from seaweed. It is mainly used as a cell culture medium and can be used in the form of a hydrogel because the hardness of the structure can be adjusted, so that it is possible to seed cells evenly inside the scaffold. Moreover, agarose can induce gelation by changing temperature without ion crosslinking or chemical crosslinking. However, if the agarose solution comprises in amount out of the above range, gelation may not be performed or cells may be damaged or killed.

The alginate, collagen and agarose added to the mixture may be added in the form of a storage solution, but are not limited thereto.

The alginate storage solution for preparing the mixture solution may be prepared by dissolving alginate in an amount of 1 to 10 parts by weight based on 100 parts by weight of distilled water. The agarose storage solution may be prepared by dissolving agarose in an amount of 1 to 3 parts by weight based on 100 parts by weight of distilled water. The collagen storage solution may be prepared by dissolving collagen in an amount of 20 to 30 parts by weight based on 100 parts by weight of distilled water, but is not limited thereto.

The cells that can be cultured by the three-dimensional cell culture method of the present invention can be selected from normal cells and cancer cells.

The cancer cells are solid cancer cell selected from the group consisting of ovarian cancer, breast cancer, gastric cancer, colon cancer, rectal cancer, lung cancer, liver cancer, prostate cancer, renal cancer, pancreatic cancer, thyroid cancer, uterine cancer, laryngeal cancer, hydrocephalus, laryngeal cancer, guinea, salivary gland cancer, esophageal cancer, osteosarcoma, tongue cancer, biliary cancer, glioma, bone cancer and unknown cause cancer, and the cell is a blood cancer cell selected from the group consisting of B cell lymphoma, T cell lymphoma, leukemia, and multiple myeloma, but is not limited thereto.

Further, the present invention provides a method of measuring cell activity comprising: a step of mixing and culturing an alginate solution and cells; a step of adding a collagen solution to a cultured mixture to prevent cell detachment; a step of adding an agarose solution to a mixture containing collagen and allowing the mixture to stand and induce gelation, and culturing the cells three-dimensionally; and analyzing growth, proliferation, death, differentiation and migration of cells cultured three-dimensionally.

In addition, the present invention provides a method of measuring sensitivity of anticancer drugs comprising: a step of mixing and culturing an alginate solution and cells; a step of adding a collagen solution to a cultured mixture to prevent cell detachment; a step of adding an agarose solution to a mixture containing collagen and allowing the mixture to stand and induce gelation, and culturing the cells three-dimensionally; and a step of analyzing cell viability by adding an anticancer drug to cells cultured three-dimensionally.

The present invention will be described more fully hereinafter with reference to the accompanying drawings, in which exemplary embodiments of the invention are shown.

<Example 1> Fabrication and Degree of Mixing Analysis of Nanofiber Support 1-1. Production of PCL Nanofiber Support Chloroform was added to polycaprolactone (average Mn 80,000, Sigma (St. Louis, Mo., USA); hereinafter referred to as PCL) and uniformly dissolved for 1 hour by using a magnetic stirrer to prepare a final 8.8 wt % PCL solution and then electrospun. The needle of the electrospining was connected to a wire mesh type collector (0.5 mm in wire diameter, 1×1 mm mesh size) under the conditions of 27 gauge, a scattering distance of 8 cm, a voltage of 11 kV, a fluid velocity of 0.5 mL/hr, temperature 21~22° C. and humidity of 40~45% and the spinning time was 60 to 120 minutes, preferably approximately 90 minutes. Then, a PCL nanofiber support was prepared by drying in an oven of 60° C. for 10 seconds to remove the residual solvent contained in the mat.

1-2. Production of Fish Collagen/PCL Nanofiber Support

Chloroform was added to polycaprolacton (average Mn 80,000, Sigma; hereinafter referred to as PCL) and uniformly dissolved for 1 hour using a magnetic stirrer to prepare a PCL solution of final 8.8 wt %. In addition, in order to prepare fish collagen stock solution, fish collagen (Fish collagen, Geltech, Busan, Korea) was added to distilled water and mixed in a test tube mixer (Vortex, Genie-2, 60 Hz, Scientific Industries, Bohemia, N.Y., USA) to prepare 20 wt % ($_C$ 20 wt %) fish collagen aqueous solution (20 wt % fish collagen stock solution; 20 wt % stock (S) solution; $S_C$ 20 wt %; $S_C$ 20%).

Then, the $S_C$ 20 wt % fish collagen stock solution was added to the 8.8 wt % PCL solution so as to be the final concentration of fish collagen of 0.1, 1 and 2 wt %, and the mixture was homogeneously mixed for 3 hours using a magnetic stirrer to prepare fish collagen/PCL mixture solution.

The fish collagen/PCL mixture solution of 0.1, 1 and 2 wt % prepared in the above was electrospun by using an electrospinning apparatus. The needles of electrospinning, were connected to a wire mesh type collector (0.5 mm in wire diameter, 1×1 mm mesh size) under the conditions of 27 gauge, a scattering distance of 8 cm, a voltage of 9 kV, a fluid velocity of 0.4 mL/hr, temperature 21~22° C. and humidity of 40~45%. The spinning time was 60 to 90 minutes, preferably approximately 70 minutes.

1-3. Mixing Degree Analysis of Fish Collagen/PCL Nanofiber Support Using Rhodamine In order to confirm the mixing of fish collagen and PCL, 0.01 g of rhodamine B (Sigma) was added to a fish collagen aqueous solution of $S_C$ 20 wt % and dissolved uniformly in a test tube mixer. Thereafter, a fish collagen aqueous solution of $S_C$ 20 wt % containing rhodamine B was added to 8.8 wt % PCL solution so that the final concentration of fish collagen was 1% by weight, and the mixture was stirred to prepare a rhodamine-1% fish collagen/PCL mixture solution.

A nanofiber support was prepared by electrospinning the rhodamine-1 wt % fish collagen/PCL solution prepared in the above under electrospinning conditions of Examples 1-2. The prepared rhodamine-1 wt % fish collagen/PCL nanofiber support was placed on a slide glass, sealed with a cover glass, and the degree of mixing was analyzed using a confocal laser scanning microscope.

As a result, as shown in FIG. 1, it was confirmed that the nanofibers constituting the support were well stained with rhodamine.

From the above results, it was confirmed that the fish collagen aqueous solution was homogeneously mixed with PCL.

<Example 2> Analysis of Cell Adhesion of PCL and Fish Collagen/PCL Nanofiber Support 2-1. Cell Culture Using PCL and Fish Collagen/PCL Nanofiber Support Thymic deep cortex or cortical reticular epithelial cell (hereafter, referred to as CREC), a type of normal mouse thymic epithelial cell (TEC) provided from Dr. Barbara B. Knowles (The Jackson Laboratory, Bar Harbor, Me., USA) was cultured and incubated in Dulbecco's Modified Eagle Medium (DMEM, HyClone, Logan, Utah, USA) containing 10% (v/v) fetal bovine serum (FBS; Gibco, Invitrogen), 100 IU/mL penicillin (Gibco, USA) and 100 μg/mL streptomycin (Gibco, Invitrogen) at 37° C. in a 5% $CO_2$ atmosphere. The culture medium was replaced with new one every 2-3 days.

The PCL nanofiber support prepared in Example 1 and the fish collagen/PCL nanofiber support having final concentrations of 0.1, 1 and 2 wt % were placed in 96-well plates respectively and CREC cells were inoculated at $5 \times 10^4$ cells per a well and cultured for 6 hours.

2-2. Analysis of Cell Adhesion of Nanofiber Support Using Fibrous Actin Staining In order to confirm the cell adhesion of the nanofiber support, the support having the cultured cells was washed twice with phosphate buffered saline (PBS) and fixed with 4% paraformaldehyde fixation solution at room temperature for 20 minutes. Thereafter, the cells were washed twice with PBS, and were infiltrated into 0.1% Triton-X100 solution at room temperature for 5 minutes and then washed twice with PBS.

To remove nonspecific staining, the cells were treated with 0.2% bovine serum albumin (BSA) solution at room temperature for 20 minutes and then washed twice with PBS.

Thereafter, actin-detecting Phalloidin-FITC (Promega, Madison, Wis., USA) was diluted to 1:150 in 0.2% BSA solution and reacted at room temperature for 40 minutes, and then was washed with tris-buffered saline (TBS), the support was placed on a cover glass and was contrast-stained with DAPI (Vector Lab, Inc., Burlingame, Calif., USA) for nuclear staining of the cells, and encapsulated. The cell adhesion of the cells for the support was measured by a laser confocal microscope.

As a result, as shown in FIG. 2, 1 wt % fish collagen-PCL nanofiber support exhibited similar adhesion to the PCL nanofiber support, and the 1 and 2 wt % fish collagen support significantly increased the cell adhesion than PCL nanofiber support, and the higher the concentration of fish collagen, the better the cell culture efficiency of support. Therefore, the following Examples confirmed that three-dimensional culture of cells optimized at a concentration of at least 2 wt % of fish collagen.

<Example 3> Analysis of Optimized Concentration of Fish Collagen 3-1. Production of Fish Collagen/PCL Nanofiber Support of a Concentration of 2 wt % or More Fish collagen was added distilled water to prepare fish collagen stock solutions ($S_c$) having the concentrations of $S_c$ 10 wt %, $S_c$ 20 wt %, $S_c$ 30 wt % $S_c$ 40 wt % $S_c$ 50 wt % $S_c$ 60 wt % $S_c$ 70 wt % $S_c$ 80 wt % $S_c$ 90 wt % and $S_c$ 100 wt %, and were named as $S_c$ 10%, $S_c$ 20%, $S_c$ 30% $S_c$ 40% $S_c$ 50% $S_c$ 60% $S_c$ 70% $S_c$ 80% $S_c$ 90% and $S_c$ 100%. In the case of $S_c$ 100%, the PCL cannot be included at all, so it is excluded from the selection condition (marked as X in Table 1), and the concentration of at least $S_c$ 80% is excluded from the selection condition because the viscosity is too high to add the accurate content (marked as X in Table 1). In addition, in the case of high concentration of at least $S_c$ 50%, $S_c$ 60% was also excluded from the selection condition because there is no particular difference with $S_c$ 50% or $S_c$ 70%.

Accordingly, the fish collagen stock solutions to be added to the mixture solution were prepared as $S_c$ 10%, $S_c$ 20%, $S_c$ 30%, $S_c$ 40%, $S_c$ 50% and $S_c$ 70%.

In addition, chloroform was added to PCL (polycaprolacton, average Mn 80,000, Sigma) and uniformly dissolved for 1 hour using a magnetic stirrer to finally prepare 8.8 wt % PCL solution.

Thereafter, fish collagen stock solutions having each concentration were added to the produced 8.8 wt % PCL solution to prepare fish collagen/PCL mixture solutions having final concentration of fish collagen in the mixed solution (FC) of $F_c$ 2 wt %, $F_c$ 3 wt %, $F_c$ 4 wt %, $F_c$ 5 wt %, $F_c$ 10 wt %, $F_c$ 15 wt %, $F_c$ 20 wt %, $F_c$ 30 wt %, $F_c$ 40 wt % and $F_c$ 50 wt %, and were named as $F_c$ 2%, $F_c$ 3%, $F_c$ 4%, $F_c$ 5%, $F_c$ 10%, $F_c$ 15%, $F_c$ 20%, $F_c$ 30%, $F_c$ 40% and $F_c$ 50%, respectively. Referring to the Table 1, the nanofiber support was not homogeneously produced or electrospun when it contained 1.1 mL or more of water based on the total volume of the mixture solution of 10 mL (number in parentheses in italics). Accordingly, it was confirmed that the nanofiber support was successfully prepared when the amount of water contained based on the total volume of the mixture solution of 10 mL was 0.09 to 1 mL (number in parentheses in italics).

Finally, the mixture solution prepared according to the amount of water in Table 1, the amount of fish collagen in Table 2, and the amount of the 8.8 wt % PCL synthetic polymer solution in Table 3 based on a total volume of 10 mL of the mixture solution, was electrospun to prepare a nanofiber support. The needles of electrospinning, were connected to a wire mesh type collector (0.5 mm in diameter, 1×1 mm mesh size) under the conditions of 27 gauge, a scattering distance of 8 cm, a voltage of 9 kV, a fluid velocity of 0.4 mL/hr, temperature 21~22° C. and humidity of 40~45%. The spinning time was 60 to 90 minutes, preferably approximately 70 minutes.

TABLE 1

| Content of water based on 10 mL of mixture solution (mL) | | Final concentration of fish collagen in mixture solution ($F_c$, %) | | | | | | | | | | |
|---|---|---|---|---|---|---|---|---|---|---|---|---|
| | | 2 | 3 | 4 | 5 | 10 | 15 | 20 | 30 | 40 | 50 | 100 |
| Concentration of fish collagen stock solution ($S_c$, %) | 10 | (1.8) | (2.7) | (3.6) | (4.5) | x | x | x | x | x | x | x |
| | 20 | 0.8 | (1.2) | (1.6) | (2) | (4) | x | x | x | x | x | x |
| | 30 | 0.47 | 0.7 | 0.93 | (1.17) | (2.33) | (3.5) | (4.67) | x | x | x | x |
| | 40 | 0.3 | 0.45 | 0.6 | 0.75 | (1.5) | (2.25) | (3) | (4.5) | x | x | x |
| | 50 | 0.2 | 0.3 | 0.4 | 0.5 | 1 | (1.5) | (2) | (3) | (4) | x | x |
| | 60 | 0.13 | 0.2 | 0.27 | 0.33 | 0.67 | 1 | (1.33) | (2) | (2.67) | (3.33) | x |
| | 70 | 0.09 | 0.13 | 0.17 | 0.21 | 0.43 | 0.64 | 0.86 | (1.29) | (1.71) | (2.14) | x |
| | 80 | x | x | x | x | x | x | x | x | x | x | x |
| | 90 | x | x | x | x | x | x | x | x | x | x | x |
| | 100 | x | x | x | x | x | x | x | x | x | x | x |

TABLE 2

| Content of fish collagen based on 10 mL of mixture solution (mL) | | Final concentration of fish colagen in mixture solution ($F_c$, %) | | | | | | | | | | |
|---|---|---|---|---|---|---|---|---|---|---|---|---|
| | | 2 | 3 | 4 | 5 | 10 | 15 | 20 | 30 | 40 | 50 | 100 |
| Concentration of fish collagen stock solution ($S_c$, %) | 10 | x | x | x | x | x | x | x | x | x | x | x |
| | 20 | 0.2 | x | x | x | x | x | x | x | x | x | x |
| | 30 | 0.2 | 0.3 | 0.4 | x | x | x | x | x | x | x | x |
| | 40 | 0.2 | 0.3 | 0.4 | 0.5 | x | x | x | x | x | x | x |
| | 50 | 0.2 | 0.3 | 0.4 | 0.5 | 1.0 | x | x | x | x | x | x |
| | 60 | 0.2 | 0.3 | 0.4 | 0.5 | 1.0 | 1.5 | x | x | x | x | x |
| | 70 | 0.2 | 0.3 | 0.4 | 0.5 | 1.0 | 1.5 | 2.0 | x | x | x | x |
| | 80 | x | x | x | x | x | x | x | x | x | x | x |
| | 90 | x | x | x | x | x | x | x | x | x | x | x |
| | 100 | x | x | x | x | x | x | x | x | x | x | x |

TABLE 3

| Content of 8.8 wt % PCL solution based on 10 mL of mixture solution (mL) | | Final concentration of fish collagen in mixture solution ($F_c$, %) | | | | | | | | | | |
|---|---|---|---|---|---|---|---|---|---|---|---|---|
| | | 2 | 3 | 4 | 5 | 10 | 15 | 20 | 30 | 40 | 50 | 100 |
| Concentration of fish collagen stock solution ($S_c$, %) | 10 | x | x | x | x | x | x | x | x | x | x | x |
| | 20 | 9.00 | x | x | x | x | x | x | x | x | x | x |
| | 30 | 9.33 | 9.00 | 8.67 | x | x | x | x | x | x | x | x |
| | 40 | 9.50 | 9.25 | 9.00 | 8.75 | x | x | x | x | x | x | x |
| | 50 | 9.67 | 9.40 | 9.20 | 9.00 | 8.00 | x | x | x | x | x | x |
| | 60 | 9.67 | 9.50 | 9.33 | 9.17 | 8.33 | 7.50 | x | x | x | x | x |
| | 70 | 9.71 | 9.57 | 9.43 | 9.29 | 8.57 | 7.86 | 7.14 | x | x | x | x |
| | 80 | x | x | x | x | x | x | x | x | x | x | x |
| | 90 | x | x | x | x | x | x | x | x | x | x | x |
| | 100 | x | x | x | x | x | x | x | x | x | x | x |

3-2. Analysis of Structure and Diameter of Fish Collagen/PCL Nanofiber Support According to Fish Collagen Concentration In order to confirm the surface structure of the PCL nanofiber support prepared in Example 1-1 and the fish collagen/PCL nanofiber support prepared in Example 3-1 by using a scanning electron microscope (SEM), each nanofiber support was fixed with 2.5% glutaraldehyde fixation liquid for 24 hours at 4° C. and then additionally fixed with 1% osmium tetroxide at room temperature for 1 hour. The Fixed support samples were washed 2-3 times with 0.1 M phosphate buffer (pH 7.4) and dehydrated by an ethanol series. Each of the dehydrated nanofiber support samples was frozen at −80° C. for 3 hours, freeze-dried for 12 hours using a vacuum freeze drier (FDS series, ilShinBioBase), and surface-treated by an ion sputter (E-1010, Hitachi, Tokyo, Japan), and the surface structure of the nanofiber support was analyzed by a scanning electron microscope (Hitachi) under an accelerating voltage of 20 kV. The diameter and nano/micro fiber distribution at 3000× magnification of the fish collagen/PCL nanofiber support of $F_c$ 2%-$S_c$ 50%, $F_c$ 3%-$S_c$ 50%, $F_c$ 4%-$S_c$ 50%, $F_c$ 5%-$S_c$ 50%, $F_c$ 10%-$S_c$ 50%, $F_c$ 3%-$S_c$ 70%, $F_c$ 5%-$S_c$ 70%, $F_c$ 10%-$S_c$ 70%, $F_c$ 15%-$S_c$ 70%, $F_c$ 20%-$S_c$ 70%, $F_c$ 2%-$S_c$ 20%, $F_c$ 2%-$S_c$ 30%, $F_c$ 2%-$S_c$ 40%, $F_c$ 4%-$S_c$ 40% was measured.

As a result, as shown in FIGS. 3, 4, 5 and 6, the fibers constituting the fish collagen/PCL nanofiber support were a nano/micro hybrid fiber composed of nanofibers having a nanometer diameter and micro fibers having a micrometer diameter. Therefore, even when a mixture solution of a PCL solution dissolved in an organic solvent such as chloroform and a fish collagen solution dissolved in water is electrospun into a polymer solution mixed with an organic solvent and water, a nano/micro hybrid fiber, It was confirmed that the fish collagen/PCL mat could be successfully obtained.

In addition, as a result of the microstructure of the supports having final fish collagen concentrations of $F_c$ 2%, $F_c$ 3%, $F_c$ 4%, $F_c$ 5% and $F_c$ 10% using the $S_c$ 50% stock solution by scanning electron microscope in FIG. 3, it was confirmed that as the final collagen concentration of the support increased, the size of the pores between the nanofibers decreased. Therefore, it was confirmed that as the final collagen concentration of the support increased, the average diameter of the nanofibers decreased.

As a result of the microstructure of the supports having final fish collagen concentrations of $F_c$ 2%, $F_c$ 3%, $F_c$ 4%, $F_c$ 5% and $F_c$ 10% using the $S_c$ 70% stock solution by scanning electron microscope, it was confirmed that as the final collagen concentration of the support increased, that the size of the pore decreased. Especially, in the case of the fish collagen/PCL nanofiber support having a high concentration of $F_c$ 5% or more in the support prepared using the $S_c$ 50% and $S_c$ 70% stock solutions, generally the pore size and the diameter of the nanofibers were too small to provide ideal environment for three-dimensional distribution of cells and thus the microstructure of the support was observed according to the concentration of the stock solution at $F_c$ 2% and $F_c$ 4%.

As a result, referring to FIG. 5, the average diameters of the $F_c$ 2% nanofibers were 1.47±0.6 μm ($S_c$ 20%), 1.31±0.7 μm ($S_c$ 30%), 1.28±0.7 μm ($S_c$ 40%) and 1.01±0.4 μm ($S_c$ 50%), respectively. Also, referring to FIG. 6, the average diameters of the $F_c$ 4% nanofibers were 1.53±1.0 μm ($S_c$ 40%) and 0.96±0.5 μm ($S_c$ 50%), respectively. Moreover, as shown in FIGS. 5 and 6, it was confirmed that as the concentration of $F_c$ 2% and $F_c$ 4% stock solution increased, the size of the pores decreased.

From the above results, it was confirmed that as the concentration of the stock solution increased in the support less than $F_c$ 5%, the average diameter and the pore of the nanofibers decreased.

<Example 4> Three-Dimensional Culture Characterization of Solid Cancer Cells According to Fish Collagen Concentration in Fish Collagen/PCL Nano/Micro Hybrid Fiber Support 4-1. Cell and Cell Culture A human non-small cell lung cancer cells (NCI-H1703) were purchased from the American Type Culture Collection (ATCC, Manassas, Va., USA) and a human prostate cancer cell -145 were purchased from Korean Cell Line Bank. NCI-H1703 and DU-145 cell lines were cultured and maintained in RPMI-1640 medium (HyClone, Logan, Utah, USA) containing 10% (v/v) fetal bovine serum (FBS; Gibco, Invitrogen), 100 IU/mL penicillin (Gibco, Invitrogen) and 100 ug/mL streptomycin (Gibco, Invitrogen) at 37° C. under atmospheric conditions containing 5% $CO_2$. The culture medium was changed with new one every 2-3 days.

4-2. Three-Dimensional Cell Culture Using Fish Collagen/PCL Nanofiber Support

In order to compare three-dimensional culture characteristics of fish collagen/PCL nanofiber support prepared according to the concentration of fish collagen, experimental groups were set as follows:

Experimental groups was divided into 10 groups of $F_c$ 0% (PCL 100%), $F_c$ 2%-$S_c$ 30%, $F_c$ 2%-$S_c$ 50%, $F_c$ 2%-$S_c$ 70%, $F_c$ 5%-$S_c$ 50%, $F_c$ 5%-$S_c$ 70%, $F_c$ 10%-$S_c$ 50%, $F_c$ 10%-$S_c$ 70%, $F_c$ 15%-$S_c$ 70%, $F_c$ 20%-$S_c$ 70% according to the concentration ($S_c$) of the fish collagen stock solution used for the production of the fish collagen/PCL mixture solution and final concentration of fish collagen ($F_c$) in the fish collagen/PCL mixture solution used in the electrospinning. The fish collagen/PCL nanofiber support was prepared according to the method of the fish collagen/PCL nanofiber support in the Example 1 and the fish collagen/PCL nanofiber support was placed on a 96-well plate and human non-small cell lung cancer (NCI-H1703) and human prostate cancer (DU-145) cells inoculated at 5×10$^4$ cells/well, respectively and cultured.

4-3. Three-Dimensional Characterization of Human Solid Cancer Cells Using Actin Staining A F-actin staining of human non-small cell lung cancer (NCI-H1703) and prostate cancer cell line (DU-145) cultured in a three-dimensional culture for 1 day using fish collagen/PCL nanofiber support was performed.

First, the cell-cultured fish collagen/PCL composite nanofiber support was fixed with 4% paraformaldehyde fixation liquid for 20 minutes at room temperature. Then, the cells were washed twice with PBS, infiltrated into 0.1% Triton-x 100 solution at room temperature for 5 minutes, and washed twice with PBS. To remove nonspecific staining, the cells were treated with 0.2% bovine serum albumin (BSA) solution at room temperature for 20 minutes and then washed twice with PBS. Thereafter, actin-detecting Phalloidin-FITC (Promega, Madison, Wis., USA) was diluted to 1:150 with 0.2% BSA solution and reacted for 40 minutes and washed with tris-buffered saline (TBS) three times to place on a slide. The cell were contrast-stained with DAPI (Vector Lab, Inc., Burlingame, Calif., USA) for nuclear staining of cells, covered with a cover glass and encapsulated to identify three-dimensional distribution of the cells in each nanofiber support by a confocal laser scanning microscope (FV1000-IX81, Olympus, Japan).

As a result, referring to FIG. 7, which is result of three-dimensional culture of human non-small cell lung cancer line (NCI-H1703) cells in PCL nanofiber support ($F_c$ 0%; PCL 100%) and FIG. 17, which is a result of three-dimensional culture of human prostate cancer cell, human non-small cell lung cancer cells (NCI-H1703) and human prostate cancer cell lines (DU-145) cells were found to extend from the surface of the nanofiber support into a depth of about 55 μm and 28 μm, respectively.

From the above results, it was confirmed that the pores between the nanofibers in the PCL nanofiber support ($F_c$ 0%) were relatively wide for the cells to reach to a considerably deep region. However, referring to FIGS. 7C and 17C showing the each cross section at 1 μm intervals, human non-small cell lung cancer (NCI-H1703) cells and human prostate cancer cell lines (DU-145) are observed to have a form of a round shape which is general form of unattached cells rather than stretching. In addition, almost none of culture characteristics related to the survival, proliferation and interaction of the cells, in which the cells were adhered to grow, and most of the cells were scattered.

While, Referring FIGS. 8, 9 and 10, as a result of three-dimensional culture of human non-small cell lung cancer (NCI-H1703), FIGS. 18, 19 and 20 as a result of three-dimensional culture of human prostate cancer cell line (DU-145) in fish collagen/PCL nanofiber support, it was confirmed that human lung cancer cells were introduced to the depth of about 42 μm from the surface of $F_c$ 2%-$S_c$ 30% fish collagen/PCL nanofiber support (FIG. 8). It was confirmed that human prostate cancer cells were introduced to the depth of about 58 μm from the surface of the nanofiber support (FIG. 18). Also, as for F $F_c$ 2%-$S_c$ 50% fish collagen/PCL nanofiber support, human lung cancer cells (FIG. 9) and human prostate cancer cell lines (DU-145) (FIG. 19) were introduced to the depth of about 36 μm and about at least 100 μm from the surface of the nanofiber support, respectively. In case of $F_c$ 2%-$S_c$ 70% fish collagen/PCL nanofiber support, human lung cancer cells (FIG. 10) and human prostate cancer cell lines (DU-145) (FIG. 20) were introduced to the depth of about 36 μm and about at least 100 μm from the surface of the nanofiber support, respectively.

From the above results, it was confirmed that the pores between the nanofibers were sufficiently large so that the $F_c$ 2%-$S_c$ 30%, $F_c$ 2%-$S_c$ 50% and $F_c$ 2%-$S_c$ 70% fish collagen/PCL nanofiber support could reach cells to a considerably deep region. In addition, referring FIGS. 8C, 9C and 10C, as a result of three-dimensional culture of human non-small cell lung cancer (NCI-H1703), FIGS. 18C, 19C and 20C as a result of three-dimensional culture of human prostate cancer cell line (DU-145), most cells cultured in $F_c$ 2%-$S_c$ 30%, $F_c$ 2%-$S_c$ 50% and $F_c$ 2%-$S_c$ 70% fish collagen/PCL nanofiber support have culture characteristics related to the survival, proliferation and interaction of the cells to be adhered to grow, and unlike the cell culture characteristics of the PCL nanofiber support ($F_c$ 0%) of FIG. 7C or FIG. 17C, no cells were found to be scattered independently.

Therefore, it was confirmed that the $F_c$ 2%-$S_c$ 30%, $F_c$ 2%-$S_c$ 50%, and $F_c$ 2%-$S_c$ 70% fish collagen/PCL nanofiber support provide an ideal three-dimensional cell growth environment, thereby exhibiting high three-dimensional cell culture efficiency.

Also, referring FIGS. 11 and 12, as a result of three-dimensional culture of human non-small cell lung cancer (NCI-H1703), FIGS. 21 and 22, as a result of three-dimensional culture of human prostate cancer cell line (DU-145) in $F_c$ 5%-$S_c$ 50% and $F_c$ 5%-$S_c$ 70% fish collagen/PCL nanofiber support, it was confirmed that human lung cancer cells were introduced to the depth of about 20 μm from the surface of $F_c$ 5%-$S_c$ 50% fish collagen/PCL nanofiber support (FIG. 11) and human prostate cancer cells were introduced to the depth of about 38 μm from the surface of the nanofiber support (FIG. 21). Also, as for $F_c$ 5%-$S_c$ 70% fish collagen/PCL nanofiber support, human lung cancer cells (FIG. 12) and human prostate cancer cell lines (DU-145) (FIG. 22) were introduced to the depth of about 24 μm and about 20 μm from the surface of the nanofiber support, respectively.

From the above results, it was confirmed that the pores between the $F_c$ 5%-$S_c$ 50% and $F_c$ 5%-Sc70% fish collagen/PCL nanofiber supports are narrower than those between the $F_c$ 2%-$S_c$ 30% and $F_c$ 2%-$S_c$ 50% so that the distribution is relatively shallow. However, as a result of checking each cross section at 1 μm intervals, it was homogeneously distributed as in the cells of FIGS. 8C and 9C above. In addition, referring FIGS. 11C and 12C, as a result of three-dimensional culture of human non-small cell lung cancer (NCI-H1703), FIGS. 21C and 22C, as a result of three-dimensional culture of human prostate cancer cell line (DU-145) in $F_c$ 5%-$S_c$ 50% and $F_c$ 5%-$S_c$ 70% fish collagen/PCL nanofiber support, most cells have culture characteristics related to the survival, proliferation and interaction of the cells to be adhered to grow, and unlike the cell culture characteristics of the PCL nanofiber support ($F_c$ 0%) of FIG. 7C or FIG. 17C, no cells were found to be scattered independently. Therefore, it was confirmed that the $F_c$ 5%-$S_c$ 50% and $F_c$ 5%-$S_c$ 70% fish collagen/PCL nanofiber support provide an ideal three-dimensional cell growth environment, thereby exhibiting high three-dimensional cell culture efficiency.

Also, referring FIGS. 13 and 14, as a result of three-dimensional culture of human non-small cell lung cancer (NCI-H1703), FIGS. 23 and 24, as a result of three-dimensional culture of human prostate cancer cell line (DU-145) in $F_c$ 10%-$S_c$ 50% and $F_c$ 10%-$S_c$ 70% fish collagen/PCL nanofiber support, it was confirmed that human lung cancer cells were introduced to the depth of about 22 μm from the surface of $F_c$ 10%-$S_c$ 50% fish collagen/PCL nanofiber support (FIG. 13) and human prostate cancer cells were introduced to the depth of about 22 μm from the surface of the nanofiber support (FIG. 23). Also, as for $F_c$ 10%-$S_c$ 70% fish collagen/PCL nanofiber support, human lung cancer cells (FIG. 14) and human prostate cancer cell lines (DU-145) (FIG. 24) were introduced to the depth of about 26 μm and about 22 μm from the surface of the nanofiber support, respectively.

From the above results, it was confirmed that the pores between the $F_c$ 10%-$S_c$ 50% and $F_c$ 10%-Sc70% fish collagen/PCL nanofiber supports are narrower than those between the $F_c$ 2%-$S_c$ 30% and $F_c$ 2%-$S_c$ 50% so that the distribution is relatively shallow. However, as a result of checking each cross section at 1 μm intervals, it was homogeneously distributed as in the cells of FIGS. 8C and 9C above. In addition, referring FIGS. 13C and 14C, as a result of three-dimensional culture of human non-small cell lung cancer (NCI-H1703), FIGS. 23C and 24C, as a result of three-dimensional culture of human prostate cancer cell line (DU-145) in $F_c$ 10%-$S_c$ 50% and $F_c$ 10%-$S_c$ 70% fish collagen/PCL nanofiber support, most cells have culture characteristics related to the survival, proliferation and interaction of the cells to be adhered to grow, and unlike the cell culture characteristics of the PCL nanofiber support ($F_c$ 0%) of FIG. 7C, no cells were found to be scattered independently. Therefore, it was confirmed that the $F_c$ 10%-$S_c$ 50% and $F_c$ 10%-$S_c$ 70% fish collagen/PCL nanofiber support provide an ideal three-dimensional cell growth environment, thereby exhibiting high three-dimensional cell culture efficiency.

Also, referring FIGS. 15 and 16, as a result of three-dimensional culture of human non-small cell lung cancer (NCI-H1703), FIGS. 25 and 26, as a result of three-dimensional culture of human prostate cancer cell line (DU-145) in $F_c$ 15%-$S_c$ 70% and $F_c$ 20%-$S_c$ 70% fish collagen/PCL nanofiber support, it was confirmed that human lung cancer cells were introduced to the depth of about 18 μm from the surface of $F_c$ 15%-$S_c$ 70% fish collagen/PCL nanofiber support (FIG. 15) and human prostate cancer cells were introduced to the depth of about 20 μm from the surface of the nanofiber support (FIG. 25). Also, as for $F_c$ 20%-$S_c$ 70% fish collagen/PCL nanofiber support, human lung cancer cells (FIG. 16) and human prostate cancer cell lines (DU-145) (FIG. 26) were introduced to the depth of about 26 μm and about 24 μm from the surface of the nanofiber support, respectively. From the above results, it was confirmed that the pores between the $F_c$ 15%-$S_c$ 70% and $F_c$ 20%-Sc70=fish collagen/PCL nanofiber supports are narrower than those between the $F_c$ 2%-$S_c$ 30% and $F_c$ 2%-$S_c$ 50% so that the distribution is relatively shallow. However, as a result of checking each cross section at 1 μm intervals, it was homogeneously distributed as in the cells of FIGS. 8C and 9C above. In addition, referring FIGS. 15C and 16C, as a result of three-dimensional culture of human non-small cell lung cancer (NCI-H1703), FIGS. 25C and 26C, as a result of three-dimensional culture of human prostate cancer cell line (DU-145) in $F_c$ 15%-$S_c$ 70% and $F_c$ 20%-$S_c$ 70% fish collagen/PCL nanofiber support, most cells have culture characteristics related to the survival, proliferation and interaction of the cells to be adhered to grow, and unlike the cell culture characteristics of the PCL nanofiber support ($F_c$ 0%) of FIG. 7C, no cells were found to be scattered independently. Therefore, it was confirmed that the $F_c$ 15%-$S_c$ 70% and $F_c$ 20%-$S_c$ 70% fish collagen/PCL nanofiber support provide an ideal three-dimensional cell growth environment, thereby exhibiting high three-dimensional cell culture efficiency. From the above results, the fish collagen/PCL nanofiber support comprising fish collagen having a final fish collagen concentration ($F_c$) of $F_c$ 2% or more in the $F_c$ 2%, $F_c$ 5%, $F_c$ 10%, $F_c$ 15% and $F_c$ 20% fish collagen/PCL mixture solution, has been demonstrated that it can be effectively used for three-dimensional culture of non-small cell lung cancer (NCI-H1703) and human prostate cancer cell line (DU-145). In particular, it was confirmed that $F_c$ 2%-$S_c$ 30% to $F_c$ 2%-$S_c$ 50% fish collagen/PCL nanofiber supports can be usefully used for three-dimensional culture of cells among fish collagen/PCL nanofiber support containing at least $F_c$ 2%.

<Example 5> Analysis of Three-Dimensional Culture Characteristics of Blood Cancer Cells According to the Content of Fish Collagen Concentration in Fish Collagen/PCL Nanofiber Support 5-1. Cell and Cell Culture Mouse T cell lymphoma cells (EL4) and mouse B cell lymphoma cells (A20) were purchased from the American Type Culture Collection (ATCC, Manassas, Va., USA). EL4 cell lines were cultured and maintained in Dulbecco's Modified Eagle Medium (DMEM, HyClone, Logan, Utah, USA) containing 10% (v/v) fetal bovine serum (FBS; Gibco, Invitrogen), 100 IU/ml penicillin (Gibco, Invitrogen) and 100 μg/mL streptomycin (Gibco, Invitrogen) at 37° C. under 5% $CO_2$-containing atmospheric conditions. The A20 cell line was cultured and maintained in RPMI-1640 medium (HyClone, Logan, Utah, USA) containing 10% v/v fetal bovine serum (FBS; Gibco, Invitrogen), 100 IU/mL penicillin (Gibco, Invitrogen) and 100 μg/mL streptomycin (Gibco, Invitrogen) at 37° C. under 5% $CO_2$-containing atmospheric conditions. The culture medium was replaced with new one every 2-3 days.

5-2. Three-Dimensional Cell Culture Using Fish Collagen/PCL Nanofiber Support

In order to compare three-dimensional culture characteristics of fish collagen/PCL nanofiber support prepared according to the concentration of fish collagen, experimental groups were set as follows:

Experimental groups was divided into 10 groups of $F_c$ 0% (PCL 100%), $F_c$ 2%-$S_c$ 30%, $F_c$ 2%-$S_c$ 50%, $F_c$ 2%-$S_c$ 70%, $F_c$ 5%-$S_c$ 50%, $F_c$ 5%-$S_c$ 70%, $F_c$ 10%-$S_c$ 50%, $F_c$ 10%-$S_c$ 70%, $F_c$ 15%-$S_c$ 70%, $F_c$ 20%-$S_c$ 70% according to the concentration ($S_c$) of the fish collagen stock solution used for the production of the fish collagen/PCL mixture solution and final concentration of fish collagen ($F_c$) in the fish collagen/PCL mixture solution used in the electrospinning. The fish collagen/PCL nanofiber support was prepared according to the method of the fish collagen/PCL nanofiber support in the Example 1 and the fish collagen/PCL nanofiber support was placed on a 96-well plate and Mouse T cell lymphoma cell line (EL4) and mouse B cell lymphoma cell line (A20) cells inoculated at 4×10⁵ cells/well, respectively and cultured.

5-3. Analysis of Three-Dimensional Distribution Characteristics of Mouse Blood Cancer Cells Using Actin Staining For fibrous actin (F-actin) staining of mouse B cell lymphoma cell line (A20) and mouse T cell lymphoma cell line (EL4) cultured three-dimensionally for 1 day and 3 days using a fish collagen/PCL nanofiber support, fish collagen/PCL composite nanofiber support having cultured cells was fixed with 4% paraformaldehyde fixation liquid for 20 minutes at room temperature. Then, the cells were washed twice with PBS, then infiltrated into a 0.1% triton-X 100 solution at room temperature for 5 minutes, and washed twice with PBS. To remove nonspecific staining, the cells were treated with 0.2% bovine serum albumin (BSA) solution at room temperature for 20 minutes and then washed twice with PBS. Thereafter, actin-detecting Phalloidin-FITC (Promega, Madison, Wis., USA) was diluted to 1:150 with 0.2% BSA solution and the cells were reacted for 40 minutes and washed with tris-buffered saline three times and con-trast-stained with DAPI (Vector Lab, Inc., Burlingame, Calif., USA) for nuclear staining of cells, covered with a cover glass to encapsulated to measure by a confocal laser scanning microscope FV1000-IX81, Olympus, Japan).

As a result of FIGS. 27 and 36, as three-dimensional culturing the mouse B cell lymphoma cell line (A20) in a PCL nanofiber support ($F_c$ 0%; PCL 100%) and three-dimensional culture of the mouse T cell lymphoma cell line (EL4), respectively, it was confirmed that the mouse B cell lymphoma cell line (A20) and the mouse T cell lymphoma cell line (EL4) cells were introduced to the depth of about 40 μm and about 40 μm from the surface of the nanofiber support, respectively.

From the above results, it was confirmed that the pores between the nanofibers in the PCL nanofiber support ($F_c$ 0%) were relatively wide and the cells reached a considerably deep region.

However, referring to FIGS. 27C and 36C showing the cross sections at 1 μm intervals, the number of cells distributed in the mouse B cell lymphoma cell line (A20) cells and the mouse T cell lymphoma cell line (EL4) F-actin was considerably small and was not homogeneously distributed along the cell membrane and the expression was greatly reduced or accumulated irregularly in the local region. The cell size was also smaller than that of normal cells and showed very irregular size and shape.

From the above results, it was confirmed that the PCL nanofiber support does not provide an environment suitable for three-dimensional culture of blood cancer cells.

While, Referring FIGS. 28, 29 and 30, as a result of three-dimensional culture of mouse B cell lymphoma cell line (A20), FIGS. 37, 38 and 39 as a result of three-dimensional culture of mouse T cell lymphoma cell line (EL4) in fish collagen/PCL nanofiber support, it was confirmed that mouse B cell lymphoma cells were introduced to the depth of about 66 μm from the surface of $F_c$ 2%-$S_c$ 30% fish collagen/PCL nanofiber support (FIG. 28). It was confirmed that mouse T cell lymphoma cells were introduced to the depth of about 60 μm from the surface of the nanofiber support (FIG. 37). Also, as for $F_c$ 2%-$S_c$ 50% fish collagen/PCL nanofiber support, B cell lymphoma cell line (FIG. 29) and mouse T cell lymphoma cell line (FIG. 38) were introduced to the depth of about 70 μm and about 80 μm from the surface of the nanofiber support, respectively. In case of $F_c$ 2%-$S_c$ 70% fish collagen/PCL nanofiber support, B cell lymphoma cell line (FIG. 30) and mouse T cell lymphoma cell line (FIG. 39) were introduced to the depth of about 110 μm and about 42 μm from the surface of the nanofiber support, respectively.

From the above results, it was found that $F_c$ 2%-$S_c$ 30%, $F_c$ 2%-$S_c$ 50% and $F_c$ 2%-$S_c$ 70% fish collagen/PCL nanofiber supports could reach cells to a considerably deep region and the sizes of the pores between the nanofibers were proper Is a suitable to provide an environment for migration and maintenance of cells. Also, when each cross section of 1 μm spacing was observed, the cells were homogeneously distributed at a sufficiently high density over a considerable thickness. In addition, referring to FIGS. 28C and 29C, as a result of three-dimensional culture of mouse B cell lymphoma cells and FIGS. 37C and 38C, as a result of three-dimensional culture of mouse T cell lymphoma cells, most cells of $F_c$ 2%-$S_c$ 30% and $F_c$ 2%-$S_c$ 50% nanofiber supports were distributed significantly different from those of the PCL nanofiber support ($F_c$ 0%) of FIG. 27C or 36C, and F-actin was homogeneously distributed along the cell membrane to reflect the round shape of the normal cell cortex, as well. In addition, the cells had the size similar to normal cells and showed a regular size and shape as whole.

Therefore, it was confirmed that the $F_c$ 2%-$S_c$ 30% and $F_c$ 2%-$S_c$ 50% fish collagen/PCL nanofiber supports provide an ideal three-dimensional cell growth environment, thereby exhibiting high three-dimensional cell culture efficiency.

On the other hand, in the case of $F_c$ 2%-$S_c$ 70% fish collagen/PCL nanofiber support, referring to FIGS. 30C and 39C, the size, shape and F-actin staining characteristics of cells are similar to those of normal cells; however the density between distributed cells was lower than $F_c$ 2%-$S_c$ 30% and $F_c$ 2%-$S_c$ 50% fish collagen/PCL nanofiber support. In addition, in the case of $F_c$ 5%-$S_c$ 50% (FIG. 31), $F_c$ 5%-$S_c$ 70% (FIG. 32), $F_c$ 10%-$S_c$ 70% (FIG. 33), $F_c$ 15%-$S_c$ 70% (FIG. 34) and $F_c$ 20%-$S_c$ 70% (FIG. 35) fish collagen/PCL nanofiber supports, it was confirmed that the mouse B cell lymphoma cells reached the depth of about 46 μm, 36 μm, 26 μm, 34 μm and 24 μm, respectively.

From the above results, it was confirmed that the pores between the $F_c$ 5%-$S_c$ 50%, $F_c$ 5%-$S_c$ 70%, $F_c$ 10%-$S_c$ 70%, $F_c$ 15%-$S_c$ 70% and $F_c$ 20%-$S_c$ 70% fish collagen/PCL nanofiber supports are narrower than those between the $F_c$ 2%-$S_c$ 30% and $F_c$ 2%-$S_c$ 50% so that the distribution is relatively shallow. However, the cells in the enlarged cross-section of FIGS. 31C, 32C, 33C, 34C and 35C were homogeneously distributed like the cells of Fc2%-Sc30% and Fc2%-Sc50% fish collagen/PCL nanofiber support, and the size, shape and F-actin staining characteristics of the cells were similar to those of normal cells.

However, the cell density was low as $F_c$ 2%-$S_c$ 70% fish collagen/PCL nanofiber support.

Mouse T cell lymphoma cells were found to reach 30 μm and 20 μm depth respectively in $F_c$ 5%-$S_c$ 50% (FIG. 40) and $F_c$ 5%-$S_c$ 70% (FIG. 41) fish collagen/PCL nanofiber supports, but in $F_c$ 10%-$S_c$ 70%, $F_c$ 15%-$S_c$ 70%, $F_c$ 20-$S_c$ 70% fish collagen/PCL nanofiber supports, the depth from the surface of the support is not large and the number of cells was also very small.

From the above results, it was confirmed that a good three-dimensional cell growth environment could not be provided in the supports at least $F_c$ 10% concentrations ($F_c$ 10%-$S_c$ 50%, $F_c$ 10%-$S_c$ 70%, $F_c$ 15%-$S_c$ 70%, $F_c$ 20%-$S_c$ 70%).

Therefore, through the above Examples of the present invention, fish collagen having a final fish collagen concentration ($F_c$) of $F_c$ 2% to $F_c$ 5% in $F_c$ 2%, $F_c$ 5%, $F_c$ 10%, $F_c$ 15% and $F_c$ 20% fish collagen/PCL mixture solutions, it was confirmed that the fish collagen/PCL nanofiber supports provide a culture environment suitable for three-dimensional cell culture, more preferably $F_c$ 2%-$S_c$ 30% to $F_c$ 2%-$S_c$ 50% fish collagen/PCL nanofiber supports are more suitable.

<Example 6> Measurement of Viability of Three-Dimensional Cells in Fish Collagen/PCL Nanofiber Support 6-1. Cell and Cell Culture Mouse B cell lymphoma cells (A20) were purchased from the American Type Culture Collection (ATCC, Manassas, Va., USA). The A20 cell line was cultured and maintained in RPMI-1640 medium (Gibco, Invitrogen (HyClone, Logan, Utah, USA) containing 10% v/v fetal bovine serum (FBS; Gibco, Invitrogen), 100 IU/mL penicillin (Gibco, Invitrogen) and 100 μg/mL streptomycin at 37° C. under atmospheric conditions containing 5% $CO_2$. The culture medium was replaced with new one every 1-2 days.

6-2. Three-Dimensional Cell Culture Using Fish Collagen/PCL Nanofiber Support

In order to measure the viability of three-dimensionally cultured cells in fish collagen/PCL nanofiber support, according to the concentration ($S_c$) of fish collagen stock used in the preparation of fish collagen/PCL mixture solution and final fish collagen concentration ($F_c$) using the electrospining in the fish collagen/PCL mixture solution, $F_c$ 0% (PCL100%) and $F_c$ 2%-$S_c$ 50% were used. The method of producing the fish collagen/PCL nanofiber support was performed in the same manner of manufacturing the fish collagen/PCL nanofibers of Example 1 above. Each nanofiber support was placed in a 96-well plate and A20 cells were inoculated at a concentration of $2 \times 10^5$ cells/well and cultured.

6-3. Live/Dead Staining

The Live/Dead staining was performed to confirm the effect of the support on the survival of A20 cells in the culture of the fish collagen/PCL nanofiber support according to the present invention.

First, A20 cells were inoculated in a fish collagen/PCL composite nanofiber support as in Example 6-2 and cultured for 2 days and 6 days. Each nanofiber support was washed once with PBS, diluted with 2 μL of calcein AM and 0.5 μL of ethidium (EthD-1) (LIVE/DEAD Viability Kit, Molecular Probes) in 1 ml of PBS to stain in the dark and analyzed by confocal laser scanning microscopy (FV1000-IX81, Olympus, Japan).

As a result, the viability of A20 cells cultured on the fish collagen/PCL nanofiber support according to the present invention was much higher than that of the PCL nanofiber support, as shown in FIG. 42 on the second day of culture and FIG. 43 on the sixth day of culture.

From the above results, it was confirmed that the fish collagen/PCL nanofiber support provides a proper growth environment for three-dimensional culture of A20 cells.

<Example 7> In-Vivo Mimetic Model Conformity Analysis of Three-Dimensional Cultured Cancer Cells Using Fish Collagen/PCL Nanofiber Support 7-1. Cell and Cell Culture Chemotherapy-sensitive human non-small cell lung cancer cells (NCI-H1703) were purchased from the American Type Culture Collection (ATCC, Manassas, Va., USA) and human prostate cancer cell (DU-145) were purchased from Korean Cell Line Bank. NCI-H1703 cell line and DU-145 cell line were cultured and maintained in in RPMI-1640 medium (HyClone, Logan, Utah, USA) containing 10% (v/v) fetal bovine serum (FBS; Gibco, Invitrogen), 100 IU/mL penicillin (Gibco, Invitrogen) and 10 μg/mL streptomycin (Gibco, Invitrogen) at 37° C. under atmospheric conditions containing 5% $CO_2$. Mouse T cell lymphoma cells (EL4) were purchased from the American Type Culture Collection (ATCC, Manassas, Va., USA). EL4 cell lines were cultured in Dulbecco's Modified Eagle Medium (DMEM, HyClone, Logan, Utah, USA) containing 10% (v/v) fetal bovine serum (FBS; Gibco, Invitrogen), 100 IU/ml penicillin (Gibco, Invitrogen) and 100 μg/mL streptomycin (Gibco, Invitrogen) at 37° C. under atmospheric conditions containing 5% $CO_2$. The culture medium was replaced with new one every 1-2 days.

7-2. Measurement of Drug Diffusion Ability of Cancer Cells Cultured Three-Dimensionally in Fish Collagen/PCL Nanofiber Support To measure the ability of the drug to reach cancer cells in a three-dimensional environment using a nanofiber support, $F_c$ 2%-$S_c$ 50% fish collagen/PCL nanofiber support was prepared, placed in a 96-well plate and EL4 cells were inoculated at 1×105 cells/well and cultured for 3 days.

After that, doxorubicin (Cell Signaling Technology, Danvers, Mass., USA) was treated at a concentration of 1 μM for 12 and 24 hours, washed with PBS, and the nucleus was stained with DAPI solution to confirm the distribution of doxorubicin in the support was confirmed by confocal laser microscopy (FV1000-IX81, Olympus, Tokyo, Japan). The results are expressed as mean±standard deviation (SD) for each analysis. Statistical analysis was performed using a two-tailed t-test and statistical significance was evaluated based on P<0.05.

As a result, as shown in FIG. 44, it was confirmed that doxorubicin was diffused into most regions where EL4 cells, which are mouse T lymphoma cells, were distributed in the support.

From the above results, it was confirmed that the three-dimensional cancer cell culture model using the fish collagen/PCL nanofiber support according to the present invention can be useful for screening for susceptibility testing of various drugs such as anticancer drugs.

7-3. Measurement of Anticancer Drug Susceptibility to Cancer Cells Cultured Three-Dimensionally in Fish Collagen/PCL Nanofiber Support In order to confirm the suitability of the three-dimensional cancer cell culture model using fish collagen/PCL nanofiber support, the sensitivity of three-dimensional cancer cell culture model using fish collagen/PCL nanofiber support to anticancer drug was analyzed.

First, an $F_c$ 4%-$S_c$ 50% fish collagen/PCL nanofiber support prepared in the same manner as in Example 1, was placed in a 96-well plate and NCI-H1703 and DU-145 cells were inoculated at a concentration of 5×10$^4$ cells/well. NCI-H1703 and DU-145 cells cultured in the conventional two-dimensional culture condition and NCI-H1703 and DU-145 cells cultured three-dimensionally in the nanofiber support were treated with 3 μM doxorubicin (Cell Signaling Technology, Danvers, Mass., USA) and 3 μM paclitaxel (T7402, Sigma) for 24 and 48 hours, respectively and with WST-1 reagent and the absorbance was measured at 450 nm using a microplate reader. The results are expressed as mean±standard deviation (SD) for each analysis. Statistical analysis was performed using a two-tailed t-test and statistical significance was evaluated based on P<0.05.

As a result, referring to FIG. 45A, when human non-small cell lung cancer (NCI-H1703) was treated with 3 μM doxorubicin for 24 hours, the cell viability was 55.1% (P<0.01) as compared with the control group in the two-dimensional environment and was 94.5% (P<0.01) as compared with the control group in the three-dimensional environment. After 48 hours, the viability was 40.8% (P<0.01) as compared with the control group in the two-dimensional environment and was 95.7% (P<0.01) as compared with the control group in the three-dimensional environment.

In addition, when prostate cancer cell line DU-145 was treated with 3 μM paclitaxel, the cell viability was 50.2% (P<0.01) as compared with the control group in the two-dimensional environment and was 93.5% (P<0.01) as compared with the control group in the three-dimensional environment in FIG. 45B. After 48 hours, the viability was 14.6% (P<0.01) as compared with the control group in the two-dimensional environment and was 64.2% (P<0.01) as compared with the control group in the three-dimensional environment.

Based on the above results, the three-dimensional environment exhibit effectively drug resistance to anticancer agents than the two-dimensional environment, and the three-dimensional cancer cell culture model using fish collagen/PCL nanofiber support can be used for drug resistance mechanism research and anticancer drug susceptibility test.

7-4. Analysis of Malignancy by Culturing Three-Dimensional Cancer Cells in Fish Collagen/PCL Nanofiber Support To analyze malignancy in a three-dimensional cancer cell culture model using a fish collagen/PCL nanofiber support, $F_c$ 4%-$S_c$ 50% fish collagen/PCL nanofiber support prepared in the same manner as in Example 1 was placed in a 96-well plate and DU-145 cells were inoculated at a concentration of 5×10$^4$ cells/well and cultured for 2 days. DU-145 cells were cultured in the same condition in two-dimensional manner as a control. A semi-quantitative reverse transcription-polymerase chain reaction analysis (RT-PCR) was performed.

First, total RNA was isolated from the cultured cells according to the manufacturer's instructions using trizol reagent (Ambion, Invitrogen) in each of the cultured DU-145 cells.

To analyze by RT-PCR, single-strand cDNA was synthesized from 1 μg of total RNA using 25 μL of buffer solution containing (DT) 0.5 μg oligo (dT) 12-18, Oligo (dT) primer, 50 mM Tris-HCl (pH 8.3), 75 mM KCl, 3 mM $MgCl_2$, 40 mM DTT, 0.5 mM deoxynucleotide triphosphate (dNTP) mixture, 10 units RNase inhibitor and 200 units Moloney murine leukemia virus (MMLV) reverse transcriptase (Promega, Madison, Wis., USA).

To confirm the PCR reaction for gene amplification, the primers of Table 4 were used. PCR reaction of human Hes1 and Notch-1, -2, -3, and 4 was performed by using 25 μl of a buffer solution containing 10 μmol of the primer and 1 μl cDNA sample, 20 mM Tris-HCl (pH 8.4), 50 mM KCl, 1.5 mM $MgCl_2$, 0.1% Triton X-100, 0.2 mM dNTP mixture liquid and 5 units of Taq DNA polymerase (Promega) to carry out Initial denaturation at 94° C. for 5 minutes, at 72° C. for 45 sec and at 72° C. for 45 sec for 35 cycles and CD44, Snail and GAPDH was performed at 94° C. for 30 sec, at 57° C. for 45 sec and at 72° C. for 45 sec and 30 cycles. In the case of human slug, HIF-1α, VEGF, and endothelin-1, initial denaturation was performed at 94° C. for 5 minutes, followed by 30 seconds at 94° C., 45 seconds at 60° C., and 45 seconds at 72° C. After the PCR reaction, the reaction product samples produced by 2% agarose gel electrophoresis were stained with EtBr (Ethidium bromide) and analyzed under UV light illumination.

As a result, as shown in FIG. 46, three-dimensional culture of human prostate cancer cells (DU-145) using two-dimensional or fish collagen/PCL nanofiber support was performed. As a result of Hes 1 and Notch-1, -2, -3, and 4 by RT-PCR analysis, the expression of Hes 1 and Notch-1, -2, -3, and 4 was increased in cancer cells cultured in a three-dimensional environment than two-dimensional culture.

From the above results, it was confirmed that, in contrast to the two-dimensional environment, the cancer cells cultured in the three-dimensional environment increase malignancy and the three-dimensional cancer cell culture model using the fish collagen/PCL nanofiber support according to the present invention environment was well simulated as a living body (in-vivo).

In addition, as shown in FIG. 47, the expression of cancer cells of snails and slugs, which are makers closely related to malignancies of cancer cells, especially epithelial-mesenchymal transition (EMT), VEGF which is a vascular endothelial growth factor of cancer cells, VEGF secretion factor HIF-1α, CD44, which is an important marker of cancer stem cell, and endothelin-1, which plays a key role in tumor growth and metastasis, was higher in the three-dimensional culture than the two-dimensional culture.

From the above results, in the case of three-dimensional cancer cell culture based on fish collagen/PCL nanofiber support, the culture environment of cancer cells such as growth, progression, metastasis and malignancy of cancer can exhibit characteristics very similar to a living body. Because the three-dimensional cell culture method using the nanofiber support of the present invention provides in-vivo simulation environment which cannot be provided in the conventional two-dimensional cell culture method, it is useful for development of therapeutic agent for cancer cells as well as the research on cancer cell, growth, metastasis and malignancy of cancer cells.

TABLE 4

| Gene | SEQ ID No. | Primer Sequence |
|---|---|---|
| Human Hes 1 | 1 | Forward: 5'-CCTGTCATCCCCGT CTACAC-3' |
|  | 2 | Reverse: 5'-CACATGGAGTCCGC CGTAA-3' |
| Human Notch-1 | 3 | Forward: 5'-TACAAGTGCGACTG TGACCC-3' |
|  | 4 | Reverse: 5'-CACACGTAGCCACT GGTCAT-3' |
| Human Notch-2 | 5 | Forward: 5'-CAACCGCAATGGAG GCTATG-3' |
|  | 6 | Reverse: 5'-GCGAAGGCACAATC ATCAATGTT-3' |
| Human Notch-3 | 7 | Forward: 5'-TGGCGACCTCACTT ACGACT-3' |
|  | 8 | Reverse: 5'-CACTGGCAGTTATA GGTGTTGAC-3' |
| Human Notch-4 | 9 | Forward: 5'-CCTGGCTCCTTCAA CTGCC-3' |
|  | 10 | Reverse: 5'-GCAAGTAGGTCCAG ACAGGT-3' |
| Human Snail | 11 | Forward: 5'-AGACCCACTCAGAT GTCAA-3' |
|  | 12 | Reverse: 5'-CATAGTTAGTCACA CCTCGT-3' |
| Human Slug | 13 | Forward: 5'-GGTCAAGAAGCATT TCAAC-3' |
|  | 14 | Reverse: 5'-GGTAATGTGTGGGT CCGA-3' |
| Human VEGF | 15 | Forward: 5'-CGAAACCATGAACT TTCTGC-3' |
|  | 16 | Reverse: 5'-CCTCAGTGGTCACA CACTCC-3' |
| Human HIF-1α | 17 | Forward: 5'-GGCGCGAACGACAA GAAAA-3' |
|  | 18 | Reverse: 5'-GTGGCAACTGATGA GCAAGC-3' |
| Human CD44 | 19 | Forward: 5'-CTCCAGTGAAAGGA GCAGCA-3' |
|  | 20 | Reverse: 5'-AGCAGGGATTCTGT CTGTGC-3' |
| Human Endothelin-1 | 21 | Forward: 5'-TGCTCCTGCTCTTC CCTGATGGATAAAGAGTGTGTC-3' |
|  | 22 | Reverse: 5'-GGTCACATAACGCT CTCTGGAGGGCTT-3' |
| Human GAPDH | 23 | Forward: 5'-TGGAGAAACCTGCC AAGTATG-3' |
|  | 24 | Reverse: 5'-TTGTCATACCAGGA AATGAGC-3' |

<Example 8> In-Vivo Simulation Induction/Growth and Cancer Cell Differentiation Suitability Analysis for Three-Dimensionally Cultured Cancer Cells Using Fish Collagen/PCL Nanofiber Support 8-1. Cell and Cell Culture Mouse T cell lymphoma cells (EL4) were purchased from the American Type Culture Collection (ATCC, Manassas, Va., USA).

EL4 cell lines were cultured in Dulbecco's Modified Eagle Medium (DMEM, HyClone, Logan, Utah, USA) containing 10% (v/v) fetal bovine serum (FBS; Gibco, Invitrogen), 100 IU/mL penicillin (Gibco, Invitrogen) and 100 μg/mL streptomycin (Gibco, Invitrogen) at 37° C. under atmospheric conditions containing 5% $CO_2$. The culture medium was replaced with new one every 2-3 days.

8-2. Analysis by High-Flow Cytometer

To analyze the ability of cancer stem cell formation and cancer cell differentiation in a three-dimensional cancer cell culture model using fish collagen/PCL nanofiber support, $F_c$ 2%-$S_c$ 50% nanofiber support was prepared in the same manner as in Example 1 and was placed in a 96-well plate and EL4 cells were inoculated at a concentration of $2 \times 10^5$ cells/well and cultured for 2 days.

The cultured cells were separated and washed twice with Hank's Balanced Salt Solution (HBSS, GibcoLife Technologies), resuspended in 3 mL of FACS buffer (0.1% BSA, 0.1% sodium chloride, 500 mL of HBSS) and centrifuged at 4° C. and 1500 rpm for 4 minutes and the supernatant was removed and the cell was resuspended and pre-incubated with anti-FcγRII/III (2.4G2, hybridoma supernatant) to avoid nonspecific binding with antibodies.

Thereafter, the primary fluorescent-labeled primary anti-mouse monoclonal antibody such as anti-CD4 antibody conjugated with FITC or PE (FITC-CD4 or PE-CD4), APC-conjugated anti-CD8 antibody (APC-CD8), c-kit-conjugated anti-c-kit antibody (c-kit-PE-CY7-c-kit) and APC-conjugated anti-sca-1 antibody (APC-sca-1) was reacted at a concentration of 5-10 μg/mL for 30 minutes under ice-cooling. Background fluorescence was determined by cells reacted with isotype-matched nonreactive antibodies.

After the cells were washed twice with HBSS, the cells were resuspended in 500 μL of FACS buffer and the expression of cell surface molecules was analyzed by Dot-plot method using a flow cytometer. The obtained results were analyzed using FlowJo software (Tree Star, Ashland, Oreg., USA).

As a result, as shown in FIG. 48, the ratio of c-kit$^+$sca-1$^+$ cells corresponding to cancer stem cells among the EL4 cells cultured for 2 days under the 2D environment was 0.97%; however the ratio of c-kit$^+$sca-1$^+$ cancer stem cells in EL4 cell cultured for 2 days under the 3D environment increased to 4.45%.

From the above results, it was confirmed that, in the case of three-dimensional cancer cell culture based on fish collagen/PCL nanofiber support, the culture environment of cancer cells related to the formation and growth of cancer stem cells is similar to that of a living body. Because the three-dimensional cell culture method using the nanofiber support of the present invention provides in-vivo simulation environment which cannot be provided in the conventional two-dimensional cell culture method, it can be used as a culture model useful for researches of cancer stem cell and anticancer drug resistance mechanism and development of highly efficient chemotherapy.

The following reference examples are intended to provide reference examples commonly applied to Examples 9 to 20.

<Reference Example 1> Cell and Cell Culture

The types of cell lines used in the following examples are as follows. A chemotherapy-sensitive human ovarian cancer cell line A2780 was purchased from the Sigma-Aldrich (Saint Louis, Mo., USA) and the mouse T cell lymphoma cell line (EL4) was purchased from American Type Culture Collection (ATCC, Manassas, Va., USA). In addition, a chemotherapy-sensitive human ovarian cancer cell line R182 cells were provided from Dr. J. Shah (Memorial Sloan-Kettering Cancer Center, New York, N.Y., USA) and a thymic deep cortex or cortical reticular epithelial cell (CREC) which is one of normal mouse thymic epithelial cell is provided from Dr. Barbara B. Knowles (The Jackson Laboratory, Bar Harbor, Me., USA). R182 cells and A2780 cell lines were cultured and maintained in RPMI-1640 medium (HyClone, Logan, Utah, USA) containing 10% (v/v) fetal bovine serum (FBS; Gibco, Invitrogen), 100 IU/mL penicillin (Gibco, Invitrogen) and 100 μg/mL streptomycin (Gibco, Invitrogen) at 37° C. under atmospheric conditions containing 5% $CO_2$. The culture medium was replaced with new one every 2-3 days.

In addition, CREC and EL4 cell lines were cultured and maintained in Dulbecco's Modified Eagle Medium (DMEM, HyClone, Logan, Utah, USA) containing 10% (v/v) fetal bovine serum (FBS; Gibco, Invitrogen), 100 IU/mL penicillin (Gibco, Invitrogen) and 100 μg/mL streptomycin (Gibco, Invitrogen) at 37° C. under atmospheric conditions containing 5% $CO_2$. The culture medium was replaced with new one every 2-3 days.

<Reference Example 2> Statistical Analysis

All results are expressed as mean±SD (SD) for each analysis. Statistical analysis was performed using a two-tailed t-test and statistical significance was evaluated based on $P<0.05$.

<Example 9> Fabrication of Agarose-Collagen-Alginate Composite Hydrogel Support

The hydrogel support was prepared in the same manner as in FIG. 49. To prepare a hydrogel support, stock solution was prepared by dissolving sodium alginate (Sigma-Aldrich) in distilled water for 16 hours at a concentration of 3% by weight and sterilized and agarose (Affymetrix, Cleveland, Ohio, USA) was added to sterilized distilled-water to be an amount of 2% by weight and heated at 100° C. until boiling to make agarose stock solution. In addition, marine organism derived collagen (hereinafter referred to as "marine collagen", Geltech, Busan, Korea) was added to distilled water in an amount of 25% by weight and vortexed to prepare a marine collagen storage solution.

Each of the solutions prepared by the above method was mixed at a temperature of 25° C. to 37° C. First, the cells are mixed with 33.3 μL of 3 wt % alginate stock solution and with 30 μL or 40 μL of 25 wt % marine collagen stock solution and finally 6.25 μL of 2 wt % agarose stock solution to be final concentrations of alginate of 1 wt %, marine collagen of 7.5 wt % or 10 wt % and agarose of 0.125 wt % (hereinafter referred to as "0.125 wt % agarose-7.5 wt % marine collagen-1 wt % alginate" or "0.125 wt % agarose-10 wt % marine collagen-1 wt % alginate"). Thereafter, the mixture obtained in the above allowed to stand at 4° C. for 5 to 30 minutes, more preferably at 5 to 10 minutes.

The three-dimensional cell culture using the hydrogel support of the present invention can be prepared by directly introducing the mixture into a culture container to be used for cell culture, inducing gelation of the mixture and culturing the cell, or transferring the gel to another container, i.e. as the method of FIG. 50, in which the end of a 1 mL syringe was cut and then the mixture was injected therein to induce gelation and transferred the gel into a 24-well plate using a piston of a syringe to culture the cells.

Therefore, the hydrogel of the present invention can prepare the gel according to the size and shape of the cell culture container, and the three-dimensional cell culture is possible by using the prepared hydrogel support.

<Example 10> Cell Cytotoxicity Sssay by $Ca^{2+}$ Cation

The cytotoxicity assay was performed by the conventional method [H. Lee et al., Regul. Pept. (2008), 147, 72-81]. The cells of Reference Example 1 were dispensed in a 96-well plate at a concentration of $1 \times 10^4$ cells/well for R182 and A2780 cells together with 0.1 mL of 10% FBS containing cell medium, and a concentration of $1 \times 10^5$ cells/well for R182 and A2780 cells, and the cells were cultured for 24 hours and then cultured for 12-16 hours in the absence of FBS.

The cultured cells were treated with various concentrations of calcium chloride ($CaCl_2$, Sigma-Aldrich) at concentrations of 10, 50, 100, 200 and 300 mM and cultured for 18 to 24 hours to perform WST-1 assay (EZ-Cytox Cell Viability Assay kit, Daeillab Service, Seoul, Korea) for cell cytotoxicity assay.

WST-1 reagent of 10 μL was added to each well and incubated for 2 hours in a humidified incubator at 37° C. and 5% $CO_2$ and the absorbance was measured at 450 nm using a microplate reader (Tecan, M, Switzerland) to calculate the percent growth rate.

Also, all results were also expressed as mean±SD (SD) for each analysis. Statistical analysis was performed using a two-tailed t-test and statistical significance was evaluated based on $P<0.05$.

As a result, as shown in FIG. 51, in case of the treatment of CREC cells with $CaCl_2$, a dose-dependent cytotoxic effect exhibited 81.1% at a concentration of 10 mM, 36.8% ($P<0.001$) at 50 mM, 23.0% ($P<0.001$) at 100 mM, 9.9% ($P<0.001$) at 200 mM and 10.3% ($P<0.001$) at 300 mM. In case of the treatment of mouse T cell lymphoma cells (EL4) with $CaCl_2$, a dose-dependent cytotoxic effect exhibited 101.3% at a concentration of 10 mM, 59.2% ($P<0.001$) at 50 mM, 25.4% ($P<0.001$) at 100 mM, 11.2% ($P<0.001$) at 200 mM and 9.7% ($P<0.001$) at 300 mM.

In addition, the human ovarian cancer cell, R182 cells showed 34.1% ($P<0.001$), 26.4% ($P<0.001$), 21.1% ($P<0.001$), 21.4% ($P<0.001$), 24.9% ($P<0.001$) and 25.6% ($P<0.001$) at 50 mM, 100 mM, 150 mM, 200 mM, 250 mM and 300 mM of $CaCl_2$, respectively and very strong cytotoxic effects at all concentrations above 50 mM. The other types of human ovarian cancer cells, A2780 cells showed 74.9%, 65.9%, 41.5% ($P<0.05$), 37.9% ($P<0.05$), 39.5% ($P<0.05$) and 43.7% ($P<0.05$) at 50 mM, 100 mM, 150 mM, 200 mM, 250 mM and 300 mM of $CaCl_2$, respectively and namely dose-dependent cytotoxic effect.

From the above results, it was confirmed that $CaCl_2$ shows a significant cytotoxic effect on various types of solid cancer and blood cancer cells as well as normal cells at a general concentration. From the above, because $CaCl_2$, which is widely used as a hardening agent in the gelation process, i.e. an essential step in the production of an alginate-based hydrogel cell culture support as a general material of hydrogel-based cell culture support, acts as strong toxic factor for both normal and cancer cells, it is very important to develop a method for gelation of a hydrogel which can reduce or eliminate such side effects.

<Example 11> Characterization of Agarose-Collagen-Alginate Composite Hydrogel Support by Material and Composition To identify the composition of suitable materials for preparing composite hydrogel support of Example 9, agarose sole hydrogel, agarose-alginate composite hydrogel and agarose-collagen-alginate composite hydrogel were prepared in the same manner as in Example 9, and their characteristics were analyzed.

The agarose sole hydrogel was prepared at concentrations of 0.5, 1, 1.5, and 2 wt %, which are conventionally used, and the agarose-alginate composite hydrogel was prepared by mixing 3 wt % alginate stock solution and 2 wt % agarose stock solution to be the concentration of 1 wt % alginate and 0.125 wt % agarose, and agarose-collagen-alginate composite hydrogel were prepared in the same manner as in Example 9.

For cell culture in each hydrogel support prepared by the above method, as Example 9, A2780 cells were added into 0.5, 1 and 1.5 wt % agarose sole hydrogel and 0.125 wt % agarose-1 wt % alginate complex a hydrogel support, placed in a 96-well plate to induce the gelation at 4° C. for 5 to 10 minutes and incubated in a medium, and the cell morphology was observed by a phase contrast microscope on days 1, 3 and 5 after the culture. In addition, EL4 cells were added to 0.5, 1.5, and 2 wt % agarose sole hydrogel supports, and placed in 96-well plates to induce the gelation at 4° C. for 5-10 minutes and incubated in a medium, and the cell morphology was observed by a phase contrast microscope on days 2, 5 and 10 after the culture.

As a result, as shown in FIG. 52, when the A2780 cells were cultured in agarose sole hydrogel support, the number of dead cells increased according to the lapse of the cell culture period, and in case of the agarose hydrogels of 0.5, 1 and 1.5 wt %, the number of dead cells all increased after 72 hours. In the case of the alginate-agarose composite hydrogel support, there were almost no dead cells, but the hydrogels had weak mechanical strength, so that the cells could not be stably bound to the gel escape out of the gel.

As shown in FIG. 53, as a result of three-dimensionally culturing of EL4 cells in agarose sole hydrogel supports at various concentrations and incubation times, in the case of agarose sole hydrogel supports, as higher the concentration of agarose and longer the cell culture period, the growth of EL4 cells decreased and the number of apoptotic cells increased. At 0.5 wt % agarose, the cell growth became slow on day 2, and from day 5, the growth almost did not occur and the number of dead cells increased. Also, at 1 wt % agarose, the cell growth was slower than 0.5 wt % agarose, and the number of dying cells was more increased and the 1.5 wt % agarose also showed a decrease in the cell growth and the number of dead cells. Particularly, at 2 wt % agarose, the growth of cells was hardly observed from day 2 after culturing and all the cells were observed to be dying over time.

On the other hand, as shown in FIGS. 54 and 55, in the agarose-collagen-alginate composite hydrogel support prepared according to the present invention, when animal collagen was added to be a final concentration of 0.05 wt % in a mixture solution, EL4 cells of about 4,500 escaped out of the gel. In case of marine collagen, the number of detached cells was 230, 20500, 18000, 17500, 11500, 5500 and 4000 at final concentrations 0.05 wt %, 0.1 wt %, 0.2 wt %, 0.5 wt %, 1 wt %, 2 wt % and 5 wt %, respectively.

From the above results, the survival and growth of A2780 and EL4 cells in the agarose-alginate composite hydrogel support was superior to that of the agarose sole hydrogel support, and the agarose-collagen-alginate composite hydrogel support exhibited a more stable cell binding force than the agarose-alginate composite hydrogel support.

Therefore, the cell culture using the agarose-collagen-alginate composite hydrogel support is superior to agarose sole hydrogel in the cell survival and growth, and solves the cell detachment phenomenon of the agarose-alginate composite hydrogel support having weak mechanical strength, thereby confirming very suitable for three-dimensional cell culture.

<Example 12> Characterization of Used Animal Collagen or Marine Collagen

As described in the above Examples, in the case of the three-dimensional cell culture method using the agarose-alginate composite hydrogel support, it was confirmed that the cells were detached out of the gel. However, the problem of cell detachment was solved by a three-dimensional cell culture method using an agarose-collagen-alginate composite hydrogel support to which the collagen was added and therefore, in order to confirm the efficiency of the collagen, the effect of animal collagen and marine collagen was analyzed.

According to the method of Example 9, 0.125 wt % agarose-0.05 wt % rat tail collagen-1.0 wt % alginate and 0.125 wt % agarose-(0.05, 0.1, 0.2, 0.5, 1, 2, 5, and 10 wt %) marine collagen-1.0 wt % alginate composite hydrogel support was prepared and EL4 cells of $5 \times 10^4$ cells/gel were included in the preparation of each of these hydrogel supports. Subsequently, 80 μL of the mixture solution was introduced into a 1 mL syringe to induce the gelation at 4° C. for 5 to 10 minutes and cultured in a 48-well plate, and observed by a phase contrast microscope on day 1, 2, 3 and 4 after culturing in FIG. 56.

In addition, 0.125 wt % agarose-0.05 wt % rat tail collagen-1.0 wt % alginate and 0.125 wt % agarose-(0.05, 0.1, 1, 3, 5, 7.5, 10 and 15 wt %) marine collagen-1.0 wt % alginate composite hydrogel support was prepared, and A2780 cells were included in the preparation of each of these hydrogel supports. Subsequently, the mixture solution was introduced into a 96-well plate to induce the gelation 4° C. for 5 to 10 minutes and a medium was added to culture and cells were observed by a phase contrast microscope on day 1 and 3 after culturing in FIG. 57.

As a result, as shown in Figure of EL4 cells and FIG. 57 of A2780 cells, two types of agarose-collagen-alginate composite hydrogel supports using 0.05 wt % animal collagen and 5-10 wt % marine collagen showed the same effect on the cell growth. In the case of marine collagen, marine collagen should be used at a concentration about 100 times higher than that of animal collagen in order to exhibit the same effect as animal collagen. However, since marine collagen is about 10,000 to 100,000 times cheaper than animal collagen, it was confirmed that the agarose-collagen-alginate composite hydrogel support exhibited similar effects to the composite hydrogel support using an animal collagen and could be used economically and very usefully.

<Example 13> Determination of Transparency of Agarose-Marine Collagen-Alginate Composite Hydrogel Support In order to determine the transparency of the agarose-marine collagen-alginate composite hydrogel support, EL4 cells were added to 0.125 wt % agarose-10 wt % marine collagen-1 wt % alginate composite hydrogel support prepared by the method of Example 9, hydrogel support prepared by chemical cross-linking of 100 mM $CaCl_2$, and a 96-well conventional plate for two-dimensional cell culture, at $4 \times 10^4$ cells/gel, respectively and were cultured to measure and compare the transparency of each support by a phase contrast microscope.

As a result, unlike the hydrogel support prepared by a commonly used ionic chemical crosslinking method (b) and the nanofiber support prepared by electrospinning, which is widely used in tissue engineering (c), as can be seen from the two-dimensional cell culture (a), the agarose-marine collagen-alginate composite hydrogel support (d) according to the present invention provides very high transparency to observe the morphology of EL4 cells using a phase contrast microscope easily. Therefore, the agarose-marine collagen-alginate composite hydrogel support of the present invention can observe by a phase contrast microscope various types of cells, which is impossible in an alginate-based hydrogel or a nanofiber-based support crosslinked with ions such as calcium in the three-dimensional cell culture.

<Example 14> Analysis Physical Properties of Agarose-Marine Collagen-Alginate Cmposite Hydrogel Support 1. Preparation of Hydrogel Support As experimental groups used for analyzing the structure of the support, first, 1 wt % alginate alone hydrogel, second, 0.125 wt % agarose sole hydrogel, third, 7.5 wt % marine collagen sole hydrogel, fourth, 10 wt % marine collagen sole hydrogel, fifth, 0.125 wt % agarose-1 wt % alginate composite hydrogel, sixth, 0.125 wt % agarose-7.5 wt % marine collagen-1 wt % alginate composite hydrogel seventh, 0.125 wt % agarose-10 wt % marine collagen-1 wt % alginate composite hydrogel was prepared as Example 9.

2. Analysis of Hydrogel Support Structure by Scanning Electron Microscope

The hydrogel supports of 7 experimental groups prepared in Example 14-1 were dispensed in a 1 mL syringe at 100 μL, respectively to induce the gelation at 4° C. for 5 to 10 minutes and the cells were frozen at −20° C. for 24 hours and dried by a vacuum freeze dryer (FDS series, ilShinBioBase) for 24 hours and surface-treated with ion sputter (E-1010, Hitachi, Japan) and observed by a scanning electron microscope (JSM-6490LV, JEOL, Japan) under an accelerating voltage of 20 kV.

As a result, when the cross sections of 1 wt % alginate, 0.125 wt % agarose, 7.5 and 10 wt % marine collagen sole hydrogel and 0.125 wt % agarose-1 wt % alginate composite hydrogel support were composed of an irregular pore structure as a whole, however the cross sections of 0.125 wt % agarose-7.5 wt % marine collagen-1 wt % alginate or 0.125 wt % agarose-10 wt % marine collagen-1 wt % alginate composite hydrogel support had the regular pore structure as a whole.

3. Fourier Transform Infrared Spectroscopy (FT-IR) Analysis

The hydrogel supports of 7 experimental groups prepared in Example 14-1 were dispensed in a 1 mL syringe at 100 μL, respectively to induce the gelation at 4° C. for 5 to 10 minutes and the cells were frozen at −20° C. for 24 hours and dried by a vacuum freeze dryer (FDS series, ilShinBioBase) for 24 hours and surface-treated with ion sputter (E-1010, Hitachi, Japan) and observed by an infrared spectroscopy system (FT-IR Microscopy System).

As a result, as shown in FIG. 60, the FT-IR spectrum of the 0.125 wt % agarose-1 wt % alginate composite hydrogel support showed the property of the parent molecule, and no significant additional band was present. The FT-IR spectrum of the 0.125 wt % agarose-7.5 wt % marine collagen-1 wt % alginate composite hydrogel support showed the properties of parent molecules, in particular 7.5 wt % marine collagen and no significant additional band was present.

From the above results, it was confirmed that the main component of FT-IR spectrum of 0.125 wt % agarose-7.5 wt % marine collagen-1 wt % alginate composite hydrogel support was mainly 7.5 wt % marine collagen.

Similarly, the FT-IR spectrum of 0.125 wt % agarose-10 wt % marine collagen-1 wt % alginate composite hydrogel support showed 10 wt % marine collagen characteristics as a parent molecule and no significant additional band was present. This FT-IR spectrum of 0.125 wt % agarose-10 wt % marine collagen-1 wt % alginate composite hydrogel support represents 10 wt % of marine collagen as its main component.

From the above results, no new chemical cross-links were formed in the agarose-marine collagen-alginate composite hydrogel support and it was confirmed that even though the chemical cross-links were not formed in the agarose-marine collagen-alginate composite hydrogel support, gelation occurs due to the physical bonding such as hydrogen bonding or other interaction according to the physical properties of the constituent molecules.

This is because a hydrogen bond is formed between a proton donor and a proton acceptor in the molecule, and as shown in FIG. 61, the interaction between marine collagen and agarose, the marine collagen and alginate occurs due to the hydrogen bond, in which the OH, $-NH_2$ and $C=O$ groups in the collagen can form hydrogen bonds with the OH groups in the agarose and OH and $C=O$ in the alginate.

4. Swelling Kinetics

The hydrogel supports of seven experimental groups prepared in Example 14-1 were dispensed into a 1 mL syringe at 100 μL, induced to the gelation at 4° C. for 5 to 10 minutes and dried at 40° C. for 24 hours. The weight of the dried agarose-marine collagen-alginate composite hydrogel support was weighed, immersed in phosphate buffered saline (PBS) and distilled water at 37° C., respectively to weigh at intervals of time for obtaining water content. The weighing was performed at room temperature after the solution flowing down was removed. The water content was calculated by the following formula:

Water content (%)=[(weight of swollen gel−weight of dried gel)/weight of dried gel]×100

As a result, as shown in FIG. 62, both 0.125 wt % agarose-7.5 wt % marine collagen-1 wt % alginate composite hydrogel and 0.125 wt % agarose-10 wt % marine collagen-1 wt % alginate composite hydrogel support showed slightly delayed swelling degree in PBS than that in distilled water. This is probably because the osmotic pressure of agarose-marine collagen-alginate composite hydrogel support acts largely in distilled water than PBS.

In addition, these supports exhibited considerably rapid swelling and reached equilibrium state within 2 hours.

<Example 15> Characterization of Three-Dimensional Culture of Cells in Agarose-Marine Collagen-Alginate Composite Hydrogel Support 1. Three-Dimensional Cell Culture Using Hydrogel Cell Culture Supporter As the method of Example 9, 0.125 wt % agarose-10 wt % marine collagen-1 wt % alginate composite hydrogel support was prepared, and cells were added to the 96-well plate and induced to the gelation at 4° C. for 5-10 minutes and then cultured in a medium.

2. Actin Staining and Analysis of Ability for Forming Spheroids by Hematoxylin-Eosin Staining To perform F-actin staining in total gel of human ovarian cancer cell A2780 cultured three-dimensionally for 7 days using agarose-marine collagen-alginate composite hydrogel support, the cell-cultured composite hydrogel support was washed twice with PBS and fixed with 100% methanol fixation solution at −20° C. for 20 minutes. Then, the cells were washed twice with PBS, and were infiltrated into 0.1% Triton-x 100 solution at room temperature for 5 minutes and washed twice with PBS.

To remove nonspecific staining, the cells were treated with 1% bovine serum albumin (BSA) solution at room temperature for 1 hour and then washed twice with PBS.

After that, actin-detecting Phalloidin-FITC (Promega, Madison, Wis., USA) was diluted to 1:50 in 0.2% BSA solution and reacted at 4° C. for 18 hours and washed with tris-buffered saline (TBS) three times. The composite hydrogel support was placed on a cover glass and the cells were contrast-stained with DAPI (Vector Lab, Inc., Burlingame, Calif., USA) for nuclear staining of the cell and encapsulated and analyzed by fluorescence microscopy.

In addition, hematoxylin-eosin (H-E) staining was performed on human ovarian cancer cells (A2780) cultured three-dimensionally for 7 days using an agarose-marine collagen-alginate composite hydrogel support. First, the cell-cultured composite hydrogel support was washed once with PBS and fixed in 100% methanol fixation at −20° C. for 20 minutes. The composite hydrogel support was nuclear-stained with hematoxylin for 5-10 minutes, washed with water and the cytoplasm was stained for 5-7 minutes in eosin. After washing with 100% ethanol, a part of the composite hydrogel support was peeled off, placed on a slide, covered with a cover glass to encapsulated and observed by an optical microscope.

As shown in FIG. 63 of the results of the optical microscope (a), hematoxylin-eosin staining (b), DAPI (c) and F-actin staining (d), cell spheroid having similar sizes was formed very regularly. Therefore, it was confirmed that the three-dimensional cell culture method using the agarose-marine collagen-alginate composite hydrogel support induces cell spheroid highly effectively.

As shown in FIG. 64, when EL4 cells were cultured for 1, 3, and 5 days, they were observed by a phase contrast microscope, it was confirmed that the formation of the cell spheroid was very regular and the cell spheroid was effectively induced as the incubation period was increased.

From the above results, it was confirmed that the three-dimensional cell culture method using the agarose-marine collagen-alginate composite hydrogel support can be very useful for studying the microenvironment and the interaction of cancer cells.

3. Analysis of the Ability of Spheroid Budding

In order to analyze the spheroid budding phenomenon, which plays an important role in the formation of the cell spheroid in the results of the above experiment, A2780 and R182 cells were cultured in agarose-marine collagen-alginate omposite hydrogel support for 7 days and the total hydrogel was subjected to hematoxylin-eosin staining and observed by an optical microscope. At the same time, unstained cells were observed by a phase contrast microscope.

As a result of the phase contrast microscope (a) and hematoxylin-eosin staining (b) in FIG. 65, the spheroid budding phenomenon was very effectively confirmed. Therefore, it has been confirmed that the three-dimensional cell culture method using the agarose-marine collagen-alginate composite hydrogel support can be useful for the study of the spheroid budding phenomenon.

4. Analysis of Drug Diffusion Ability in Spheroids

In order to evaluate the diffusion ability of a drug reaching cancer cells in a three-dimensional environment, the degree of the drug diffusion is measured by the three-dimensional culture model of human ovarian cancer cell (A2780) using an agarose-marine collagen-alginate composite hydrogel support, a solution using an agarose-marine collagen-alginate composite hydrogel support.

First, the cells were cultured until spheroids were formed in the agarose-marine collagen-alginate composite hydrogel support, and were treated with the anticancer drug doxorubicin (Cell Signaling Technology, Danvers, Mass., USA) at 1 µM for 24 hours. The hydrogel support was washed with PBS and the nuclear staining was performed with DAPI solution, and the distribution of doxorubicin in the spheroid was confirmed by confocal laser microscope (FV1000-IX81, Olympus, Japan).

As a result, it was confirmed that doxorubicin reaches cancer cells in all regions within the spheroid as shown in FIG. 66.

From the above results, it was confirmed that the three-dimensional cancer cell culture model using the agarose-marine collagen-alginate composite hydrogel support can be very useful for the screening method for the sensitivity assay of various drugs including anticancer drugs.

<Example 16> Analysis of Cell Growth Ability by Three-Dimensional Cell Culture Using Agarose-Marine Collagen-Alginate Composite Hydrogel Support 1. Three-Dimensional Cell Culture Using Hydrogel Cell Culture Support As the method of Example 9, 0.125 wt % agarose-7.5 wt % marine collagen-1 wt % alginate composite hydrogel support was prepared and A2780 cells were added to 96-well plate, induced to the gelation at 4° C. for 5-10 minutes and cultured in the medium. In addition, the conventional two-dimensional cell culture was also performed as a control for three-dimensional cell culture.

2. Cell Growth Assay

A2780 cells, a human ovarian cancer cell were cultured at $5 \times 10^5$ cells/gel in agarose-marine collagen-alginate composite hydrogel support, and the formation of spheroid of cells was observed by a phase contrast microscope after 0, 1, 3, 5 and 7 days. The spheroid sizes were measured on day 5 and 7. The WST-1 reagent was treated for 2 hours and the absorbance at 450 nm was measured using a microplate reader to calculate the percent growth rate.

As a result, as shown in FIGS. 67A and 67B, it was confirmed that the cells proliferated more rapidly in the two-dimensional environment at the initial stage of culture, but proliferated more rapidly in the three-dimensional environment after five days of culture. Also, as shown in FIG. 67C, it was confirmed that the size of the cell spheroid was more increased in the three-dimensional environment at day 7 group than day 5 group.

From the above results, it was confirmed that the three-dimensional cell culture method using the agarose-marine collagen-alginate composite hydrogel support is more suitable for forming a three-dimensional cell culture environment more similar to a living body than the two-dimensional cell culture, and the cell support according to the present invention can be used to construct a model suitable for cell culture studies.

3. CFSE Staining Analysis

CFSE staining was performed to confirm cell proliferating ability in an agarose-marine collagen-alginate composite hydrogel support. EL4 and CREC cells were treated with CellTracker™ Green CMFDA (Invitrogen, Carlsbad, Calif., USA) at 37° C. for 8 minutes for staining and then washed twice with PBS. The cells labeled with CFSE were cultured on composite hydrogel support for 0, 1, 2, and 3 days, and cell viability was observed by a fluorescence microscope.

As a result, it was confirmed that the cells cultured in the agarose-marine collagen-alginate composite hydrogel support showed a decrease in the number of CFSE-positive cells as the culture time increased. Therefore, it was confirmed that the culture in the agarose-marine collagen-alginate composite hydrogel support according to the present invention induced the proliferation of EL4 cells.

In addition, when EL4 and CREC cells were co-cultured, the EL4 cell proliferation was slower than EL4 cell culture alone.

From the above results, it was confirmed that the agarose-marine collagen-alginate composite hydrogel support of the present invention not only provides a three-dimensional environment suitable for the proliferation of CREC and EL4 cells, but also can be used as a very useful means for studying cell proliferation.

<Example 17> Analysis of Cell Viability by Three-Dimensional Culture of Cells in Agarose-Marine Collagen-Alginate Composite Hydrogel Support 1. Three-Dimensional Cell Culture Using Hydrogel Cell Culture Support As the method of Example 9, 0.125 wt % agarose-7.5 wt % marine collagen-1 wt % alginate composite hydrogel support was prepared, cells were added and placed in a 96-well plate, induced the gelation at 4° C. for 5-10 minutes and cultured in a medium.

2. Live/Dead Staining Analysis

In order to confirm the cytotoxicity of the hydrogel support of the present invention in cell culture using the agarose-marine collagen-alginate composite hydrogel support, human ovarian cancer cells (A2780) were cultured in marine collagen-alginate composite hydrogel support prepared by the Example 16-1 for 7 days and 10 days, and EL4 and CREC cells were cultured alone or co-cultured for 2 weeks. After washing the composite hydrogel support with PBS once, 2 µL calcein AM and 0.5 µL EthD-1 (LIVE/DEAD Viability Kit, Molecular Probes) were diluted in 1 mL PBS and stained in the dark for 30 minutes, and analyzed by a microscope (FV1000-IX81, Olympus, Japan).

As a result in FIG. 69, the viability of human ovarian cancer cells cultured in the agarose-marine collagen-alginate composite hydrogel support was very high.

Also, referring to FIG. 70, the viability of EL4 and CREC cells cultured in agarose-marine collagen-alginate composite hydrogel supports were very high.

From the above results, it was confirmed that the agarose-marine collagen-alginate composite hydrogel support of the present invention does not show cytotoxicity.

<Example 18> Analysis of Malignancy by Culturing Three-Dimensional Cancer Cells on Agarose-Marine Collagen-Alginate Composite Hydrogel Support 1. Three-Dimensional Cell Culture Using Hydrogel Cell Culture Support In the case of EL4 cells, 0.125 wt % agarose-10 wt % marine collagen-1 wt % alginate composite hydrogel support was prepared in the same manner as in Example 9, and cells were added and the mixture solution was added to a 1 mL syringe with 80 µL and induced the gelation at 4° C. for 5-10 minutes, and then cultured in a 48-well plate. In the case of A2780 cells, 0.125 wt % agarose-7.5 wt % marine collagen-1 wt % alginate composite hydrogel support was prepared in the same manner as in Example 9, cells were added, and the cells were added to 96-well plate at 4° C. for 5-10 minutes, and then cultured in the medium. In addition, the conventional two-dimensional cell culture was also performed as a control for three-dimensional cell culture.

2. Semi-Quantitative Reverse Transcription-Polymerase Chain Reaction Analysis (RT-PCR)

EL4 cells were cultured in agarose-marine collagen-alginate composite hydrogel support in two-dimensional and three-dimensional environments and the degree of expression of notch closely related to the malignancy of cancer cells was confirmed by RT-PCR analysis.

EL4 cells were cultured in agarose-marine collagen-alginate composite hydrogel support for 2 weeks in order to observe the expression of Notch by reverse transcription-polymerase chain reaction (hereinafter "RT-PCR") assay.

After that, 1.5 mL of QG buffer (Qiagen, Valencia, Calif., USA) and 2 mL of RLT buffer (Qiagen) were mixed with agarose-marine collagen-alginate composite hydrogel support and the agarose-marine collagen-alginate composite hydrogel was dissolved at room temperature and total RNA was isolated from the cultured cells according to the manufacturer's instructions using a trizol reagent (Ambion, Invitrogen).

To perform RT-PCR, a single-strand cDNA was synthesized by using a buffer containing 0.5 µg oligo (dT) 12-18, Oligo (dT) primer, 50 mM Tris-HCl (pH 8.3), 75 mM KCl, 3 mM $MgCl_2$, 40 mM DTT, 0.5 mM deoxynucleotide triphosphate (dNTP) mixture, 10 units RNase inhibitor and 200 units MMLV (Moloney murine leukemia virus) and reverse transcriptase (Promega, Madison, Wis., USA) from 2 µg of total RNA.

PCR reactions for mouse Notch-1, Notch-2 and GAPDH gene amplification were performed using the mouse Notch-1 forward and reverse primers of SEQ ID Nos. 25 and 26 in Table 1, the mouse Notch-2 forward and reverse primer of SEQ ID Nos. 27 and 28, or 0.4 µmol mouse GAPDH forward and reverse primer of SEQ ID Nos. 29 and 30, 1 µL cDNA sample, 25 µl of buffer solution containing 20 mM Tris-HCl (pH 8.4), 50 mM KCl, 1.5 mM $MgCl_2$, 0.1% Triton X-100, 0.2 mM dNTP mixture liquid and 5 unit Taq DNA polymerase (Promega), the initial denaturation was performed at 94° C. for 30 sec, at 60° C. for 30 sec and at 72° C. for 30 sec in 35 cycles. In the case of GAPDH, the reaction was carried out in 30 cycles.

The PCR reactions for human snail, vimentin, CD44 and GAPDH gene amplification consisted of the human snail forward and reverse primers of SEQ ID Nos. 31 and 32; human vimentin forward and reverse primers of SEQ ID Nos. 33 and 34; human CD44 forward and reverse primers of SEQ ID Nos. 35 and 36; human endothelin-1 forward and reverse primers of SEQ ID Nos. 37 and 38; or 0.4 pmol of the human GAPDH forward and reverse primers of SEQ ID Nos. 39 and 40 and 1 µL cDNA sample, 25 µl of buffer solution containing 20 mM Tris-HCl (pH 8.4), 50 mM KCl, 1.5 mM $MgCl_2$, 0.1% Triton X-100, 0.2 mM dNTP mixture liquid and 5 unit Taq DNA polymerase (Promega), the initial denaturation of CD44, Snail and GAPDH was performed at 94° C. for 5 minutes, at 94° C. for 30 sec, 57° C. for 30 sec and at 72° C. for 30 sec in 27 cycles.

In the case of vimentin, the initial denaturation was performed at 94° C. for 5 minutes, followed by 27 cycles at 94° C. for 30 seconds, 60° C. for 30 seconds, and 72° C. for 30 seconds. Finally, endothelin-1 was subjected to initial denaturation at 94° C. for 5 minutes, followed initial denaturation at 94° C. for 30 seconds, at 65° C. for 30 seconds, and at 72° C. for 30 seconds for 27 cycles.

After the PCR reaction, the reaction product samples produced by 2% agarose gel electrophoresis were stained with EtBr (Ethidium bromide) and analyzed under UV light illumination.

As a result, as shown in FIG. 71, the expression of both Notch-1 and Notch-2 was increased in the lymphoma cells cultured in the three-dimensional environment than the two-dimensional culture. This is the result of confirming that cancer cells cultured in three-dimensional environment are increased in malignancy unlike two-dimensional environment.

From the above results, it was confirmed that the three-dimensional cancer cell culture model using the agarose-marine collagen-alginate composite hydrogel support according to the present invention can effectively simulate a living body (in-vivo) environment.

In addition, in the human ovarian cancer cell host A2780 cells cultured in two-dimensional and three-dimensional environments, the malignancies of the cancer cells, particularly the expression of the snail and the vimentin, markers closely related to the epithelial-mesenchymal transition (EMT) CD19, an important marker for cancer stem cells, and endothelin-1, which plays a key role in tumor growth and metastasis, was confirmed.

As a result, it was confirmed that the cancer cells cultured in the three-dimensional environment increase the expression of the marker related to the malignancy of the cancer, than two-dimensional environment, as shown in FIG. 72.

From the above results, it was confirmed that the culture environment of cancer cells such as growth, progression, metastasis and malignancy of cancer in the three-dimensional cancer cell culture based on agarose-marine collagen-alginate composite hydrogel support, is very similar to those of living body. Because the three-dimensional cell culture method using the nanofiber support of the present invention provides in-vivo simulation environment which cannot be provided in the conventional two-dimensional cell culture method, it is useful for development of therapeutic agent for cancer cells as well as the research on cancer cell, growth, metastasis and malignancy of cancer cells.

TABLE 5

| Gene | SEQ ID No. | Primer Sequence |
|---|---|---|
| mouse Notch-1 | 25 | (Forward) 5'-CCCAGCAGGTGCA GCCACAG-3' |
| | 26 | (Reverse) 5'-GGTGATCTGGGAC GGCATGG-3' |
| mouse Notch-2 | 27 | (Forward) 5'-ATGTGGACGAGTG TCTGTTGC-3' |
| | 28 | (Reverse) 5'-GGAAGCATAGGCA CAGTCATC-3' |
| mouse GAPDH | 29 | (Forward) 5'-GAAATCCCATCAC CATCTTCCAGG-3' |
| | 30 | (Reverse) 5'-GAGCCCCAGCCTT CTCCATG-3' |
| Human Snail | 31 | (Forward) 5'-AGACCCACTCAGA TGTCAA-3' |
| | 32 | (Reverse) 5'-CATAGTTAGTCAC ACCTCGT-3' |
| Human vimentin | 33 | (Forward) 5'-GAGGAGATGCGGG AGCTGCG-3' |
| | 34 | (Reverse) 5'-CTGCCCTGCGTGA CGTACGT-3' |
| Human CD44 | 35 | (Forward) 5'-CTCCAGTGAAAGG AGCAGCA-3' |
| | 36 | (Reverse) 5'-AGCAGGGATTCTG TCTGTGC-3' |

TABLE 5-continued

| Gene | SEQ ID No. | Primer Sequence |
|---|---|---|
| Human endothelin-1 | 37 | (Forward) 5'-TGCTCCTGCTCTT CCCTGATGGATAAAGAGTGTGTC-3' |
| | 38 | (Reverse) 5'-GGTCACATAACGC TCTCTGGAGGGCTT-3' |
| Human GAPDH | 39 | (Forward) 5'-TGGAGAAACCTGC CAAGTATG-3' |
| | 40 | (Reverse) 5'-TTGTCATACCAGG AAATGAGC-3' |

<Example 19> Measurement of Anticancer Drug Susceptibility of Cancer Cells Cultured Three-Dimensional in Agarose-Marine Collagen-Alginate Composite Hydrogel Support: Analysis of Suitability as In-Vivo Simulation Anticancer Susceptibility Measurement Model 1. Three-Dimensional Cell Culture Using Hydrogel Cell Culture Support In the case of EL4 cells, 0.125 wt % agarose-10 wt % marine collagen-1 wt % alginate composite hydrogel support was prepared in the same manner as in Example 9, and cells were added, and the mixture liquid was added to a 1 mL syringe with 80 μL to induce the gelation at 4° C. for 5-10 minutes, and then cultured in a 48-well plate. In the case of A2780 cells, 0.125 wt % agarose-7.5 wt % marine collagen-1 wt % alginate composite hydrogel support was prepared in the same manner as in Example 9, the cells were added to 96-well plate to induce the gelation at 4° C. for 5-10 minutes, and then cultured in the medium. In addition, the conventional two-dimensional cell culture was also performed as a control for three-dimensional cell culture.

2. Cell Growth Assay

In order to perform a sensitivity assay for an anticancer agent, EL4 and human ovarian cancer cell A2780 were cultured in an agarose-marine collagen-alginate composite hydrogel support in a two-dimensional and three-dimensional environment and an efficacy test for an anticancer agent was performed. EL4 cells cultured in two-dimensional culture conditions and EL4 cells cultured three-dimensionally in an agarose-marine collagen-alginate composite hydrogel support were treated with 5 μM doxorubicin (5927, cell signaling) and 100 μM resveratrol and the human ovarian cancer cell A2780 was treated with paclitaxel at a concentration of 0.5 μM for 24 hours, and then with WST-1 reagent, and absorbance was measured at 450 nm by a microplate reader to calculate percent growth rate.

In addition, 10 and 20 μM paclitaxel, and 30 and 50 μM curcumin were added to A2780 cells cultured in two-dimensional condition and A2780 cells cultured three-dimensionally for 7 days in agarose-marine collagen-alginate composite hydrogel supports, and the control group was treated with DMSO at the same concentration as the experimental group. The WST-1 reagent was then treated and the absorbance at 450 nm was measured by a microplate reader to calculate the percentage growth rate.

As a result of FIG. 73A, when EL4 cells as a mouse lymphoma cell were treated with 5 μM doxorubicin, the viability was 58.6% (P<0.001) in the two-dimensional environment as compared with the control group, and cell viability was 71.4% (P<0.01) compared to the control group. As shown in FIG. 73B, when the cell was treated with 100 μM resveratrol, the viability was 50.2% (P<0.001) in the two-dimensional environment as compared with the control group, and the cell viability was increased to 93.5% in the three-dimensional environment compared to the control group.

As shown in FIG. 73C, when human ovarian cancer cell A2780 was treated with 0.5 μM paclitaxel, the viability was 60.9% (P<0.001) in the two-dimensional environment as compared with the control group. In the three-dimensional environment, and the cell viability was 94.2%.

From the above results, it was confirmed that the three-dimensional cancer cell culture model using the agarose-marine collagen-alginate composite hydrogel support according to the present invention can be very useful for studying the drug resistance mechanism against the anticancer agent and the sensitivity to the anticancer agent.

In addition, A2780 cells were cultured in an agarose-marine collagen-alginate composite hydrogel support in a two- and three-dimensional environment, and paclitaxel and curcumin efficacy tests for ovarian cancer were conducted. As the results of FIG. 74, the viability was 12.3% (P<0.01) in the case of the treatment of 10 μM paclitaxel and 6.4% (P<0.001) in the case of the treatment of 20 μM paclitaxel in the two-dimensional environment. The viability was 40.2% (P<0.001) in the case of the treatment of 10 μM paclitaxel and 51.4% (P<0.05) in the case of the treatment of 20 μM paclitaxel in the three-dimensional environment.

Also, when curcumin was treated at a concentration of 30 and 50 μM, the cell viability was 42.5% (P<0.001) at 30 μM and 36.7% (P<0.001) at 50 μM in the two-dimensional environment and the cell viability was 95.0% at 30 μM and 82.4% at 50 μM in the two-dimensional environment.

From the above results, it was confirmed that the drug resistance to the anticancer drug effectively exhibited in the three-dimensional environment rather than the two-dimensional environment. Through this, it was confirmed that the three-dimensional cancer cell culture model using the agarose-marine collagen-alginate composite hydrogel support was excellent in assay for a drug resistance mechanism research for anticancer drugs and susceptibility to anticancer drugs.

3. Cell Morphology and Cytokeratin Staining

Human ovarian cancer cells were cultured in an agarose-marine collagen-alginate composite hydrogel support in a three-dimensional environment, and immunostaining was performed with an antibody against cytokeratin, which is a marker specifically expressed in epithelial cells.

Firstly, after three-dimensional culture of A2780 cells on the agarose-marine collagen-alginate composite hydrogel support of the present invention, 10 μM paclitaxel and 30 μM curcumin, which are anticancer agents well-known to have a high killing effect on human ovarian cancer cells in the conventional two-dimensional culture, were treated for 2 days, respectively and control group was treated with the same concentration of DMSO for 2 days. The agarose-marine collagen-alginate composite hydrogel support was then washed once with PBS and fixed with a 100% methanol fixation solution at −20° C. for 20 minutes. To remove nonspecific staining, the cells were treated with 1% BSA solution for 1 hour at room temperature and then stained with plate-cytochokeratin antibody (Sigma-Aldrich) diluted to 1:50 for 18 hours at 4° C. After washing once with PBS, nuclear staining was performed with DAPI solution at room temperature for 30 minutes and observed by a fluorescence microscope. At the same time, unstained cells were observed by a phase contrast microscope.

As a result of FIG. 75, unlike the two-dimensional environment, the cells cultured in the three-dimensional environment effectively showed the drug resistance to the anticancer drug.

From the above results, it was confirmed that the three-dimensional cancer cell culture model using the agarose-marine collagen-alginate composite hydrogel support according to the present invention can be very useful in studying the drug resistance mechanism against the anticancer agent and the sensitivity to the anticancer agent.

<Example 20> Measurement of Cancer Stem Cell Formation Ability and Cancer Cell Differentiation Ability in Cancer Cell Cultured Three-Dimensionally in Agarose-Marine Collagen-Alginate Composite Hydrogel Support: Induction and Growth of In-Vivo Simulation Cancer Stem Cell and its Suitability as Cancer Cell Differentiation Model 1. Three-Dimensional Cell Culture Using Hydrogel Cell Culture Support 0.125 wt % agarose-10 wt % marine collagen-1 wt % alginate composite hydrogel support was prepared at the final concentration in the same manner as in Example 9, EL4 cells were added, and 80 μL of the mixture solution was added to a 1 mL syringe to induce the gelation at 4° C. for 5-10 minutes, and the cells were placed in a 48-well plate and cultured.

2. Analysis of Cell Surface Molecule Expression Ising Flow Cytometer

EL4 cells were cultured for 10 days in a three-dimensional (3D) agarose-marine collagen-alginate composite hydrogel support and a 96-well plate in a two-dimensional environment (2D), and then analyzed using a flow cytometer (FACS canto II, flow cytometer BD Biosciences).

To separate the cultured cells form the hydrogel support, 40 μm cell strainer (SPL Life Sciences) was and 2D cells were isolated using conventional methods. The separated cells were washed twice with Hank's Balanced Salt Solution (HBSS, GibcoLife Technologies) and resuspended in 3 mL of FACS buffer (0.1% BSA, 0.1% sodium chloride, 500 mL HBSS) followed by centrifugation at 4° C. and 1500 rpm for 4 minutes. After removing the supernatant, the cells were resuspended and the cells were pre-incubated with anti-FcγRII/III (2.4G2, hybridoma supernatant) to avoid nonspecific binding with the antibody. Then, the cells were incubated in HBSS containing 2% FBS by reacting with the objective primary anti-mouse monoclonal antibody, i.e. anti-CD4 antibody conjugated with FITC or PE (FITC-CD4 or PE-CD4), APC-conjugated anti-CD8 antibody (APC-CD8), PE-CY7-conjugated anti-c-kit antibody (PE-CY7-c-kit) and APC-conjugated anti-sca-1 antibody (APC-sca-1) at 5-10 μg/mL for 30 minutes under ice cooling.

Background fluorescence was determined by cells that were reacted with isotype-matched nonreactive antibodies.

The cells were then washed twice with HBSS, resuspended in 500 μL of FACS buffer, and analyzed for expression of cell surface molecules by a flow cytometer using the Dot-plot method. The obtained results were analyzed using FlowJo software (Tree Star, Ashland, Oreg., USA).

As a result of FIG. 76, the proportion of c-kit$^+$sca-1$^+$ cells corresponding to cancer stem cells among the EL4 cells cultured for 10 days under the 2D environment was 4.6% The proportion of EL4 cells c-kit$^+$sca-1$^+$ cancer stem cells considerably increased to 31.9%. This is a result of confirming that the culture environment of cancer cells such as the formation and growth of cancer stem cells is very similar to the living body in the three-dimensional cancer cell culture based on the agarose-marine collagen-alginate composite hydrogel support.

Accordingly, the three-dimensional cell culture method using the agarose-marine collagen-alginate composite hydrogel support according to the present invention provides an in-vivo environment that could not be provided by the conventional two-dimensional cell culture method, is useful for the research on the anticancer drug resistance mechanism and the development of the highly efficient chemotherapy method.

Although the present invention has been described in detail based on particular features thereof, and it is obvious to those skilled in the art that these specific technologies are merely preferable embodiments and thus the scope of the present invention is not limited to the embodiments. Therefore, the substantial scope of the present invention is defined by the accompanying claims and equivalent thereof.

The invention claimed is:

1. A three-dimensional cell culturing method, comprising:
   a step of mixing and culturing an alginate solution and cells;
   a step of adding a collagen solution to a cultured mixture to prevent cell detachment; and
   a step of adding an agarose solution to a mixture including collagen and allowing the mixture to stand, thereby inducing gelation,
   wherein the collagen is added in an amount of 1 to 30 parts by weight based on 100 parts by weight of the mixture.

2. The method of claim 1, comprising:
   mixing the alginate solution and the cells and culturing at a temperature of 25 to 37° C. for 5 to 30 minutes;
   adding the collagen solution to the cultured mixture to prevent cell detachment at a temperature of 25 to 37° C. for 5 to 30 minutes; and
   adding the agarose solution to a mixture including collagen and allowing the mixture to stand for 5 to 30 minutes at a temperature of 4 to 25° C., thereby inducing gelation.

3. The method of claim 1, wherein the collagen is marine-derived collagen.

4. The method of claim 1, wherein the alginate is added in an amount of 0.5 to 2 parts by weight based on 100 parts by weight of the cultured mixture.

5. The method of claim 1, wherein the agarose is added in an amount of 0.1 to 0.5 parts by weight based on 100 parts by weight of the mixture.

6. The method of claim 1, wherein the cells are selected from the group consisting of normal cells and cancer cells.

7. The method of claim 6, wherein the cancer cells are solid cancer cell selected from the group consisting of ovarian cancer, breast cancer, gastric cancer, colon cancer, rectal cancer, lung cancer, liver cancer, prostate cancer, renal cancer, pancreatic cancer, thyroid cancer, uterine cancer, laryngeal cancer, hydrocephalus, laryngeal cancer, guinea, salivary gland cancer, esophageal cancer, osteosarcoma, tongue cancer, biliary cancer, glioma, bone cancer and unknown cause cancer.

8. The method of claim 6, wherein the cell is a blood cancer cell selected from the group consisting of B cell lymphoma, T cell lymphoma, leukemia, and multiple myeloma.

\* \* \* \* \*

SEQUENCE LISTING

<160> NUMBER OF SEQ ID NOS: 40

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
cctgtcatcc ccgtctacac        20

<210> SEQ ID NO 2
<211> LENGTH: 19
<212> TYPE: DNA
<213> ORGANISM: Artificial Sequence
<220> FEATURE:
<223> OTHER INFORMATION: primer

<400> SEQUENCE: 2
cacatggagt ccgccgtaa        19

```
<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
tacaagtgcg actgtgaccc                                                    20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
cacacgtagc cactggtcat                                                    20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
caaccgcaat ggaggctatg                                                    20

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
gcgaaggcac aatcatcaat gtt                                                23

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
tggcgacctc acttacgact                                                    20

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
cactggcagt tataggtgtt gac                                                23

<210> SEQ ID NO 9
<211> LENGTH: 19
<212> TYPE: DNA
<213> ORGANISM: Artificial Sequence
<220> FEATURE:
<223> OTHER INFORMATION: primer
```

```
<400> SEQUENCE: 9
cctggctcct tcaactgcc                                                      19

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
gcaagtaggt ccagacaggt                                                     20

<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
agacccactc agatgtcaa                                                      19

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
catagttagt cacacctcgt                                                     20

<210> SEQ ID NO 13
<211> LENGTH: 19
<212> TYPE: DNA
<213> ORGANISM: Artificial Sequence
<220> FEATURE:
<223> OTHER INFORMATION: primer

<400> SEQUENCE: 13
ggtcaagaag catttcaac                                                      19

<210> SEQ ID NO 14
<211> LENGTH: 18
<212> TYPE: DNA
<213> ORGANISM: Artificial Sequence
<220> FEATURE:
<223> OTHER INFORMATION: primer

<400> SEQUENCE: 14
ggtaatgtgt gggtccga                                                       18

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
cgaaaccatg aactttctgc                                                     20
```

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
cctcagtggt cacacactcc                                              20

<210> SEQ ID NO 17
<211> LENGTH: 19
<212> TYPE: DNA
<213> ORGANISM: Artificial Sequence
<220> FEATURE:
<223> OTHER INFORMATION: primer

<400> SEQUENCE: 17
ggcgcgaacg acaagaaaa                                               19

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
gtggcaactg atgagcaagc                                              20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
ctccagtgaa aggagcagca                                              20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
agcagggatt ctgtctgtgc                                              20

<210> SEQ ID NO 21
<211> LENGTH: 36
<212> TYPE: DNA
<213> ORGANISM: Artificial Sequence
<220> FEATURE:
<223> OTHER INFORMATION: primer

<400> SEQUENCE: 21
tgctcctgct cttccctgat ggataaagag tgtgtc                            36

<210> SEQ ID NO 22
<211> LENGTH: 27
<212> TYPE: DNA
<213> ORGANISM: Artificial Sequence
<220> FEATURE:
<223> OTHER INFORMATION: primer

```
<400> SEQUENCE: 22
ggtcacataa cgctctctgg agggctt                                          27

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
tggagaaacc tgccaagtat g                                                21

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
ttgtcatacc aggaaatgag c                                                21

<210> SEQ ID NO 25
<211> LENGTH: 20
<212> TYPE: DNA
<213> ORGANISM: Artificial Sequence
<220> FEATURE:
<223> OTHER INFORMATION: mouse Notch-1 forword primer

<400> SEQUENCE: 25
cccagcaggt gcagccacag                                                  20

<210> SEQ ID NO 26
<211> LENGTH: 20
<212> TYPE: DNA
<213> ORGANISM: Artificial Sequence
<220> FEATURE:
<223> OTHER INFORMATION: mouse Notch-1 reverse primer

<400> SEQUENCE: 26
ggtgatctgg gacggcatgg                                                  20

<210> SEQ ID NO 27
<211> LENGTH: 21
<212> TYPE: DNA
<213> ORGANISM: Artificial Sequence
<220> FEATURE:
<223> OTHER INFORMATION: mouse Notch-2 forword primer

<400> SEQUENCE: 27
atgtggacga gtgtctgttg c                                                21

<210> SEQ ID NO 28
<211> LENGTH: 21
<212> TYPE: DNA
<213> ORGANISM: Artificial Sequence
<220> FEATURE:
<223> OTHER INFORMATION: mouse Notch-2 reverse primer

<400> SEQUENCE: 28
ggaagcatag gcacagtcat c                                                21
```

```
<210> SEQ ID NO 29
<211> LENGTH: 24
<212> TYPE: DNA
<213> ORGANISM: Artificial Sequence
<220> FEATURE:
<223> OTHER INFORMATION: mouse GAPDH forword primer

<400> SEQUENCE: 29
gaaatcccat caccatcttc cagg                                              24

<210> SEQ ID NO 30
<211> LENGTH: 20
<212> TYPE: DNA
<213> ORGANISM: Artificial Sequence
<220> FEATURE:
<223> OTHER INFORMATION: mouse GAPDH reverse primer

<400> SEQUENCE: 30
gagccccagc cttctccatg                                                   20

<210> SEQ ID NO 31
<211> LENGTH: 19
<212> TYPE: DNA
<213> ORGANISM: Artificial Sequence
<220> FEATURE:
<223> OTHER INFORMATION: Human Snail forword primer

<400> SEQUENCE: 31
agacccactc agatgtcaa                                                    19

<210> SEQ ID NO 32
<211> LENGTH: 20
<212> TYPE: DNA
<213> ORGANISM: Artificial Sequence
<220> FEATURE:
<223> OTHER INFORMATION: Human Snail reverse primer

<400> SEQUENCE: 32
catagttagt cacacctcgt                                                   20

<210> SEQ ID NO 33
<211> LENGTH: 20
<212> TYPE: DNA
<213> ORGANISM: Artificial Sequence
<220> FEATURE:
<223> OTHER INFORMATION: Human vimentin forward primer

<400> SEQUENCE: 33
gaggagatgc gggagctgcg                                                   20

<210> SEQ ID NO 34
<211> LENGTH: 20
<212> TYPE: DNA
<213> ORGANISM: Artificial Sequence
<220> FEATURE:
<223> OTHER INFORMATION: Human vimentin reverse primer

<400> SEQUENCE: 34
ctgccctgcg tgacgtacgt                                                   20

<210> SEQ ID NO 35
<211> LENGTH: 20
<212> TYPE: DNA
<213> ORGANISM: Artificial Sequence
<220> FEATURE:
<223> OTHER INFORMATION: Human CD44 forward primer
```

```
<400> SEQUENCE: 35
ctccagtgaa aggagcagca                                                    20

<210> SEQ ID NO 36
<211> LENGTH: 20
<212> TYPE: DNA
<213> ORGANISM: Artificial Sequence
<220> FEATURE:
<223> OTHER INFORMATION: Human CD44 reverse primer

<400> SEQUENCE: 36
agcagggatt ctgtctgtgc                                                    20

<210> SEQ ID NO 37
<211> LENGTH: 36
<212> TYPE: DNA
<213> ORGANISM: Artificial Sequence
<220> FEATURE:
<223> OTHER INFORMATION: Human endothelin-1 forward primer

<400> SEQUENCE: 37
tgctcctgct cttccctgat ggataaagag tgtgtc                                  36

<210> SEQ ID NO 38
<211> LENGTH: 27
<212> TYPE: DNA
<213> ORGANISM: Artificial Sequence
<220> FEATURE:
<223> OTHER INFORMATION: Human endothelin-1 reverse primer

<400> SEQUENCE: 38
ggtcacataa cgctctctgg agggctt                                            27

<210> SEQ ID NO 39
<211> LENGTH: 21
<212> TYPE: DNA
<213> ORGANISM: Artificial Sequence
<220> FEATURE:
<223> OTHER INFORMATION: Human GAPDH forward primer

<400> SEQUENCE: 39
tggagaaacc tgccaagtat g                                                  21

<210> SEQ ID NO 40
<211> LENGTH: 21
<212> TYPE: DNA
<213> ORGANISM: Artificial Sequence
<220> FEATURE:
<223> OTHER INFORMATION: Human GAPDH reverse primer

<400> SEQUENCE: 40
ttgtcatacc aggaaatgag c                                                  21
```